(12) United States Patent
Atlas

(10) Patent No.: US 11,076,763 B2
(45) Date of Patent: Aug. 3, 2021

(54) REMOTE PHYSIOLOGICAL MONITOR

(71) Applicant: Atlasense Biomed Ltd., Hod Hasharon (IL)

(72) Inventor: Dan Atlas, Hod Hasharon (IL)

(73) Assignee: Atlasense Biomed Ltd., Hod Hasharon (IL)

( * ) Notice: Subject to any disclaimer, the term of this patent is extended or adjusted under 35 U.S.C. 154(b) by 840 days.

(21) Appl. No.: 15/519,470

(22) PCT Filed: Oct. 15, 2015

(86) PCT No.: PCT/US2015/055785
§ 371 (c)(1),
(2) Date: Apr. 14, 2017

(87) PCT Pub. No.: WO2016/061381
PCT Pub. Date: Apr. 21, 2016

(65) Prior Publication Data
US 2017/0238812 A1 Aug. 24, 2017

Related U.S. Application Data

(60) Provisional application No. 62/063,972, filed on Oct. 15, 2014.

(51) Int. Cl.
*A61B 5/0205* (2006.01)
*H04R 25/00* (2006.01)
(Continued)

(52) U.S. Cl.
CPC .......... *A61B 5/0205* (2013.01); *A61B 5/0002* (2013.01); *A61B 5/01* (2013.01);
(Continued)

(58) Field of Classification Search
None
See application file for complete search history.

(56) References Cited

U.S. PATENT DOCUMENTS 6,897,788 B2    5/2005   Khair et al.
9,101,275 B2    8/2015   Thakur et al.
(Continued)

FOREIGN PATENT DOCUMENTS

WO     2016/061381     4/2016

OTHER PUBLICATIONS

PCT International Search Report for International Application No. PCT/US15/55785, dated Jan. 8, 2016.

*Primary Examiner* — Joseph M Dietrich
(74) *Attorney, Agent, or Firm* — Greenberg Traurig, LLP; David J. Dykeman; Jaime L. Burke

(57) ABSTRACT

A system comprising a remotely programmable micromonitor with a wireless sensing system-on-module (SOM), one or more sensors to detect one or more conditions in a subject by monitoring one or more parameters associated with the conditions by comparing any monitored parameter to a baseline measurement of the monitored parameter from the subject, a plurality of sensors corresponding to a monitored parameter and connected to the micromonitor to convey measurements of all monitored parameters, the sensors including at least one of a non-optical pulse wave sensor or an electrocardiogram (ECG) sensor, a communications module capable of communicating with a wireless technology, wherein the module can send an alert signal to the subject or an attending physician or a remote service center or any other subject, and one or more algorithms for monitoring conditions and/or for predicting conditions, including at least one of a fall detection or fall prediction algorithm.

7 Claims, 51 Drawing Sheets

(51) Int. Cl.
*A61B 5/00* (2006.01)
*A61B 5/01* (2006.01)
*A61B 5/11* (2006.01)
*A61N 1/04* (2006.01)
*A61B 7/00* (2006.01)
*A61N 1/372* (2006.01)
*A61B 7/02* (2006.01)
*G16H 40/67* (2018.01)
*A61B 5/25* (2021.01)
*A61B 5/296* (2021.01)
*A61B 5/316* (2021.01)
*A61B 5/332* (2021.01)
*A61B 5/352* (2021.01)
*A61B 7/04* (2006.01)
*G08B 21/04* (2006.01)
*A61B 5/0531* (2021.01)
*A61B 5/1455* (2006.01)
*A61B 5/021* (2006.01)
*A61B 5/389* (2021.01)
*A61B 5/024* (2006.01)
*A61B 5/08* (2006.01)

(52) U.S. Cl.
CPC .............. *A61B 5/1117* (2013.01); *A61B 5/25* (2021.01); *A61B 5/296* (2021.01); *A61B 5/316* (2021.01); *A61B 5/332* (2021.01); *A61B 5/352* (2021.01); *A61B 5/4818* (2013.01); *A61B 5/741* (2013.01); *A61B 5/746* (2013.01); *A61B 5/747* (2013.01); *A61B 7/003* (2013.01); *A61B 7/02* (2013.01); *A61B 7/04* (2013.01); *A61N 1/0456* (2013.01); *A61N 1/37258* (2013.01); *A61N 1/37282* (2013.01); *G08B 21/0446* (2013.01); *G16H 40/67* (2018.01); *H04R 25/554* (2013.01); *A61B 5/02108* (2013.01); *A61B 5/02125* (2013.01); *A61B 5/02438* (2013.01); *A61B 5/0531* (2013.01); *A61B 5/08* (2013.01); *A61B 5/14551* (2013.01); *A61B 5/389* (2021.01); *A61B 5/74* (2013.01); *A61B 2560/0204* (2013.01); *A61B 2560/0209* (2013.01); *A61B 2560/0252* (2013.01); *A61B 2560/0412* (2013.01); *A61B 2562/028* (2013.01); *A61B 2562/0219* (2013.01); *A61B 2562/06* (2013.01); *H04R 25/603* (2019.05); *H04R 2225/55* (2013.01); *H04R 2225/61* (2013.01)

(56) References Cited

U.S. PATENT DOCUMENTS

| | | | |
|---|---|---|---|
| 2002/0109621 A1* | 8/2002 | Khair | A61B 5/0006 341/174 |
| 2008/0288500 A1 | 11/2008 | Thakur et al. | |
| 2009/0224925 A1* | 9/2009 | Gannot | A61B 5/1117 340/573.1 |
| 2011/0246114 A1* | 10/2011 | Jin | G08B 21/043 702/94 |
| 2013/0150686 A1* | 6/2013 | Fronterhouse | G06F 19/3418 600/323 |
| 2013/0310657 A1* | 11/2013 | Sullivan | A61B 5/742 600/301 |
| 2014/0275925 A1* | 9/2014 | Thakur | A61B 7/04 600/377 |
| 2014/0276238 A1* | 9/2014 | Osorio | A61B 5/0205 600/595 |

* cited by examiner

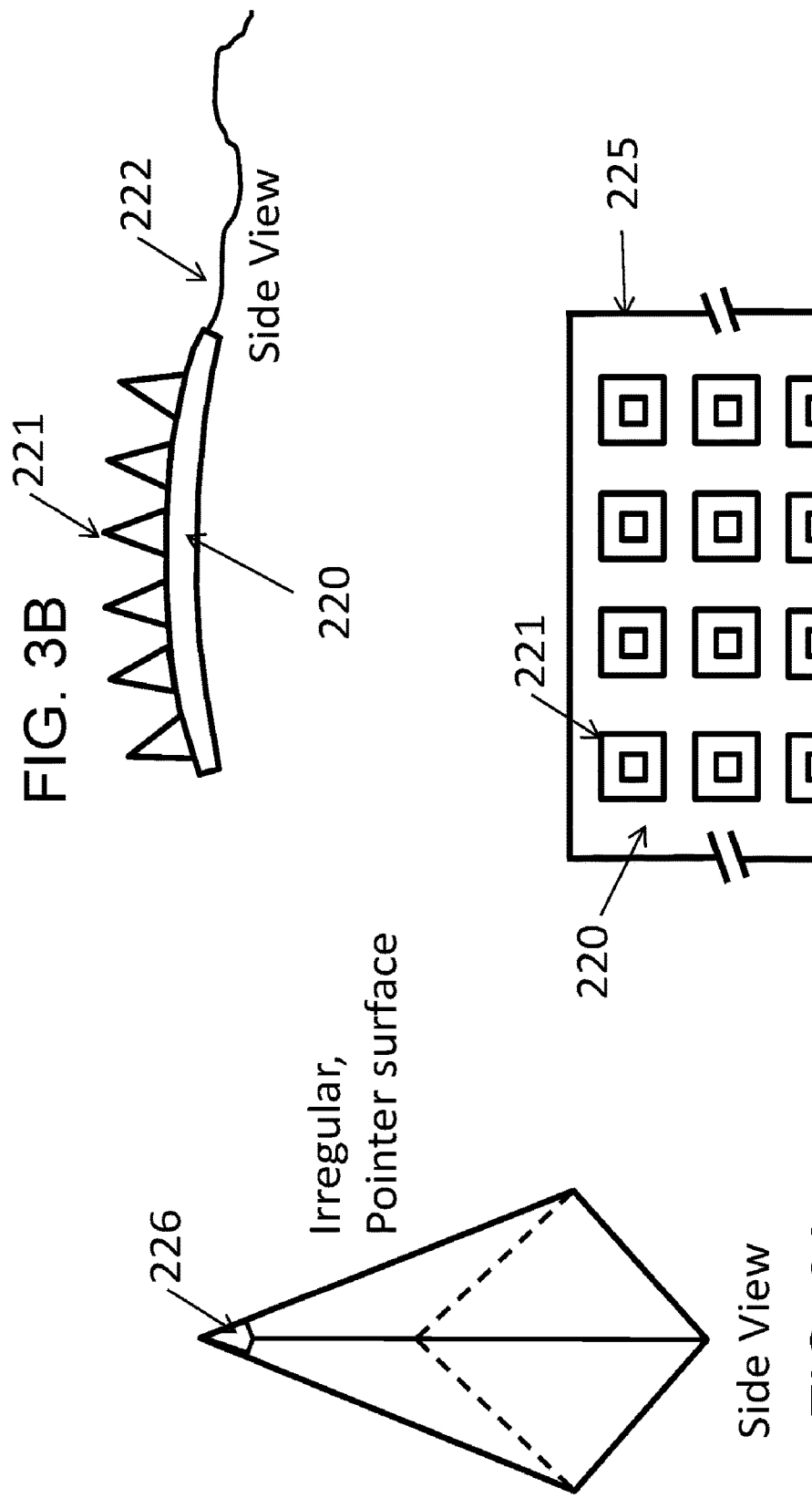

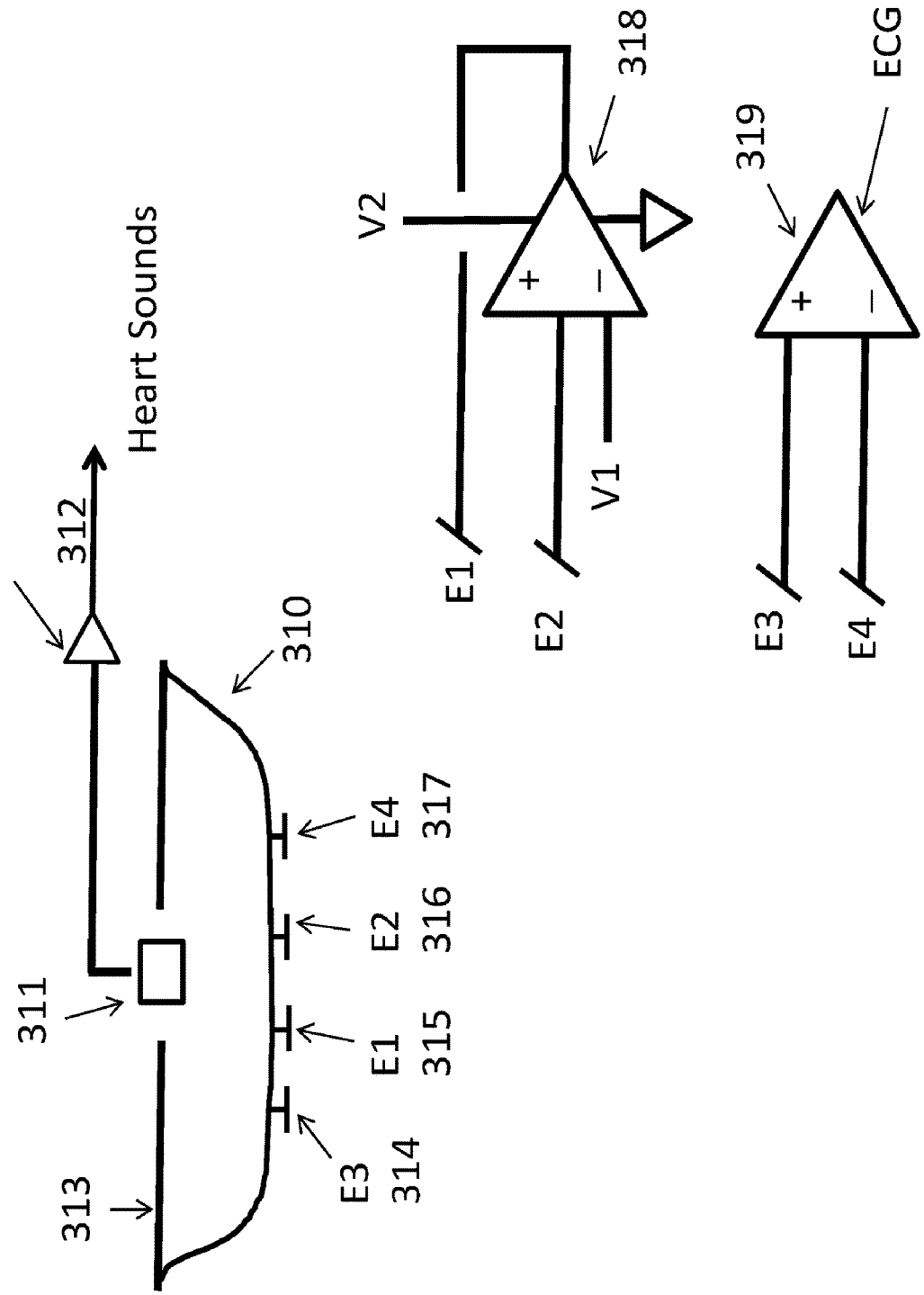

8-Channel Switch

Analog to Digital Converter

Mixed Signal Board - Block Diagram

REMOTE PHYSIOLOGICAL MONITOR

CROSS-REFERENCE TO RELATED APPLICATIONS

The present application is a U.S. national phase application of PCT International Patent Application No. PCT/US2015/055785, filed on Oct. 15, 2015, which claims priority to and the benefit of U.S. Provisional Patent Application No. 62/063,972, filed Oct. 15, 2014, each of which is hereby incorporated by reference in their entireties.

STATEMENT REGARDING FEDERALLY SPONSORED RESEARCH OR DEVELOPMENT

None.

BACKGROUND

Clinical physiological monitoring is often associated with several electrodes placed upon a person, with wires and cables leading to a monitor. Examples of such monitors are the AR7000 platform and the FDA approved cardio-respiratory monitor LifeGuard AR8800. A visit to a doctor's office for a checkup also involves the connection to variety of monitoring devices, such as a fitness heart rate monitor which is generally worn on the chest using a strap. Many wearable, wireless monitoring configurations exist, none having a broad scope of monitoring capabilities.

There are many shortcomings to current monitoring technologies. For example, some are required to be done in the home, where self-monitoring is not practical and inconvenient and compliance is a significant issue, especially when chronic monitoring is required. In the clinical setting, multiple electrodes, sensor and cables are costly and obtrusive, especially when different devices are needed for different types of monitoring. In rehabilitation heart rate applications, the wearing of a chest strap is significantly uncomfortable and can lead to non-compliance if the monitoring is intended to be done outside the clinical setting.

SUMMARY

Remote physiological monitoring devices, systems, and methods are disclosed herein. In some embodiments, a system for real-time monitoring of a subject's physiological condition comprising a micro-monitor with a wireless sensing system-on-module (SOM), a plurality of sensors, a communications module capable of communicating with a wireless technology, and one or more algorithms for monitoring conditions and/or for predicting conditions. The monitor is remotely programmable to activate and deactivate one or more sensors and detect one or more conditions in a subject by monitoring one or more parameters associated with the conditions and comparing any monitored parameter to a baseline measurement of the monitored parameter from the subject. Each sensor corresponds to a monitored parameter and is connected to the micro-monitor to convey measurements of all monitored parameters, the sensors including at least one of a non-optical pulse wave sensor or an electrocardiogram (ECG) sensor. The module can send an alert signal to the subject or an attending physician or a remote service center or any other subject. The algorithms include at least one of a fall detection algorithm or a fail prediction algorithm.

In some embodiments, the alert is transmitted upon the monitor detecting a pre-defined and remotely programmed significant physiological change in a measured parameter as compared to the subject's baseline measurement.

In some embodiments, the monitored parameters comprise electrocardiography (ECG), electromyography (EMG), respiration of the subject, body temperature, ambient temperature and body position of the subject. In some embodiments, the monitored parameters further comprise skin conductance, body impact, relative blood pressure trends of the subject and stethoscope heart and lung sounds of the subject.

In some embodiments the system further comprises a microphone, the microphone configured to enable a remotely programmable hearing aid. In some embodiments, the system further comprises a remotely programmable transcutaneous electrical nerve stimulation (TENS) unit. In some embodiments, the system further comprises a body contacting stethoscope membrane. In some embodiments, the membrane further comprises a skin contacting side with body contacting electrodes further comprising an ECG electrode, an EMG electrode, and a skin conductance electrode. In some embodiments, the non-contacting side of the membrane further comprises a respiration and blood pressure pulse wave sensor that are independent of the electrodes.

In some embodiments, the sensors comprise body contacting electrodes, the electrodes having a shape configured so that a body contact is made through body hair and further configured to enable the skin to breathe. In some embodiments, each sensor further comprises a conditioning sub-module which can be powered up or powered down remotely to conserve battery energy.

In some embodiments, the system further comprises a speech engine for instructing the subject via an earphone or by activating the piezo respiration and pulse wave sensor as a speaker. In some embodiments, the system further comprises an automatic event activated microphone, wherein the microphone is automatically activated for a remote verbal notification upon sensing a physiological distress or a life threatening event such as an abnormal heart rate or an arrhythmia, an apnea, an asthmatic episode, an abnormal blood pressure deviation, or an abnormal temperature.

In some embodiments, at least one monitored parameter is an ECG R wave, and at least one other monitored parameter is a blood pressure pulse waveform, and wherein the system is configured to measure a delay between the two parameters for determining a pulse transit time (PTT).

In some embodiments, a system for real-time monitoring of a subject's physiological condition comprising a micro-monitor with a wireless sensing system-on-module (SOM), a plurality of sensors, a communications module capable of communicating with a wireless technology a fall detection algorithm incorporating a startle response monitoring function in addition to physiological changes, a fall prediction algorithm incorporating a Lissajous pattern analysis of body sway to predict falls, a blood pressure trending algorithm which uses the non-optical pulse sensor with the ECG to measure pulse transit time (PTT), and an automatic distress activated microphone. The monitor is remotely programmable to detect one or more conditions in a subject by monitoring one or more parameters associated with the conditions and comparing any monitored parameter to a baseline measurement of the monitored parameter from the subject. Each sensor corresponds to a monitored parameter and connected to the micro-monitor to convey measurements of all monitored parameters, the sensors comprising at least a non-optical pulse wave sensor and an electrocardiogram (ECG) sensor. The module can send an alert signal to the subject or an attending physician or another person, the alert being transmitted to the subject or the physician or other person upon the monitor detecting a pre-defined and remotely programmed threshold physiological change in a measured parameter as compared to the subject's baseline measurement.

In some embodiments, a method for monitoring a subject's physiological condition comprising (a) placing a monitoring system on a subject, the system configured to detect one or more conditions in the subject, (b) measuring the parameters from the subject at a baseline time to establish a baseline condition for the subject for each parameter, (c) measuring new parameters at a time after the baseline measurement is taken to establish a new condition for the subject for each parameter, (d) comparing the new condition to the baseline condition, and (e) determining if there is a changed condition in the subject for each parameter. The system comprises a micro-monitor with a wireless sensing system-on-module (SOM), the monitor being remotely programmable to detect one or more conditions in a subject by monitoring one or more parameters associated with the conditions and comparing any monitored parameter to a baseline measurement of the monitored parameter from the subject, a plurality of sensors, each sensor corresponding to a monitored parameter and connected to the micro-monitor to convey measurements of all monitored parameters, the sensors comprising at least a non-optical pulse wave sensor and an electrocardiogram (ECG) sensor, a communications module capable of communicating with a wireless technology, wherein the module can send an alert signal to the subject or to an attending physician, and one or more algorithms for monitoring conditions and/or for predicting conditions, the algorithms including at least one of a fall detection algorithm, a fall prediction algorithm, or a blood pressure trending algorithm which uses the non-optical pulse sensor with the ECG to measure pulse transit time (PTT).

In some embodiments, determining the changed condition of the subject further comprises differentiating between episodes of central and obstructive sleep apnea with the aid of a stethoscope.

In some embodiments, the fall detection algorithm further comprises a sensor for a sensed impact and the algorithm assesses a series of physiological changes including at least a heart rate change and a startle response. In some embodiments, the fail prediction algorithm predicts a likelihood of the subject falling by first testing the subject with an X-Y acceleration sensor while the subject is standing to generate a subject baseline state resulting in a simulated line, wherein line lengths comprise an X-Y body sway, wherein a line length of the simulated line is compared to a line length of a second simulated line measured in a second testing of the subject at a later and equivalent period of time, and wherein an increasing line length with respect to the baseline state enables detection by the monitoring system of a progressive postural instability of the subject.

In some embodiments, the system is positioned on a left side of the subject's body, under the subject's armpit and to the left of the subject's nipple.

In some embodiments, each sensor further comprises a conditioning sub-module which can be powered up or powered down remotely to conserve a battery energy.

In some embodiments, the method further comprises measuring circulation with the ECG and comparing a measurement against a measurement made from two independent pulse wave sensors on each side of the subject's body to yield a possible difference in two PTT's with respect to an ECG "R" wave.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 3A is a side view of an embodiment of a hair-penetration electrode;

FIG. 3B is a side view of an embodiment of a hair penetrating electrode grid;

FIG. 3C is a top view of an embodiment of a hair penetrating electrode grid;

FIG. 5 depicts an embodiment of a single site sensing of electrocardiogram (ECG) and heart sounds with electrodes E1-E4

Figure 1A:
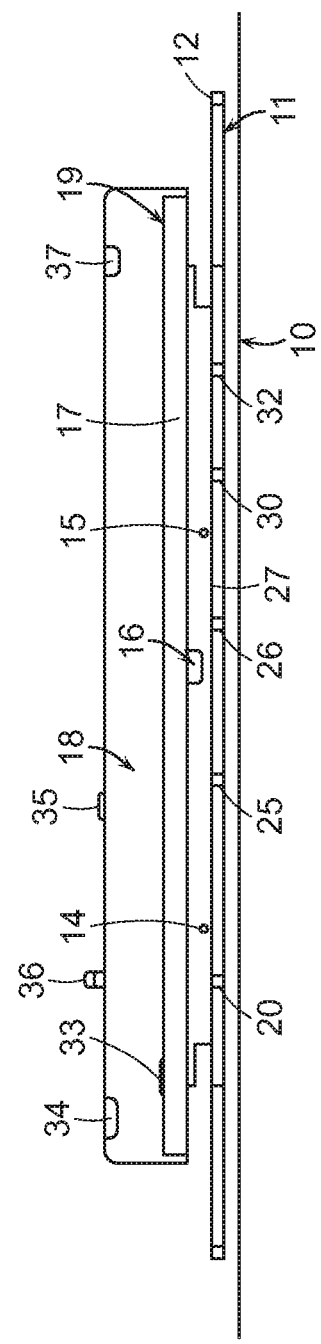
FIG. 1A depicts an embodiment of a monitor with a multisensory/stethoscope system-on-module.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

An embodiment of the present disclosure is a wearable, multi-parameter, real-time physiological monitoring platform or monitoring device which is intended for monitoring use—in or out-of-hospital. The device focuses on time-saving data reductions by combining an array of monitoring functions into a single device. The platform may send alerting signals to an attending physician transmitted upon significant physiological changes from personalized patient's baselines. Changes are based on remotely programmed high/low limit thresholds for each patient. The device significantly reduces data to be reviewed, so changes can be interpreted as early recognition signs of significant health deterioration events including life threatening events requiring immediate remedial response. In some embodiments the events comprise a heart rate above preprogrammed (or remotely programmed) threshold (Tachycardia) or a heart rate below a preprogrammed threshold (Bradycardia). The professional establishes the high/low limits for each individual case. Likewise, limit alerts are established for respiration, temperature, blood pressure trends, etc.

In some embodiments, the device is a patch. In some embodiments the device is a part of the clothing or is embedded in pillows and mattresses.

In some embodiments, the device is about the size of a credit-card and comprises a multi-sensor micro-monitor with a wireless sensing system-on-module (SOM). Using an advanced wireless IoT cloud technology, the monitor can be remotely programmed to detect and alert any of several events as changes from baseline. Some alert examples are: changes in heart rate and respiration rate, changes in heart rate variability, changes in blood pressure, changes in body temperature, changes in standing stability (fall prediction), changes in body position and physiology (fall detection), changes in oxygen saturation, changes in heart and lung sounds, changes in lung water, changes in mental stress, changes in sleep quality (mixed apnea and OSA detection), and/or changes in pacemaker activity. In some embodiments, there is a device which comprises a device or patch or any other form of a physiological telemonitoring device for users or others to apply and perform short term, triage, or long term self-monitoring.

The device may have several sensors and corresponding single to several monitored parameters. The device incorporates electronics to enable various monitoring parameters to be performed non-obtrusively, with a real-time wireless connectivity or data logging with off-line download. The monitored parameters may include one or more of ECG, ECG "R" wave, blood pressure pulse wave, pulse transit time (PTT) related to blood pressure trends, EMG and/or EEG (if head-worn), EMG True root mean square (RMS), respiration, body temperature, ambient temperature, stethoscope monitoring (e.g., heart and lung sounds), skin conductance or resistance as related to sweating and emotional responses, triaxial acceleration (enabling activity as well as body position monitoring), and skin vibrotactile and/or auditory alerting feedback.

In some embodiments, the device may include one or more of a microphone, a preamplifier/remote or locally programmable equalizer and earphone amplifier to enable the addition of a hearing aid capability, a "panic" or alert override button, a micro-camera, and/or a Trans Electric Neural Stimulator (TENS) unit.

In some embodiments, the device may include one or more algorithms for derived blood pressure trends via PTT, derived heart rate, heart rate variability (HRV) and heart rate trends, respiration abnormalities including apnea (central and obstructive) and snoring, remote programming of device power up from sleep mode, remote programming of High/Low limit alerts, and remote programming configuring and powering of sensing channels.

In some embodiments, the device incorporates a combination of innovative aspects to enable reliable operation. The innovative aspects may comprise the combination of sensing scheme, analog and digital signal processing algorithms, and IP protection embedded in the microcontroller. In some embodiments the device integrates user interfaces in the form of a vibrotactile transducer as well as remote, wireless audio-visual means.

In some embodiments, the device is a remote physiological monitor comprising a single user or disposable or semi-disposable body-worn unit. The device further comprises (a) a set of 3 or more contacting bio-signal electrodes, piezo-electric and/or optical sensors that sense the respiration, movements, and/or blood pressure pulse, (b) a means to attach the device to a body part by an adhesive, strap, clothing, as well as placement under a mattress or a pillow, or implanted under a patient's skin, (c) an electronics unit in discrete or system-on-chip form that contains the amplifiers, filters, analog-to-digital conversion, analog and digital signal conditioning algorithms, expert system multiparameter-based diagnostic algorithms, battery and power regulation, and (d) wireless means such as Bluetooth Low Energy with antenna.

In some embodiments, the piezo sensor (as demonstrated in FIG. 30) has a capacitance of greater than 100 nanofarads.

In some embodiments, the device further comprises ECG electrodes where the pulse transit time is derived as a function of an algorithm to yield PTT (the delay between the R wave and the pulse wave peaks) to enable tracking blood pressure changes.

In some embodiments, the device includes a vibrotactile skin vibrator for user's personal alerts. In some embodiments, a respiration waveform derived from the EMG or from the piezo, in conjunction with the stethoscope, an expert system enabled to detect and differentiate a central as well as an obstructive and a mixed apnea, a snore and a cough.

In some embodiments, the device can serve in broad applications and will include a variety of additional monitoring capabilities. The uniquely combined multiple parameters can offer more accurate diagnostic capabilities vs. monitors with limited parameters. The broad applications and capabilities may comprise (1) a consumer health state and sleep quality advisory screener, with no medical claims, (2) a regulated medical grade monitor that enables early recognition and remote alerting of impending life-threatening event, with remotely programmable high/low limit alerts, (3) a data logger for clinical studies, including in-home, in-hospital, post-operation follow-up, medication efficacy, mobile clinical studies and more, (4) a remote animal monitoring device—health and security, (5) a fitness trainer, (6) a stress management trainer, (7) a fall predictor/detector, (8) a hearing aid, (9) a TENS unit, (10) a cardiovascular monitor/analyzer, and (11) a cardio-respiratory monitor/analyzer.

In some embodiments, the device is configured to enable remote monitoring of nearly every parameter monitored in a hospital, and to generate an alerting signal transmitted locally and remotely to indicate any event, including but not limited to tachycardia, bradycardia, atrial fibrillation, apnea, hypoventilation, body turns, internal hemorrhage, falls, medication efficacy and compliance.

In some regulated medical applications, the device may further comprise a larger system comprising a Smartphone, tablet, PC or smart watch algorithms. The device may further comprise a wireless hub for integrating additional auxiliary sensing modules, e.g., multi-channel EEG/EMG/ECG, pulse oximetry, weight, and glucometers.

In some embodiments, the integration of auxiliary signals is performed via a Serial Peripheral Input (SPI) connector.

In some embodiments, the device can communicate with devices such as smart phones, smart watches, other wearable technologies (e.g., Google Glass), tablets or PC's, and can include advisory, data logging and life-threatening alerts. The device may monitor, detect and/or communicate information about (a) heart rate during fitness or cardiac rehabilitation exercise, (b) blood pressure changes from ECG and Pulse Wave PTT, (c) sleep apnea episodes including ECG heart rate and respiration, (d) early recognition of cardiac arrhythmias, tachycardia, bradycardia and arrest, (e) impedance cardiography/stroke volume, (f) sleep quality and sleep quality screening, (g) general well being, (h) early recognition of convulsions and epileptic seizures, (i) medication efficacy, (j) slips and falls, and/or (k) remote checkup information In some embodiments, the device comprises a skin and ambient temperature sensor as well as a skin conductance sensor using the bio-signal electrodes with supporting electronics and an expert system algorithm configured to identify hypothermia, fever, and cold sweat. In some embodiments the device further comprises a triaxial body position and impact sensor with supporting electronics and an expert system algorithm to detect a fall based on an impact followed by a physiological change to the user.

In some embodiments, the device further comprises a stethoscope (microphone and diaphragm) with supporting electronics to enable detection of a body sounds such as a heart sound, a lung sound, snoring, and/or coughing, with supporting expert system algorithms to identify a mixed apnea, including obstructive apnea, in conjunction with an expert system algorithm.

In some embodiments, the device further comprises a touch sensor for power activation upon a long press, and an alert transmission upon a short press. The device may further comprise a skin vibrotactile transducer to enable the user covertly sense an impending alert transmission and to abort an alerting transmission at will. In some embodiments, the device further comprises a coded tapping of the device to activate power and/or to override an alert transmission.

In some embodiments, the device comprises a strapless wireless ECG exercise heart rate monitor with a sensing device comprising a minimum of 2 adjacent electrodes, wherein the device is attached by an adhesive or other means to a left side of a body, under an armpit.

In some embodiments, the HR algorithm comprises a digital filter to minimize movement artifacts.

In some embodiments, the device further comprises a wireless monitoring system that includes local or remote display. In some embodiments, the device is attached to a right or a left side of a body in proximity to an armpit so that the device can simultaneously sense ECG, EMG respiration and body temperature. In some embodiments, the device further comprises an additional wireless pulse wave sensor which is attached to a body part and the PTT is derived from the time synchronization of two wireless elements and the delay between them.

In some embodiments, the electrodes are dry, not wet and do not need liquids or gels to function. In some embodiments, the dry electrodes have irregular surface to increase their effective area and make a galvanic skin contact in hairy areas on a body. In particular embodiments, the electrodes comprise an irregular, non-smooth surface to be made of any shape that points towards the skin while having no sharp edges, and configured to allow the skin to breath. In some embodiments the shape is an inverted pyramid. In some embodiments, the electrodes are made of a plastic coated with silver of 90-100% purity, where each electrode has a protruding pin or pins inserted to a holding printed circuit and held with solder or a conductive glue.

The device can be made in various geometries. In some embodiments, the device is a single printed circuit board that contains the sensors and the electronics as seen the exemplary embodiments of FIG. 38A and FIG. 38B.

In some embodiments, the device further comprises a skin-contacting stethoscope diaphragm which may contain three or more surface electrodes that monitor one or more parameters such as EMG, ECG, skin conductance or resistance, in addition to the stethoscope's heart/lung sounds. In some embodiments the diaphragm has an inner side which comprises a piezoelectric ink or other piezoelectric material configured to enable the monitoring of blood pressure pulse waveform and/or respiration waveform. In some embodiments, the device further comprises a pulse oximeter (as demonstrated in FIG. 27) provided the diaphragm is configured such that the optical characteristics are not compromised.

In some embodiments, the device further comprises an infrared sensor placed inside the stethoscope's diaphragm to monitor a skin temperature.

In some embodiments, the device further comprises an electronics board, the electronics board being disposable, semi disposable or single user reusable, with a battery that can be replaced or with a rechargeable battery that can be charged off-body using a charger or by an inductive means. In some embodiments, the electronics board comprises non-contact sensors/electronics. In some embodiments, the sensors/electronics may comprise a triaxial acceleration/position sensor.

In some embodiments, the electronics board further comprises an Electronics Unit (EU) that comprises signal conditioning elements. The signal conditional elements may include (a) amplifiers, filters, and analog multiplexers, (b) common ECG/EMG electrodes and/or common ECG/EMU/Skin resistance or conductance or impedance electrodes, (c) an ECG filter/amplifier, (d) an ECG "R" wave filter, (e) an SPI with auxiliary I/O (inputs/outputs) such as for a glucometer, a 3-12 lead ECG, a pulse oximeter, a weight monitor, or a lung water, (f) an analog-to-digital converter (A/D), a microcontroller, a wireless transceiver, or all-in-one MPU/BLE, (g) a skin vibrator, (h) an on/off mechanism, (i) batteries, (j) a battery power management, (k) a stethoscope microphone, (l) an optional hearing aid microphone, (m) an optional earphone amplifier and output connector, (n) ambient temperature sensor, (o) an EMG/ECG/EEG, (p), an ECG, (q) a skin conductance or a skin resistance measure, (r) a blood pressure pulse waveform sensor, (s) a respiration waveform sensor, (t) a measure of skin temperature, (u) a measure of ambient temperature, (v) a measure of triaxial acceleration, (w) a skin vibrotactile alerting transducer, (x) a "panic" or alert override button, and/or (y) a TENS.

In some embodiments, the device comprises a SOM (System-on-Module) telemonitor, the telemonitor comprising (1) a non-optical, zero power piezo element employed as a sensor for one or more functions such as pulse, respiration, impact, volitional coded finger-tapping message, and movements; (2) a piezo element configured to meet low frequency sensing capabilities by having a capacitance greater than 100 nanofarads; (3) multi-function capabilities embedded in an electrode array of three electrodes where the electrodes concurrently monitor ECG and EMG, deriving both a heart rate and a respiration rate; (4) a pulse oximeter embedded inside a transparent or semi-transparent stethoscope membrane, where the piezo element is also packaged inside the stethoscope diaphragm (membrane), wherein the membrane is deposited with piezoelectric ink to enable a stethoscope as well as other capabilities and the ink is transparent or semi-transparent in a given area to enable the pulse oximeter; (5) a remotely-controlled powering up specific channels to help conserve a battery energy; and/or (6) a remotely-controlled set-up of alert criteria with high/low thresholds.

Table 1 (below) demonstrates embodiments of the device with further placement options and benefits of each placement.

TABLE 1

| Body Placement Options | | |
|---|---|---|
| Example Placement | Example monitored Parameters | Example derived parameters |
| Left Torso (adhesive patch, strap, under clothing) | As described herein | As described herein |
| Ankle, including over pants | Blood pressure pulse wave, activity, position | Resting heart rate, restless leg syndrome, sleep quality |
| Wrist | EMG, Blood pressure pulse wave, activity, position, skin resistance/conductance, peripheral temperature | Alertness, resting heart rate, resting respiration, sleep quality, mental stress |
| Under mattress or seat | Blood pressure pulse wave, respiration, activity, snoring sounds (stethoscope) | Resting heart rate, restless leg syndrome, sleep quality, asthmatic breathing, snoring, epileptic fits and convulsions |
| Forehead | EEG, EOG, Blood pressure pulse wave, activity, position, O2, Skin resistance/conductance, | Sleep quality, respiration (pulse wave derivation), epileptic fits and convulsions |

TABLE 1-continued

Body Placement Options

| Example Placement | Example monitored Parameters | Example derived parameters |
|---|---|---|
| Neck | ECG, Blood pressure pulse wave, resting respiration, O2, activity, position, optional other available channels in the full monitor | Triage signs of life |
| Abdomen | EMG and Pulse wave | Fetal heart rate and uterine contractions |

In some embodiments, the device comprises a SOM (System-on-Module) telemonitor, the telemonitor comprising (1) a non-optical, zero power piezo element employed as a sensor for one or more functions such as pulse, respiration, impact, volitional coded finger-tapping message, and movements; (2) a piezo element configured to meet low frequency sensing capabilities by having a capacitance greater than 100 nanofarads; (3) multi-function capabilities embedded in an electrode array of three electrodes where the electrodes concurrently monitor ECG and EMG, deriving both a heart rate and a respiration rate; (4) a pulse oximeter embedded inside a transparent or semi-transparent stethoscope membrane, where the piezo element is also packaged inside the stethoscope diaphragm (membrane), wherein the membrane is deposited with piezoelectric ink to enable a stethoscope as well as other capabilities and the ink is transparent or semi-transparent in a given area to enable the pulse oximeter; (5) a remotely-controlled powering up specific channels to help conserve a battery energy; and/or (6) a remotely-controlled set-up of alert criteria with high/low thresholds. In some embodiments, the membrane further includes an infrared body surface temperature sensor. In some embodiments the membrane also comprises printed conductive ECG/EMG bioelectrodes. In some embodiments the monitor is placed on an upper portion of a forehead to monitor EOG and EEG in addition to pulse. In some embodiments, bioelectrodes monitor bioimpedance as well, enabling lung water to be tracked. In some embodiments. The electrodes have irregular surfaces configured to penetrate hair skin.

In some embodiments, the device further comprises expert system algorithms. The algorithms may be a respiration abnormalities algorithm including differentiation between central and obstructive apnea and snoring and combining respiration with lung sound sensing, a fall prediction algorithms, an internal bleeding identification algorithm, a dehydration/hyperthermia identification algorithm, an algorithm for retrieving emotional startle response from body sweat change, an algorithm for a circulatory monitoring scheme using dual pulse sensors, derived blood pressure trends via a pulse transit time (PTT) algorithm using the ECG together with a pulse wave sensing at the monitoring device. Derived heart rate, heart rate variability (HRV) and heart rate trends together with an artifact removal algorithm can incorporate a digital filter. In some embodiments, the algorithms may further comprise a respiration abnormalities algorithm including differentiation between central and obstructive apnea and snoring which may combine respiration and lung sound sensing, a fall prediction algorithms, a fall identification algorithm, an internal bleeding identification algorithm, a dehydration/hyperthermia identification algorithm, an algorithm for retrieving emotional startle response from body sweat change, and an algorithm for a circulatory monitoring scheme using dual pulse sensors, an algorithm for detecting and defining the accuracy of the body temperature by calculating the changes of the ambient temperature and its influence on the body temperature.

In some embodiments the device further comprises a silent alert to activate a skin vibrotactile transducer for communicating a subject's information or medication-taking reminder (scheduled or contingent upon a change in a physiological parameter such as heart rate, blood pressure, asthmatic wheezing, etc.). In some embodiments the device further comprises a multiple channel expert system which enables remote service provider to activate a life-saving injection. In some embodiments the device further comprises a monitor-embedded microphone activated upon an alerting event to enable hearing the patient at a remote service center, wherein a voice microphone can double as a through-clothing hearing aid with a remote hearing correction programming based on hearing lab tests and earphone output.

In some embodiments, the monitor has no battery and brief check-up transmissions are enabled by first tapping an energy harvesting element inside the monitor.

In some embodiments, the device further comprises a talking fitness application combining heart rate and music, as well as a swimmer's version combining heart rate, music and lap counting.

In some embodiments, the device comprises a monitoring application configured to generate a reliable differentiation between central apnea and obstructive sleep apnea (OSA). Combined sensors in a micro monitor and its intercostal body position enable a piezoelectric sensor sensitive to both pulse and respiration signals, where such respiration sensing has a poor low frequency response (AC response, or a differentiation of the signal due to high-pass filter characteristics). The piezoelectric sensor is only useful in normal respiration rates and hyperventilation (tachypnea). During OSA, the sensor may misinterpret the ineffective chest movements, thus being useful during central apnea episodes. During very low respiration rates or very shallow breathing, such sensor may interpret the person as not breathing at all. In order to reliably identify OSA and shallow breathing, the device further comprises two sensors: a) an EMG (using same electrodes as the ECG channel), sensitive to intercostal muscle activity down to a DC response, and b) a lung sounds stethoscope (forming an expert system of multiparameters). The presence of the piezo sensor respiration merely confirms that the user is alive. The stethoscope adds the discrimination of no air passage from the lungs together with ineffective piezo respiration signals to identify an obstructive breathing event. The EMG adds a majority decision capability to further enhance reliability of accurate respiratory states identification. The EMG and the stethoscope are also sensitive to the gasp that follows an obstruction and snoring.

In some embodiments, an apparatus for real-time monitoring of a subject's physiological condition comprising a micro-monitor with a wireless sensing system-on-module (SOM), the monitor being remotely programmable to detect one or more conditions in a subject by monitoring one or more parameters associated with the conditions and comparing any monitored parameter to a baseline measurement of the monitored parameter from the subject; a plurality of sensors, each sensor corresponding to a monitored parameter and connected to the micro-monitor to convey measurements of all monitored parameters; the sensors comprising a pulse waveform sensor, an electrocardiogram (ECG) sensor, and a blood pressure trending algorithm which uses a non-optical pulse sensor with the ECG to derive the PTT; a wireless communications module capable of communicating with a wireless technology, wherein the module can send an alert signal to the subject or an attending physician, the alert being transmitted to the subject or the physician upon the monitor detecting a significant physiological change in a measured parameter as compared to the subject's baseline measurement; a fall detection algorithm incorporating a startle response monitoring function; a fall prediction algorithm incorporating a Lissajous pattern analysis of body sway to predict falls using postural stability deviations from baseline; and an automatic distress activated microphone.

Referring now to the figures, FIG. 1A depicts a multisensor/stethoscope system-on-module. The sensor module 18 touches the body 10 and is held by a double sided peel-off adhesive 11, 12. A piezoelectric strip or any other shape as well as optional deposited piezoelectric material 14 are integrated in an inside of the stethoscope diaphragm 15 or elsewhere in the module 18. A microphone 16 with a frequency response exceeding the bandwidth of, e.g., 25-2000 Hz completes the stethoscope part with diaphragm 15.

Still referring to FIG. 1A, the piezoelectric material upon the diaphragm 15, or elsewhere in the module 18, extends a useful acoustic bandwidth to below 0.05 Hz, enabling the monitoring of a respiratory effort waveform, a blood pressure waveform, and gross movements and activity. Such frequencies are below the audible frequencies and thus are not audibly detectable otherwise.

Together with ECG pads, a pulse wave enables a measurement of blood pressure trends in a system-on-module (SOM) 18 (see also FIG. 37) via a PTT. ECG together with the stethoscope heart sounds, with or without the additional parameters, can offer unique diagnostic capabilities, especially out-of-hospital.

The microphone 16 is mounted on a printed circuit board (PCB) 17 where electronic components module 35 and batteries 19 are mounted and covered by a device cover 36 that incorporates a battery access 36 for replacing non-rechargeable batteries 19. The PCB 17 may further incorporate more sensors that do not need to contact the skin, including an acceleration sensor 33.

In some embodiments, a microphone 34 can be incorporated to the SOM 18 (see also FIG. 37) which uses the SOM's battery 19, amplifiers (see also FIG. 29), programmable filters (see also FIG. 29) and other circuitry to enable a hearing aid function to be implemented with output 35 to an earphone (not pictured). Some microphones 34 can be programmed to automatically switch into listening and transmitting mode upon sensing an alarm condition.

The diaphragm 15 has several sensors embedded in the skin-contacting side. It may contain strips of electrodes 20, 25, 26, 27, 30, 32 as well as a skin temperature sensor 90 as shown in FIG. 1A. In essence, the diaphragm 15 may also be a disposable element of the SOM. The conductive electrodes 20, 25, 26, 27, 30, 32 are dry, but in some embodiments they may be covered with disposable, customized peel-off array of conductive solid gel, potentially enabling better performance during exercise and potentially providing additionally conductivity between the electrodes 20, 25, 26, 27, 30, 32 and the skin.

In some embodiments, the earphone may add another dimension as a talking monitor, as in exercise heart rate training and for rehabilitation.

In some embodiments, referring to FIG. 1A, a micro-camera 36 may be added. A user may employ a mirror to enable transmitting the body location of the SOM to a service center, for example in the case that a monitoring problem is experienced. An optional ambient temperature sensor 37 is available.

Figure 1B:
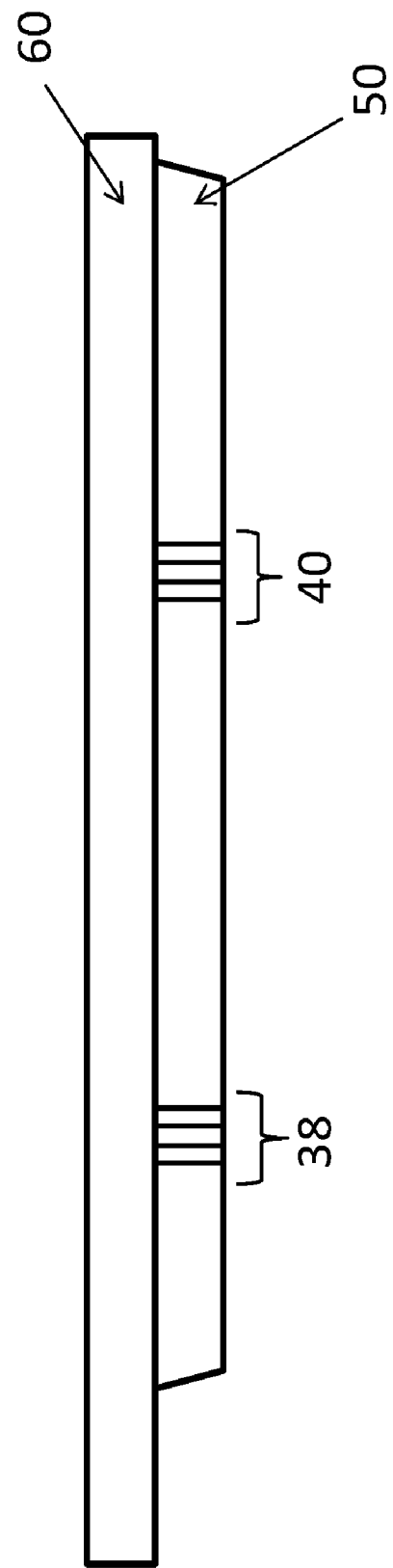
FIG. 1B depicts an embodiment of a via-free sensor wiring.

FIG. 1B shows the via-free wiring of the SOM sensors. The electrodes and the skin temperature sensor contacting the diaphragm are connected to the PCB 60 without using via holes that may corrode with body sweat. Instead, conductor groups 38, 40 are printed upon the diaphragm 50 and isolated by non-conductive coating.

Figure 28:
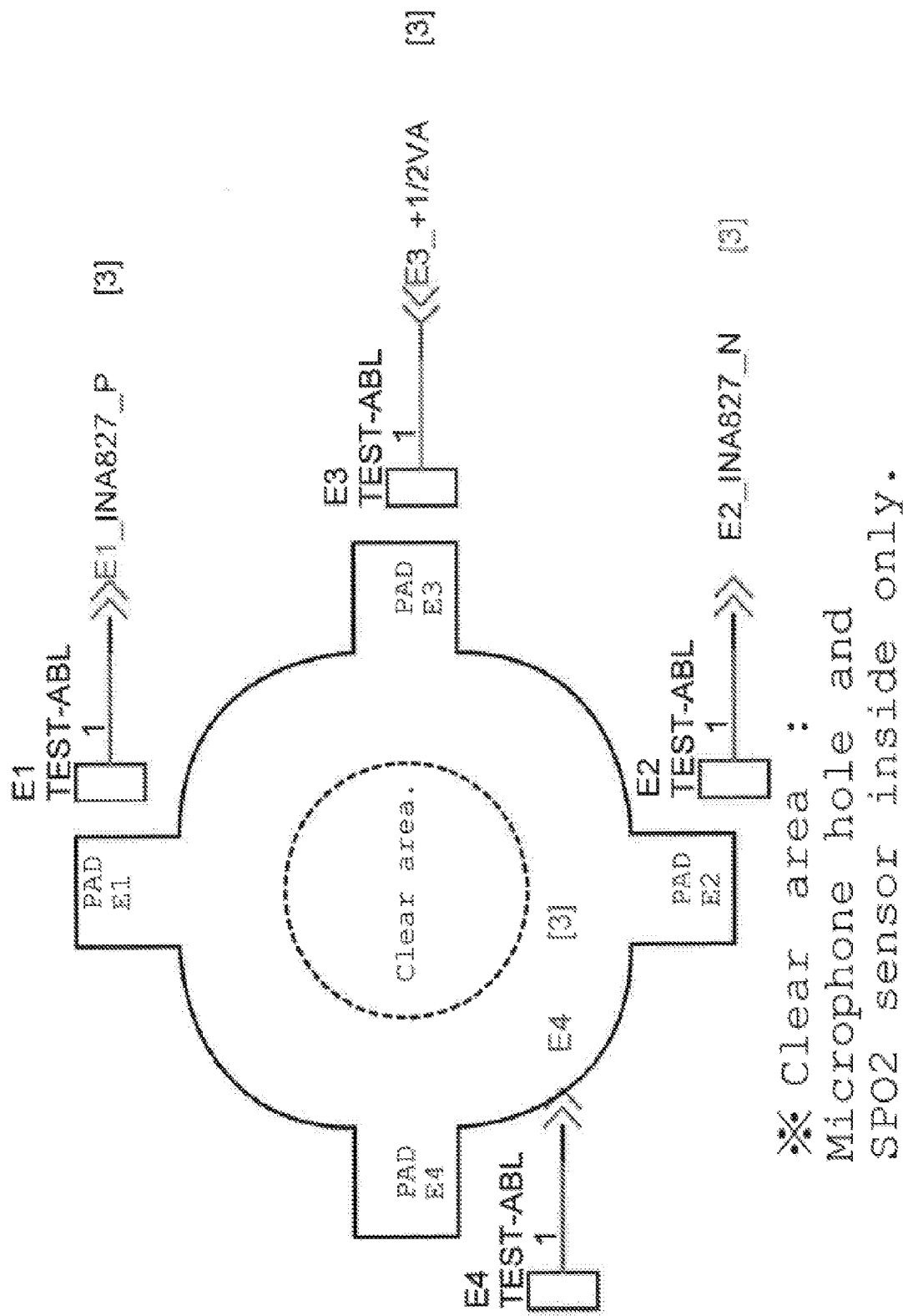
FIG. 28 illustrates an embodiment of 4 skin electrode contacts for concurrent ECG, EMG and Skin conductance or resistance monitoring.

Referring to FIG. 28, in some embodiments there are 4 skin electrode contacts, where E1 and E2 differentially pickup both ECG and EMG, E3 serves as the common electrode and E4 monitors skin conductance as well as removal of the device from the body.

In some embodiments, electrode contacts 75, 80, 91, 92, 93, 94 simultaneously measure the following: ECG (one lead, enabling the monitoring of arthythmias and trending the blood pressure via PTT); EMG (enabling the monitoring of respiration effort, asthmatic spasms, epileptic convulsions, coughing); and skin resistance, conductance or impedance). In some embodiments, two of the electrodes serve to reduce electromagnetic interference noise in the bioelectric ECG and EMG signals.

In some embodiments, SOM can be placed in all other body locations (torso, limbs, neck, head) to obtain more or different data. Moreover moving the stethoscope offers more heart/lung diagnostic capabilities. Furthermore, the SOM can be placed in pillows, under or in-mattress, under or in chair mats, on clothing, over bandages, in helmets, in headbands, swim gear including caps, vests and goggles, hats, splints and more. The SOM can be placed on a floor near a bed, for example, to detect fall impacts, bed exits, bed turns and more. Continuous stethoscope monitoring can take place in fetal heartbeat monitoring at home. The other parameters can help achieve a more accurate diagnosis. In some embodiments, the SOM can be made of discrete components as well as from one or more SOCs (System-on-Chip) to further reduce the size and production bill-of-materials (BOM) cost of the SOM.

Figure 2:
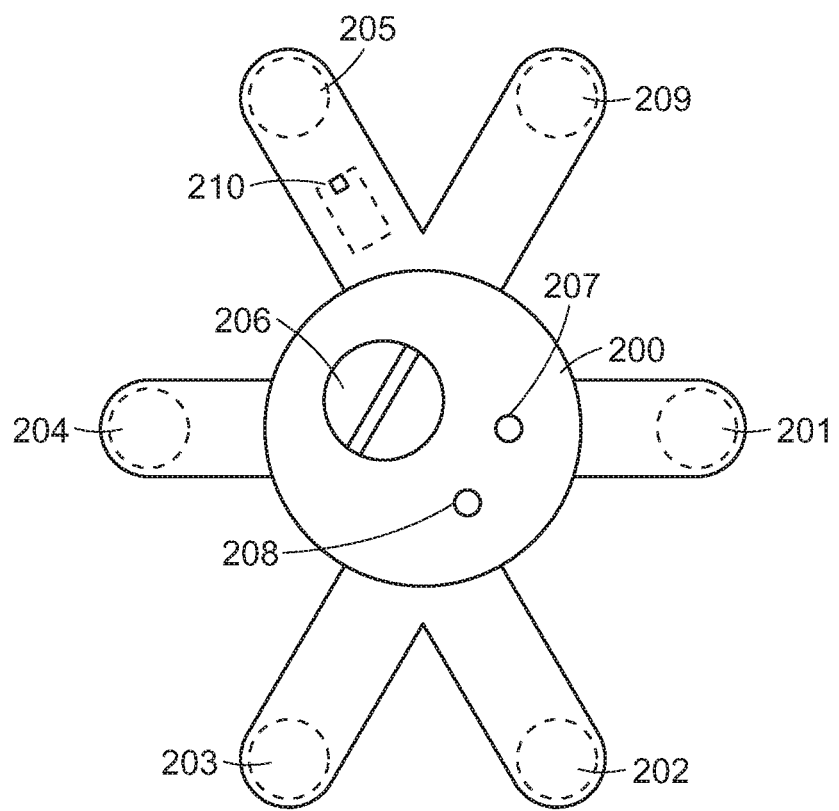
FIG. 2 is a top view of an example embodiment of the device.

FIG. 2 is a view of another embodiment of the sensor elements of the telemonitoring patch 200. The sensor comprises adhesive peel-offs 201, 202, 203, 204, 205, 209 containing electrode contacts. In one embodiment, the number of electrodes can vary from 3 to 6 or more. An optional hearing aid microphone 207 and an optional micro-camera (pointed at a mirror to view the patient) or ambient temperature sensor 208 are shown on top of a monitor 200. A battery cover 206 is included and can be of various designs (for example, having a humidity seal). An inductive charging option is not shown. There is an optional skin temperature sensor 210. The sensor 210 and the electrodes 201, 202, 203, 204, 205, 209 can be disposable. The electrode complex, while Ag/AgCl is most common, can be single subject reusable sintered electrodes, and a solid gel array can form an alternative adhesion means.

FIG. 3A, FIG. 3B and FIG. 3C show hair-penetrating electrodes having a design of dry (gel-free) electrodes that penetrate hair on the scalp, torso and limbs. In addition, such design enables the skin to breath. FIG. 3A is a side view of an embodiment of a hair-penetration electrode. FIG. 3B is a side view of an embodiment of a hair penetrating electrode grid. FIG. 3C is a top view of an embodiment of a hair penetrating electrode grid. A basic electrode carrier 220 is flexible, with pyramid 226 or similar shaped electrode contacts 221 with a blunt contact tip 224 or 225 shown as examples. Such multi-contact assembly connects one to any number of electrode contacts together with a single output wire 222. Such assembly can be employed dry or with gel, use a nearly pure silver coating on plastic elements, or alternatively be coated with Ag/AgCl. In another embodiment, the electrode can be sintered (ground and compressed) Ag/AgCl to offer long-term use for a single user. In some embodiments, the pyramid shaped electrode is hollow in whole or in part for enabling a gel to be squeezed out of one or more holes to improve a skin contact. In some embodiments, the pyramid electrode comprises sharp contacts that are covered by an array of solid gel peel off accessory, thus pressed with greater pressure into the skin while reducing contact impedance.

Figure 4B:
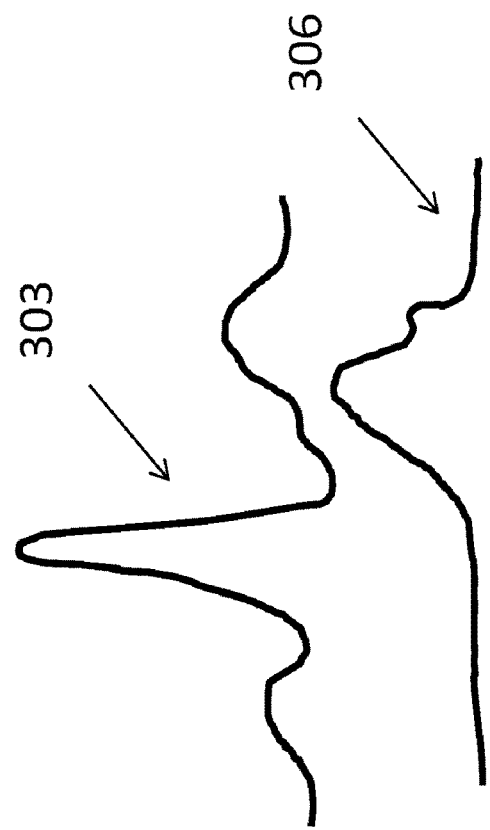
FIG. 4B depicts an embodiment of a single site blood pressure trending scheme.
Figure 4A:
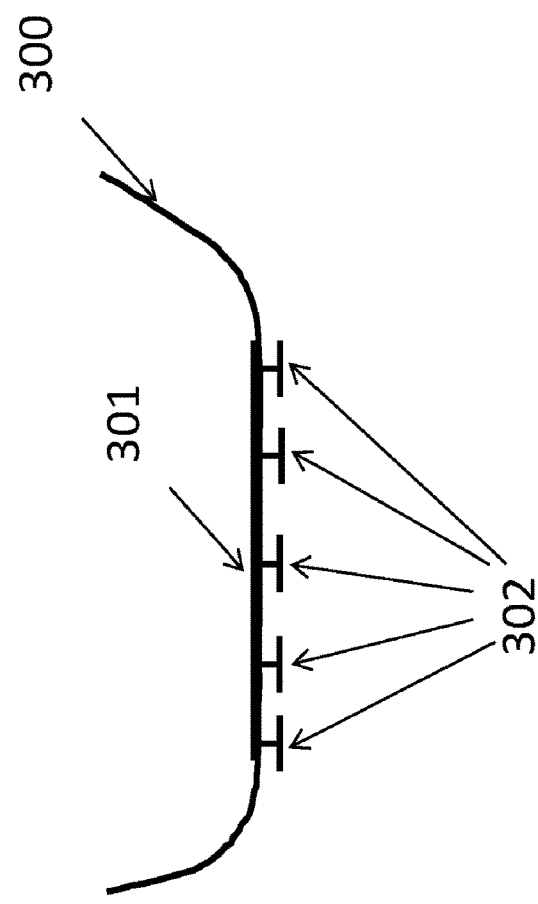
FIG. 4A depicts a view of a device with a piezo material deposited on a stethoscope diaphragm.

FIG. 4B depicts blood pressure trending by PTT with PTT from a peak ECG "R" wave 303 to a peak blood pressure pulse wave 304 The pulse may be obtained by a piezo material deposited on the stethoscope 300 diaphragm 301 as seen in FIG. 4A. The non-optic pulse waveform sensor needs no direct contact with the skin and is immune to skin pigment and stray light that affect optical sensing, and it consumes zero power.

Referring now to FIG. 5, depicted is a single site sensing 310 of ECG E3 314 and E4 317 electrodes) and heart sounds (as well as lung sounds) by a stethoscope diaphragm 310 and microphone 311 with an amplifier 312 on the PCB 313. In this embodiment, there is no skin conductance or resistance electrode. Of course, a fifth electrode may be added to implement the latter. To assure a high quality ECG "R" wave, the backbone of many algorithms, the ECG electrodes which also monitor the EMG are augmented by two additional electrodes E1 315, E2 316 (skin contacts) that act as a "right-leg-drive" using the amplifier 318. This scheme is needed to reduce effects of electromagnetic interference. The subject or user at home may be close to electrical appliances, thus the electromagnetic environment is unknown, unlike a hospital setting. Such a scheme drives the human body's common mode voltage to near zero. The ECG amplifier 319 (also pre-amplifying the EMG) is then subtracting (rejecting) a common mode interference signal that may be greater than the biological signals by orders of magnitude, resulting in a clinical grade ECG (and simultaneously EMG) signal quality.

Figure 6:
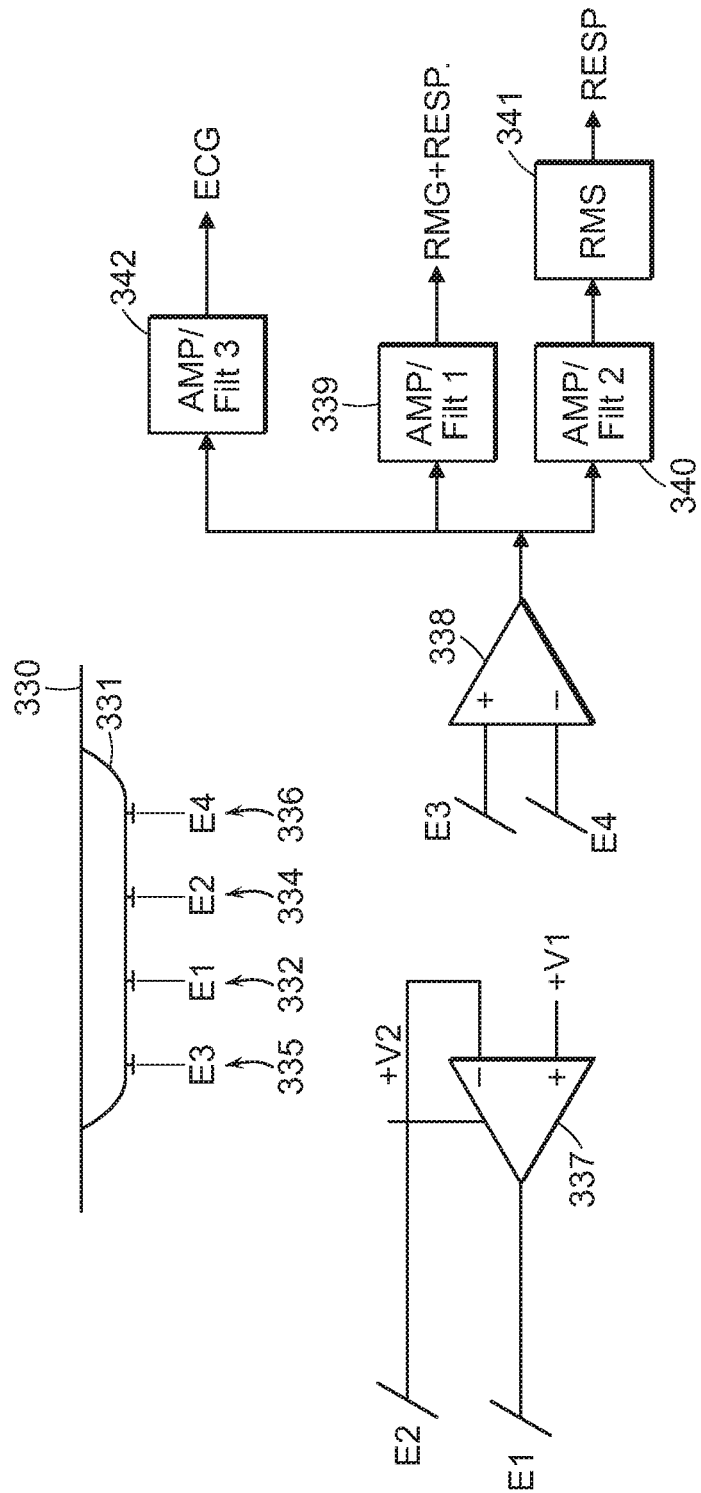
FIG. 6 depicts an embodiment of a single site sensing of ECG, electromyogram (EMG), skin conductance (or resistance) and respiration using 4 electrodes.

FIG. 6 depicts a single site sensing of ECG, EMG and respiration using only four electrodes (and in some embodiments as few as three electrodes). FIG. 6 adds a bank of filters to the ECG/EMG amplifier 338 as shown in FIG. 5 as 319. The respiratory effort is a neuromuscular modulation of the EMG at the chosen site (a left body side, where ECG is also present), and it is derived by amplifier/filter 340 and RMS (Root Mean Square) processing 341 (preferably True RMS) using analog or software means. The composite EMG/respiration signal is amplified separately by amplifier/filter 339. The ECG is retrieved by the amplifier/filter 342. The clear area shown in FIG. 28 in another embodiment incorporates the stethoscope diaphragm, and under it the SPO2 sensor and the stethoscope microphone. In an example embodiment, an IR temperature sensor is packaged under the stethoscope diaphragm, else the temperature sensor is placed near one of the electrode pads E1, E2, E3 and E4. FIG. 6 depicts a stethoscope membrane 331, whose other side is embedded with the piezoelectric pulse/respiration sensor 330. Amplifier 337 is the common mode driver of E1, E2 electrodes. Amplifier 338 simultaneously pre-amplifies ECG and EMG signals (the latter which is modulated by a neuromuscular respiratory effort), amplifier 339 filters the EMG and respiration signals), amplifier 340 filters the respiration component of the EMG signal), and amplifier 342 filters and amplifies only the ECG signal). Using RMS or True RMS converted 341, hardware or software derives the respiration signal from the ECG. Another respiration signal is available from the piezoelectric sensor embedded inside the stethoscope's membrane 331. Such redundancy ensures respiration sensing reliability. The stethoscope offers another dimension and diagnostic capabilities in respiration monitoring in an entirely different domain (e.g., audio). A cough is sensed both by the stethoscope and by the EMG. It can be seen by the acceleration sensors as well, but the origin is better defined by the previous two parameters.

Figure 7:
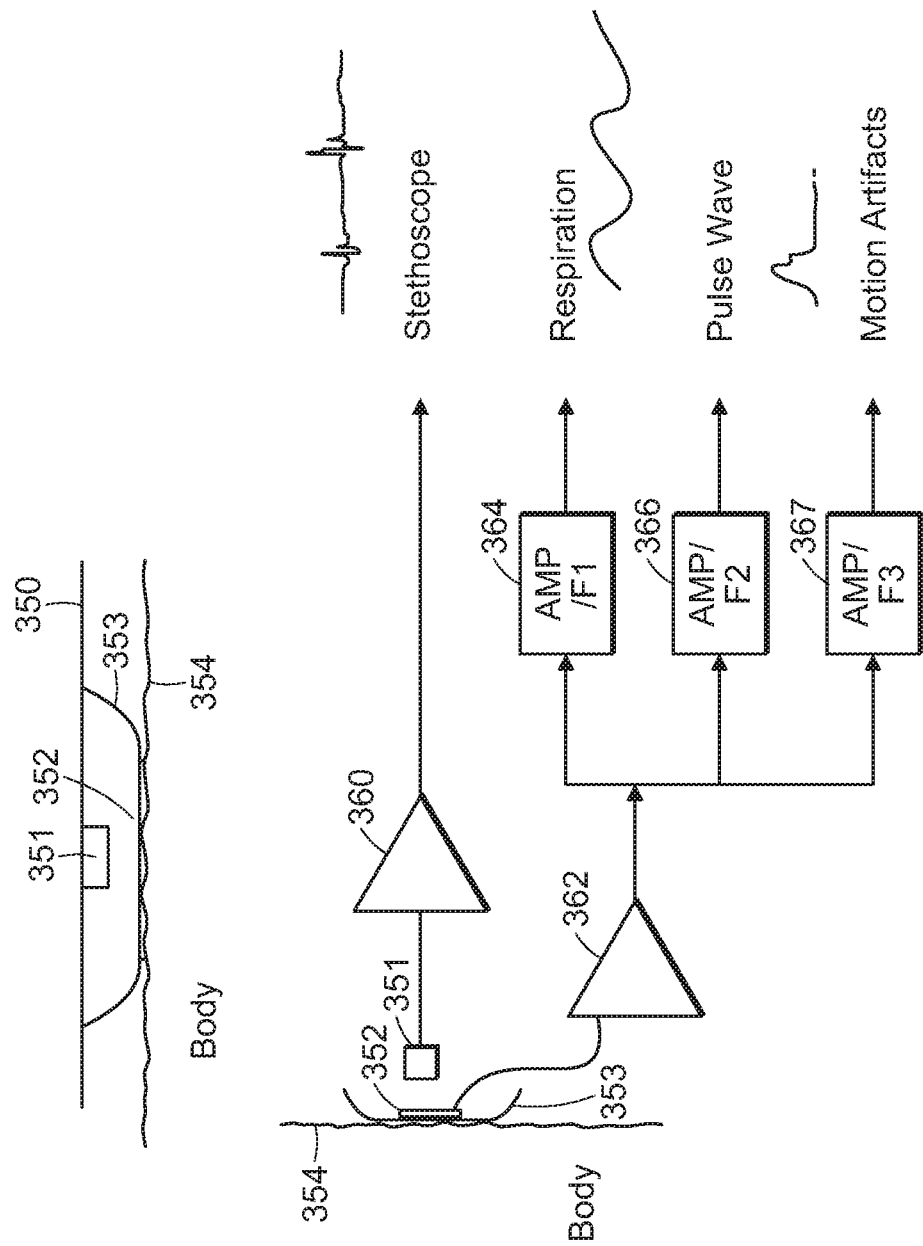
FIG. 7 depicts an embodiment of a single site sensor for simultaneous lung/heart sounds (stethoscope) together with zero energy, single sensor respiration, motion artifacts and blood pressure pulse wave monitoring.

FIG. 7 depicts a single site zero energy sensor 352 for simultaneous respiration 364, motion artifacts 367 and blood pressure pulse wave 366 monitoring by an amplifier/filter signal separation. In one embodiment, the piezoelectric sensor 352 is not in direct contact with the skin, whose signals are amplified by an amplifier 362. A skin interface is maintained with the membrane of the embedded stethoscope 353. Also shown is the microphone 351 and preamplifier 360 of heart, respiration, snoring, wheezing and coughing sounds stethoscope.

Figure 8:
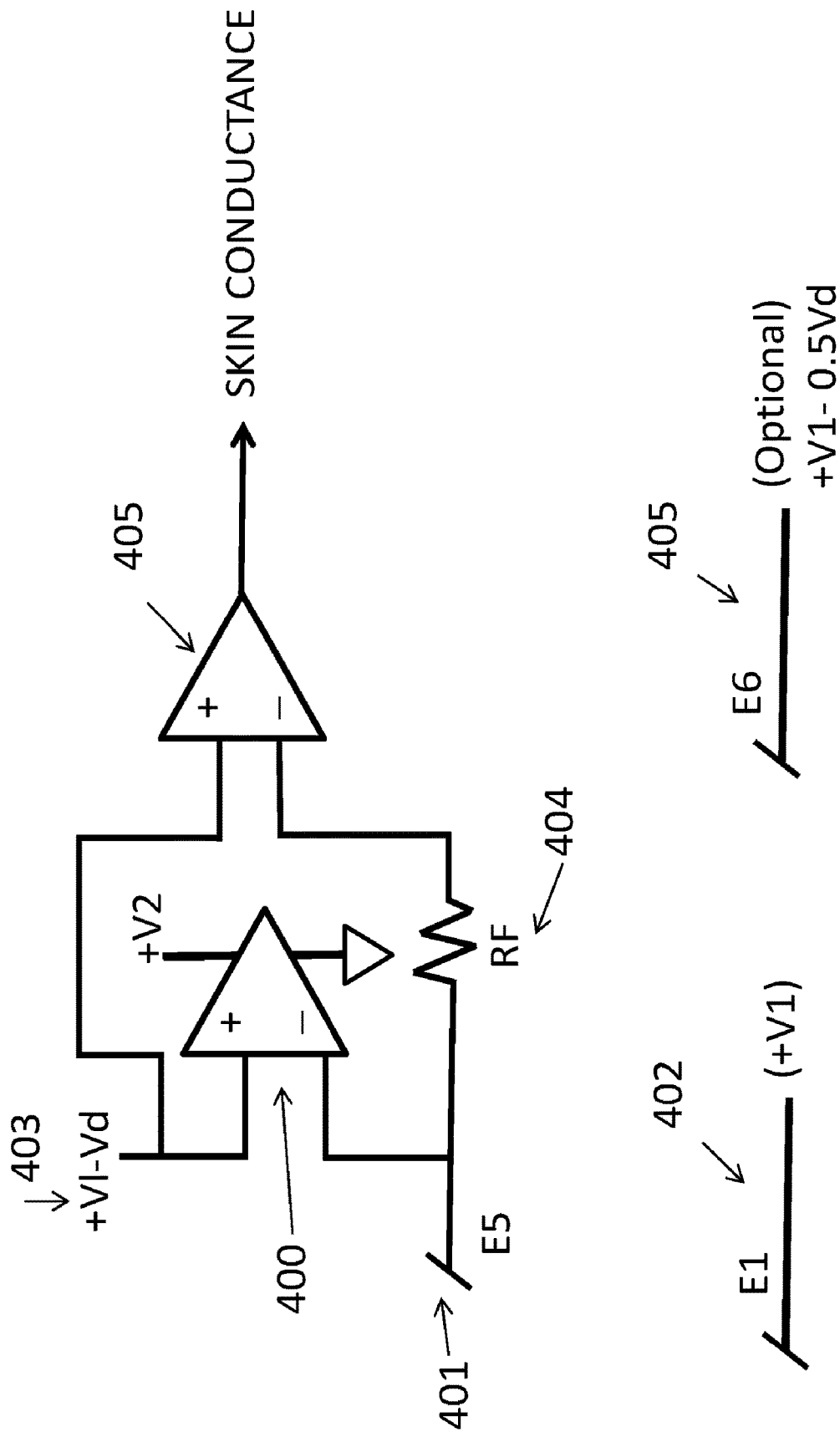
FIG. 8 depicts one embodiment of a skin conductance channel employing additional electrodes.

FIG. 8 depicts an embodiment of operational amplifiers depicted in a feedback configuration to provide a skin conductance channel using amplifiers 400, 405. Electrode E1 402 is shared with the ECG/EMG reference. The channel has two functions: monitoring of sweating level and, measured by another circuit, monitoring of emotional response. Optional electrode E6 405, together with a voltage drive 403, enhances the non-interference of this channel with the low-level signal biopotential channels ECG and EMG. Together with the respiration channel, covert stress alert and management is made possible.

Figure 9:
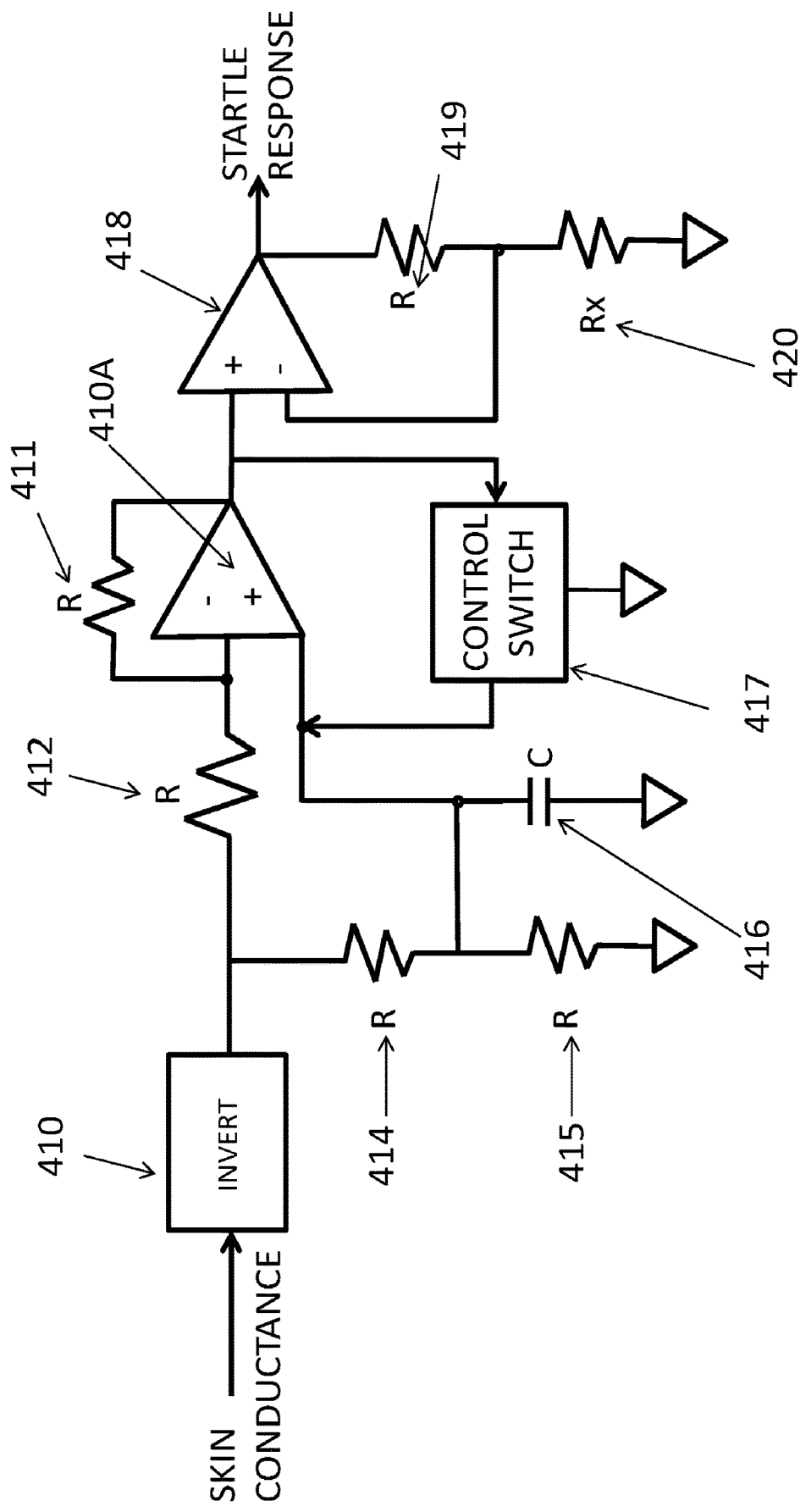
FIG. 9 illustrates an embodiment of a circuit to magnify the low-level skin conductance changes with emotion (e.g., startle)

FIG. 9 depicts an embodiment of a circuit to magnify low-level skin conductance changes with emotion (due to placement considerations far from emotionally-responsive sweat pores). A circuit 410 inverts the skin conductance from amplifier 405; amplifier 410A follows as AC differential amplifier with amplifier 418 as gain amplifier. The passive components (e.g., resistors) 411, 412, 414, 415, 416, 419, 420 and capacitor 416 produce an auto-zero signal for the slowly varying baseline and amplify only desired changes clamped to a zero level. In addition, the circuit switches a capacitor 416 discharging scheme to ensure a fast recovery to signal changes. This enables detection of a "startle response" as part of an intelligent fall detection module.

Figure 10:
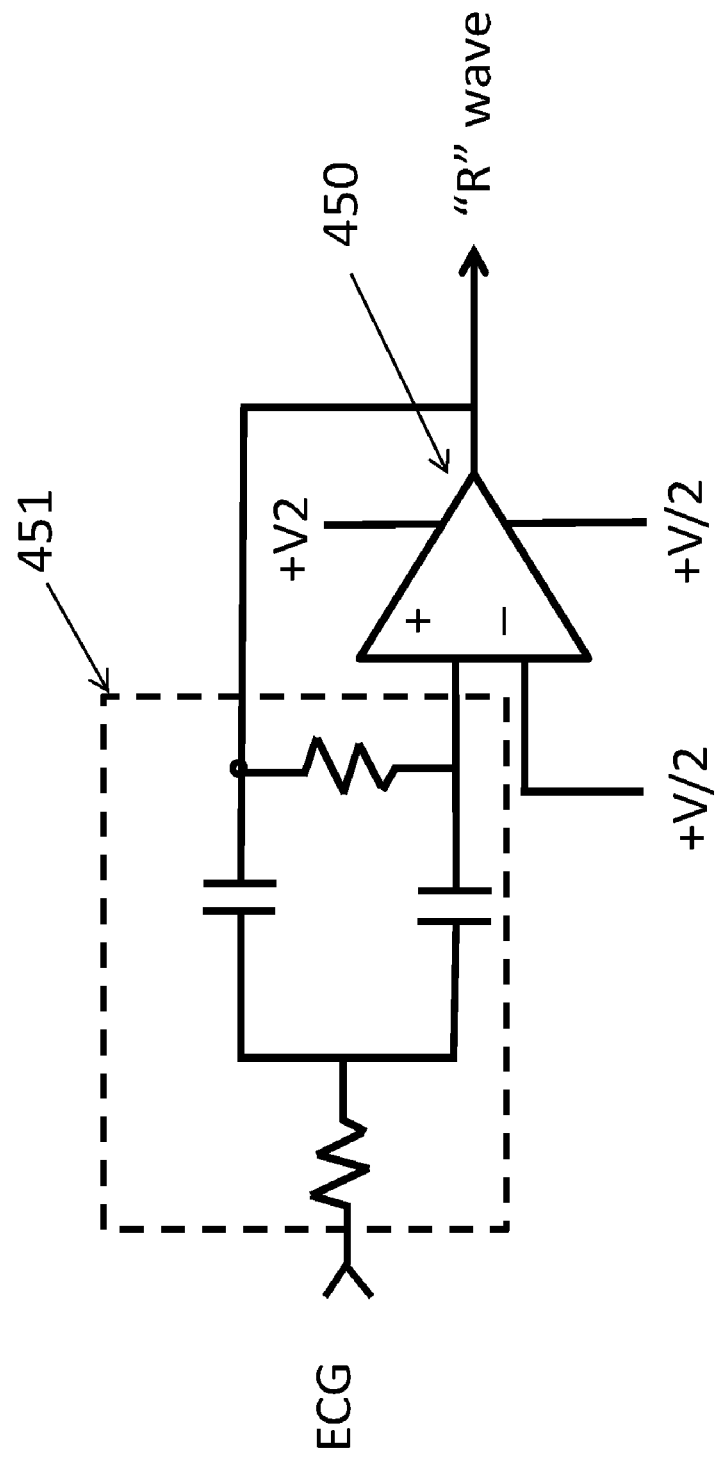
FIG. 10 depicts an embodiment of a non-linear ECG "R" detector.

FIG. 10 depicts an embodiment of an ECG "R" detector 450. As shown, the bandpass filter detector includes an op-amp, resistors, and capacitors to enable ambulatory heart rate monitoring.

Figure 11:
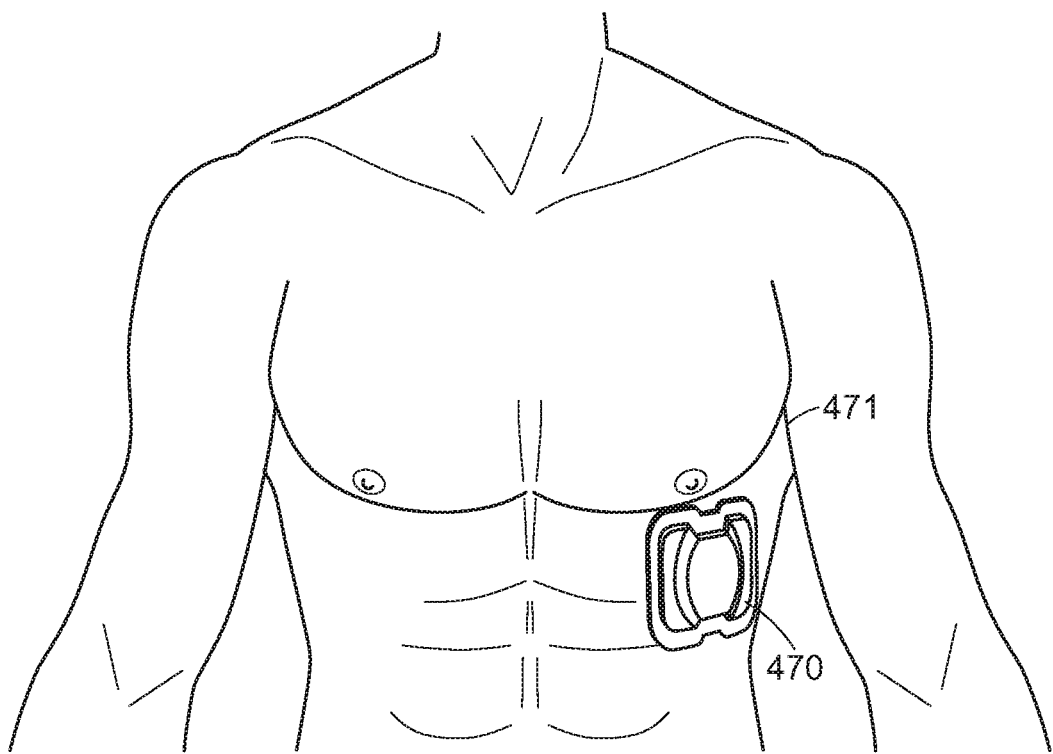
FIG. 11 depicts an embodiment of a monitor placed at a left side of a body.

Referencing FIG. 11, depicted is an embodiment of the device 470 placed at a left side of a body, approximately under an armpit 471 and left of a nipple. This unique "strategic" placement enables the concurrent monitoring of ECG, EMG, respiration, blood pressure trending, body position and good body temperature estimation. It is close to the heart yet at a site with little or no hair.

Figure 12:
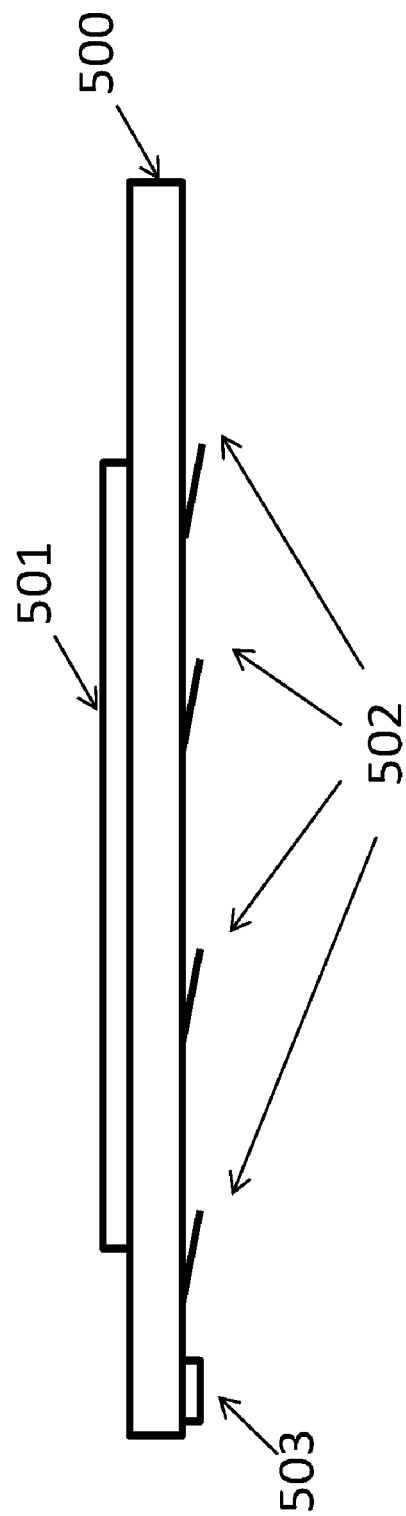
FIG. 12 depicts an embodiment of a monitor without a stethoscope.

FIG. 12 depicts an embodiment of the device without a stethoscope. A piezo element 501 is connected to one side of a printed circuit (PCB) 500 and electrodes 502 are printed on another side of the PCB. A skin temperature sensor 503 is also connected to the PCB.

Figure 13:
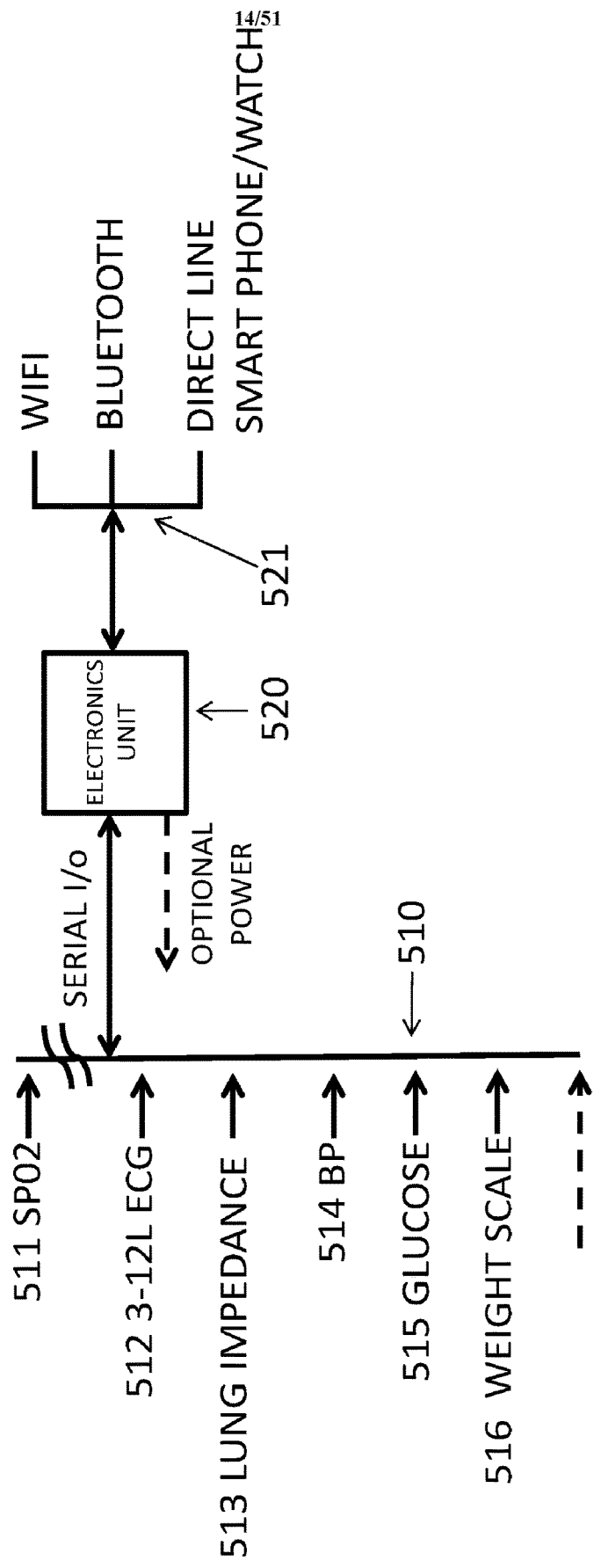
FIG. 13 illustrates a method of connecting external monitoring modules via a serial port input to a main telemonitor.

FIG. 13 depicts connecting a monitor electronics unit 520 to other auxiliary monitoring modules 511-516 via serial port inputs of a main telemonitor. Acting as a hub 510, the auxiliary modules' outputs are integrated with a single communications channel 521. In this manner, the telemonitor can replace hospital grade monitors costing orders of magnitudes more without the body-covered sensors and obtrusive cables. Auxiliary inputs include 3-12 L ECG, Glucometer, lung impedance, glucose, blood pressure, weight scale, and any other serial I/O auxiliary monitor.

Figure 14:
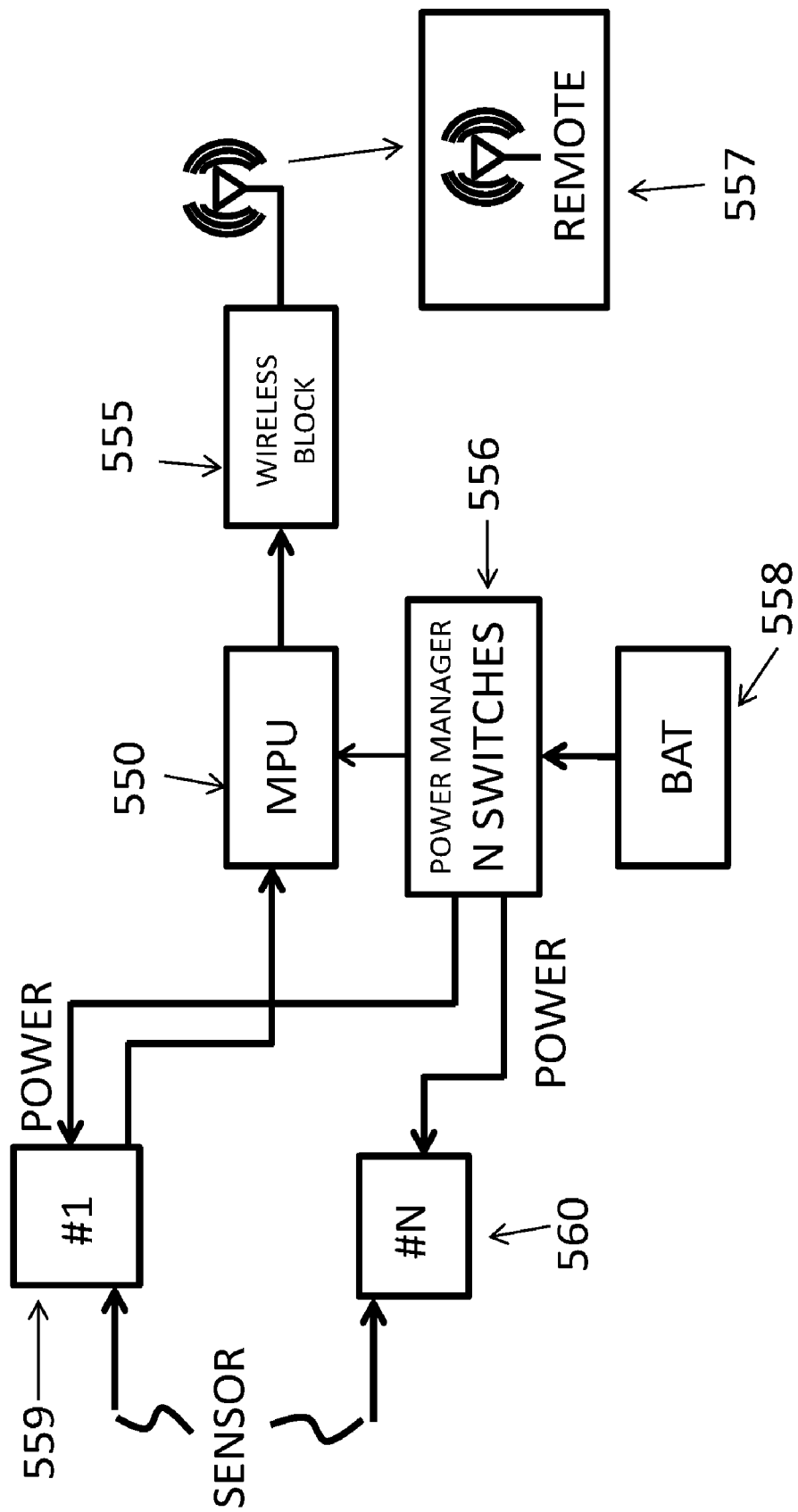
FIG. 14 illustrates an energy conserving scheme by a remote power control.

FIG. 14 depicts an energy conserving scheme. A telemonitor can receive remote commands from interact, smart phone 557, and other remote devices. A command acts upon a controller 550 to disconnect power to unused sensing channels, to be performed by a remotely programmable power distribution switch 556, which derives its power from a battery 558. This scheme also reduces wireless communications data length and reduces duty cycle as a power saying scheme for a wireless block 555.

Figure 15A:
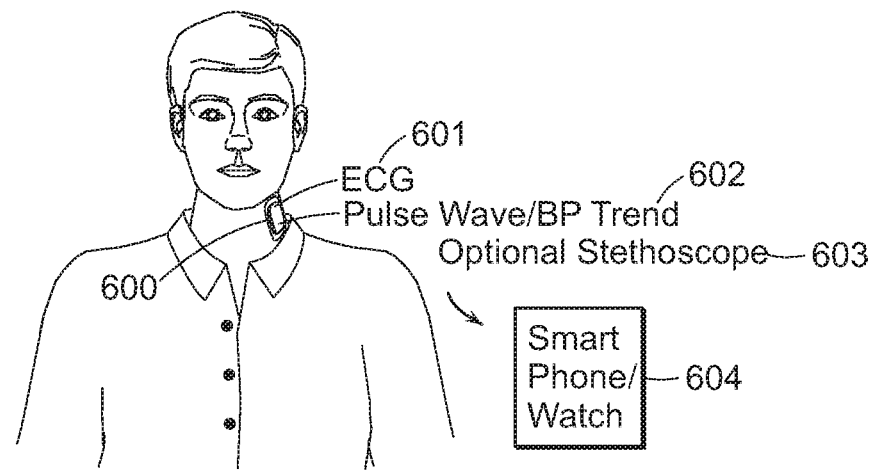
FIG. 15A and FIG. 15B depict a triage neck placement embodiment of the device with measured parameters.
Figure 15B:
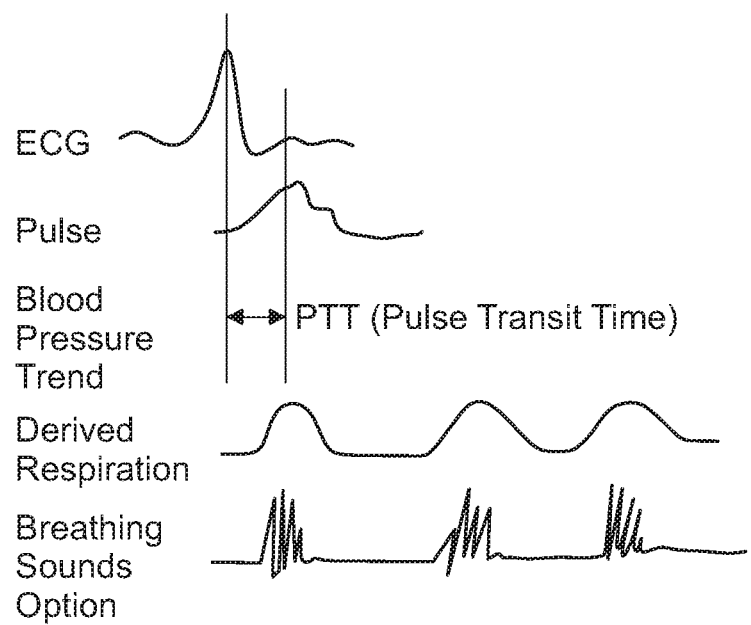

FIG. 15A depicts a triage neck placement of a telemonitor device 600. In some embodiments, the telemonitor can be a disposable triage device configured for mass-catastrophe monitoring of victims. As demonstrated in FIG. 15B, the device picks up an ECG 601 and a pulse 602, and relays the ECG 601 and the pulse 602 to a wireless gateway/alarm 604. The device can accept a stethoscope channel to enhance reliability by monitoring respiration sounds. A respiration signal is filtered from the pulse 602, as the piezo sensor produces a composite pulse/respiration waveforms. For critical triage decisions, signal redundancy is typically very useful.

Figure 16:
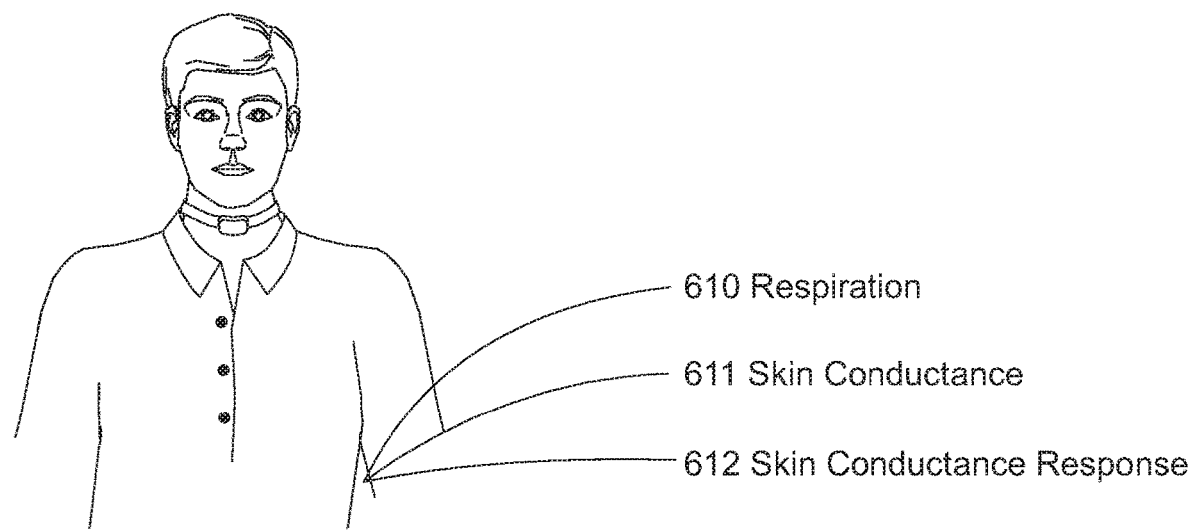
FIG. 16 depicts an embodiment of a covert stress management function of a monitor.

FIG. 16 depicts one embodiment of a covert stress management. Skin conductance 611, a skin conductance response 612 (see also FIG. 8) and a respiration 610 are monitored by a device which is out of view. A Smartphone acts as a feedback (biofeedback) trainer.

Figure 17:
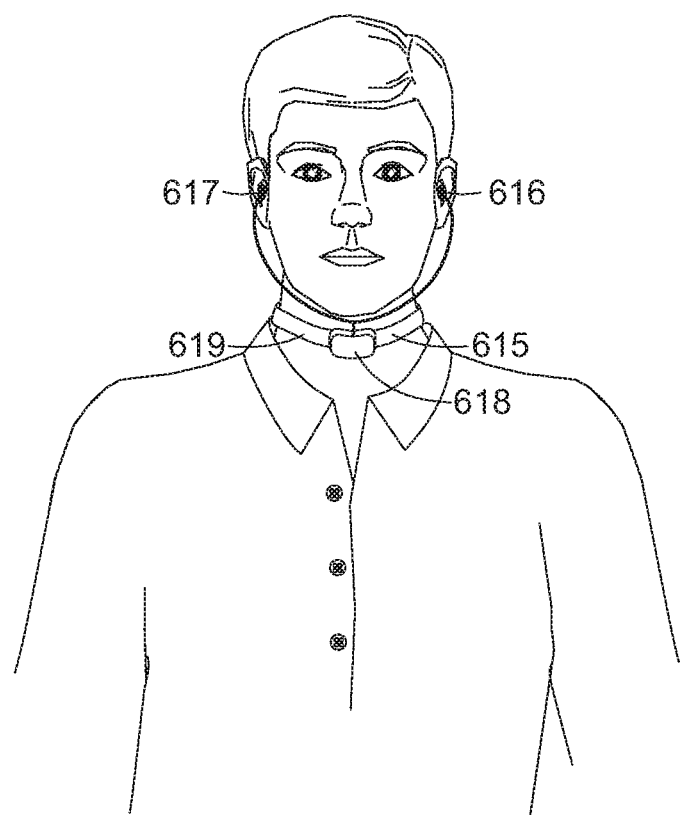
FIG. 17 depicts an embodiment of an add-on hearing aid function.

FIG. 17 depicts an embodiment of the device 615 with an add-on hearing aid function. While commercially available hearing aids are expensive, the additional needed circuitry is inexpensive. Moreover, the hearing aid's equalizer filters can be remotely programmed to compensate for the subjects' individualized hearing loss. The device 615 hangs as pendant 619 using a microphone 618 and earphones 616, 617. In some embodiments, the hearing aid function may be embedded in the device as an additional feature. In some embodiments, the device is configured to reduce feedback, particularly when earphones 616, 617 are covering a hearing aid.

Figure 18:
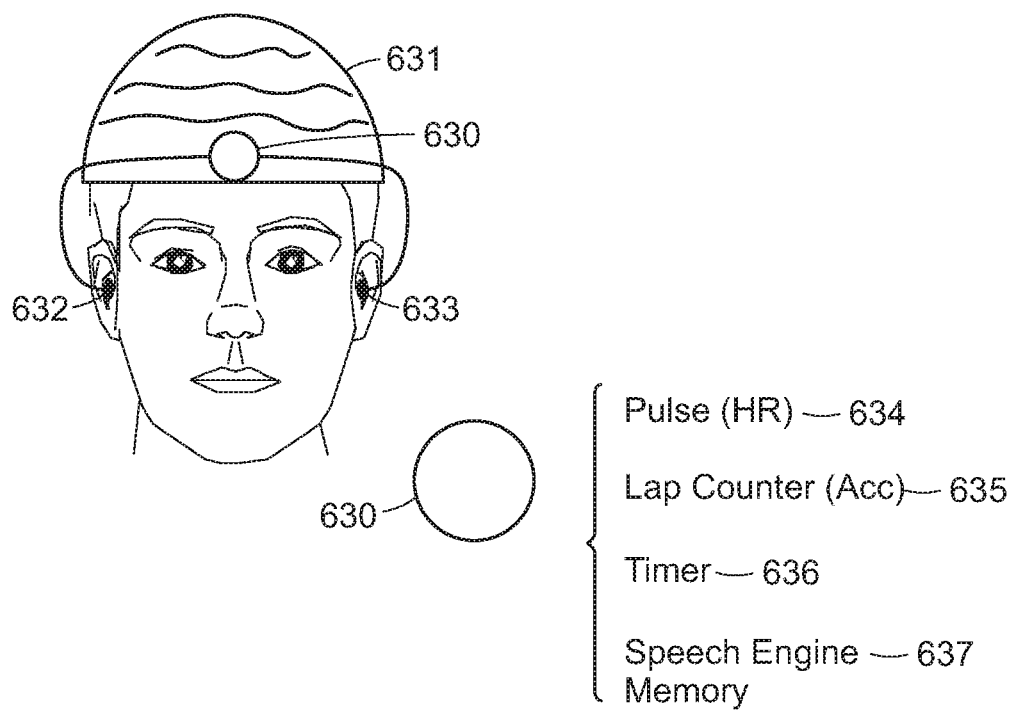
FIG. 18 depicts an embodiment of a swimming fitness trainer with a talking heart rate monitor.

FIG. 18 depicts a swimming fitness trainer 630. The swimming fitness trainer 630 comprises a talking heart rate monitor with speech engine and memory 637, a pool lap counter-timer 636, and an algorithm for measuring calories burnt and exercise scoring. The trainer 630 can fit on a forehead band or under a swim cap 631. The trainer 630 activates earphones 632, 633 (one or both). The trainer 630 monitors heart rate 634 via the monitor's isolated piezoelectric pulse wave sensor, whose capacitance exceeds 100 nanofarads, as in other implementations.

Figure 19:
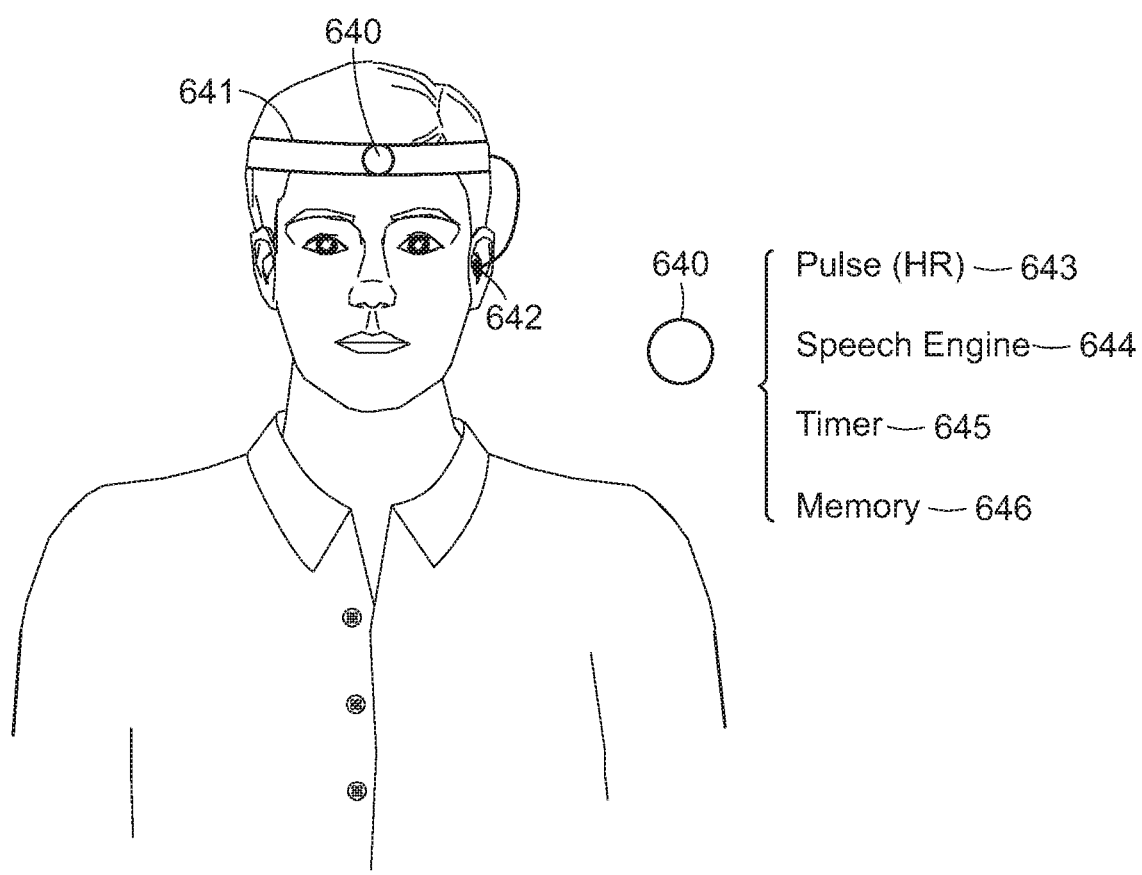
FIG. 19 depicts an embodiment of the talking fitness trainer for use on a treadmill or while walking.

FIG. 19 depicts a talking fitness trainer 640 on a forehead band 641 for use on a treadmill or while walking. The trainer 640 employs a pulse sensor throughout its application, it fits in the forehead band with no direct contact with skin, and the trainer's 641 output of speech messages are via an earpiece (or headphones) 642. The trainer forms an alternative to an ECG device that can be placed in a bra or exercise shirt and function similarly.

Figure 20:
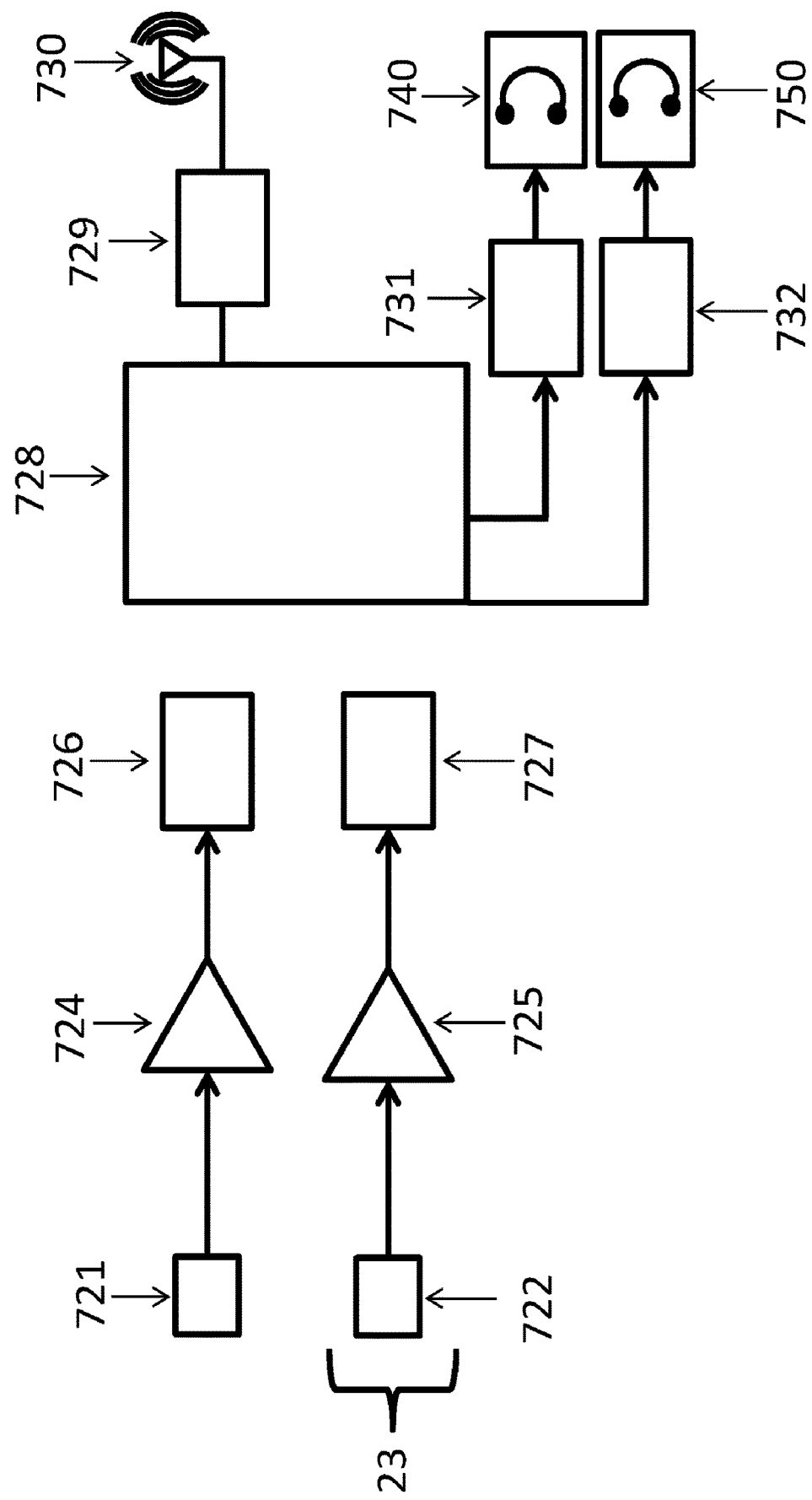
FIG. 20 illustrates an embodiment of a method for combining a stethoscope and a hearing aid in a monitor.

FIG. 20 depicts a combined stethoscope 721 and a hearing aid 722 under a single monitoring 728 control. The stethoscope comprises a membrane 723, a microphone 722, a preamp 725 and a convertor 727. The stethoscope's output amplifier 731 drives a phone 740 or is transmitted to a Smartphone or other remote device. The hearing aid comprises a microphone 721, a preamp 724 and a convertor 726. An output amplifier 732 drives phone(s) 750 or is transmitted to Smartphone or other remote device.

Figure 21:
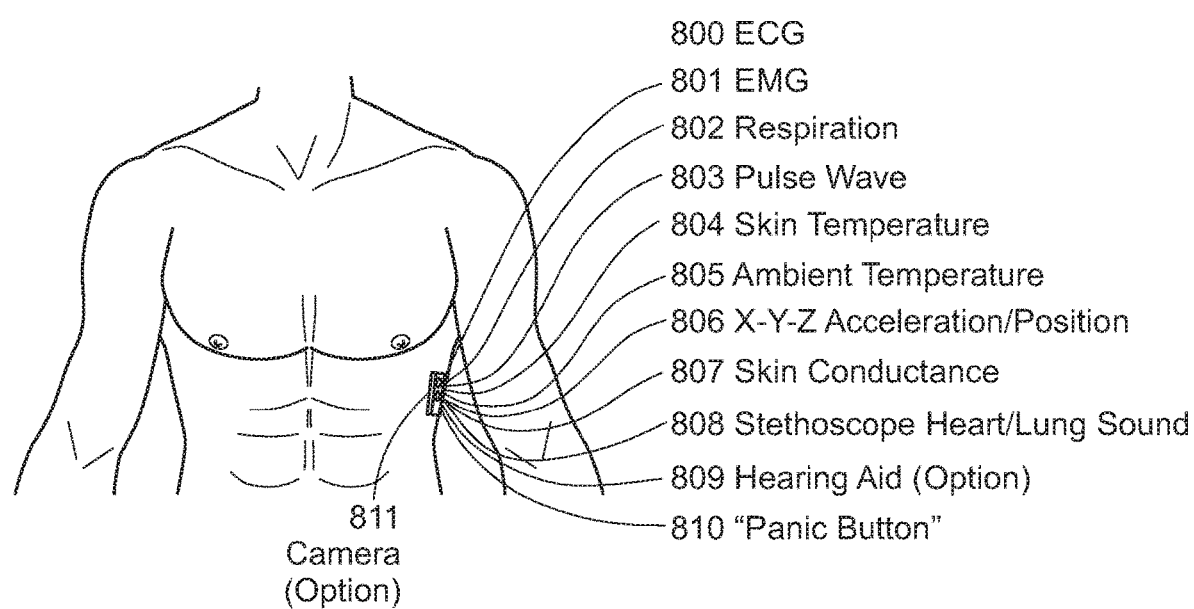
FIG. 21 depicts an embodiment of a single site multi-sensor (with $O_2$ sensor not shown)

FIG. 21 depicts an example summary of the single site multi-sensors in an embodiment of a single printed circuit board area similar to that of a credit card. The SOM monitor packs on both side a broad array of sensors, front-end analog amplifiers/filters, data conversion and digital signal processing, battery management and wireless connectivity. Not shown but described elsewhere are micro SD memory and SPO2 function. The SOM packs one or more of the following parameters: ECG (800); EMG (801); Respiration (802); Pulse wave (803); Skin temperature (804); Ambient temperature (805); XYZ acceleration/body position (806); Skin conductance (807); Heart/lung sounds stethoscope (808); Remotely programmable hearing aid (809); "Panic button" (810), physical or tap-sensitive sensors already included (e.g., piezoelectric pulse/respiration sensor), and a skin vibrator (not shown).

Figure 22:
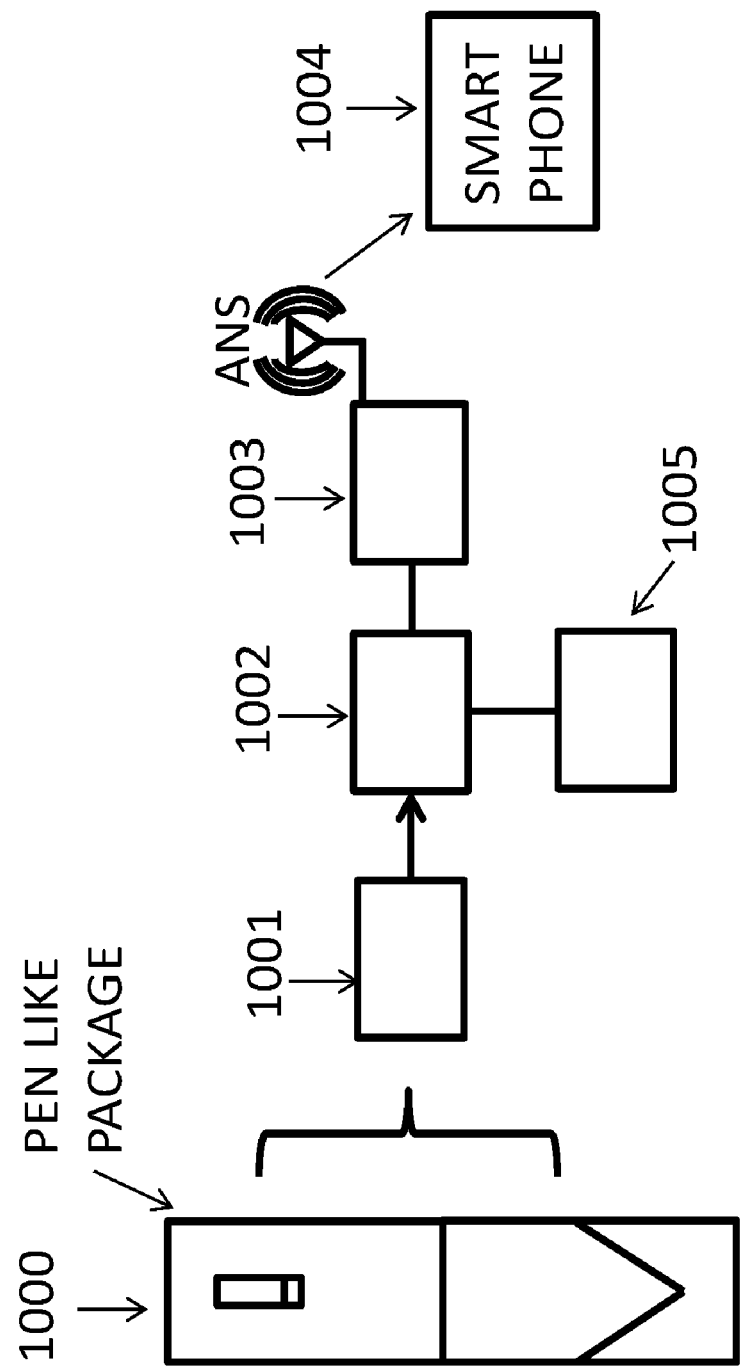
FIG. 22 depicts an embodiment of a posture/slouch feedback trainer, including man-down detection and fall prediction.

FIG. 22 depicts a posture slouch feedback trainer 1000 including man-down and fall predictor. A posture is monitored by acceleration sensors 1001 embedded in a pen-like package 1000 and signal-conditioned by 1002. A skin vibrator 1005 enables a silent, covert feedback when a slouching angle is reached. A wireless means 1003, e.g., Bluetooth, communicates any relevant data to an external means, including a smart phone or a smart watch 1004. In some embodiments there is a method for extracting body slouches and sway parameters from a three-axis acceleration sensor.

In some embodiments, the device 1002, or a minimum configuration device with only a triaxial acceleration sensor, can serve as a remote man-down alert via the Smartphone, a smart watch, or other wireless devices. The posture trainer 1002 can also be employed as a predictor of fall propensity, by using Lissajous pattern (see FIG. 26) analysis of body sway when standing. For fall prediction, the X-Y axis are of primary importance, while the Z direction is a parameter of actual fall-in-progress. A daily test is implemented in which a subject stands and sways in a natural posture. A technology of measuring body sway in a daily living environment for elderly people can be used as part of a balance, stability and fall risk assessment tool. The X-Y vectors of the triaxial acceleration sensor are first amplified for high sensitivity, better than 0.1 G full scale. The data is then analyzed as a pattern recognition of possible deterioration trends vs. a baseline. The data analyzed is primarily made of the line length of the Lissajous pattern of the X-Y components.

Figure 26:
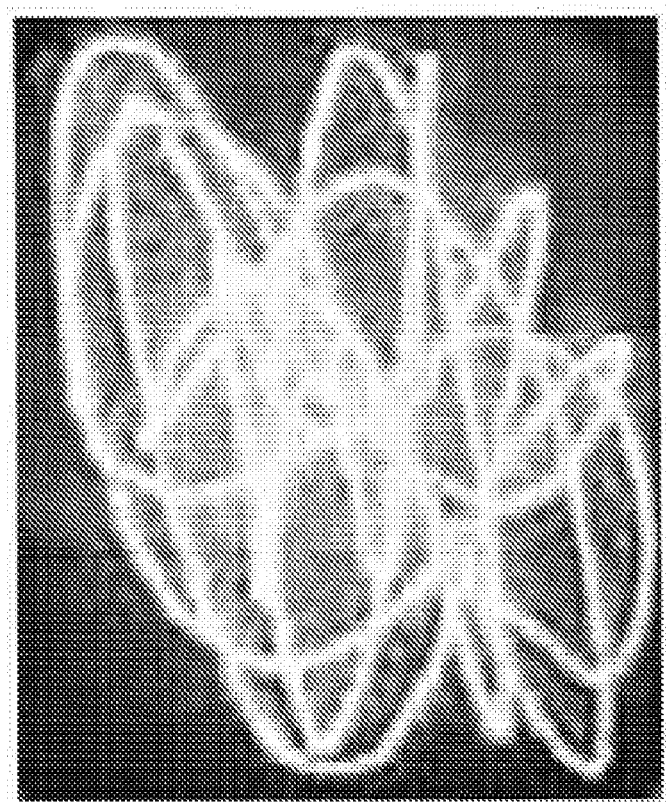
FIG. 26 depicts X-Y body sway pattern for fall prediction analysis.

The illustrated pattern of FIG. 26 is a typical Lissajous pattern of body sway while standing. In some embodiments, the device 1002 further comprises an algorithm based on line length comparison in a given time period (e.g., 60 seconds) of each test data vs. baseline. As the subject's balance deteriorates, the line length divided by the baseline line length will increase. Such a gradual increase of the ratio above 1 will signify that the subject should seek a professional checkup.

Figure 23:
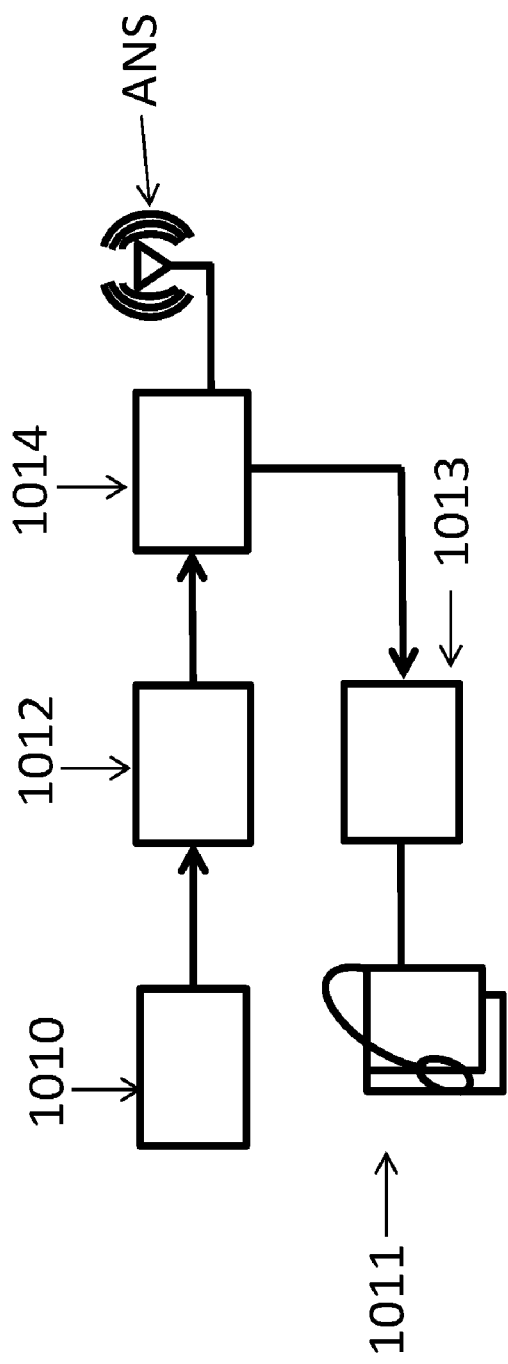
FIG. 23 depicts an embodiment of a distress-activated microphone channel.

FIG. 23 depicts a device with a use of a hearing aid microphone or an independent microphone 1010 as a distress-activated audio channel 1012. An amplifier/converter module 1012 feeds a controller 1014 with an embedded wireless means, as well as a vibrator driver 1013 and vibrator 1011. Upon diagnosing a potential life threatening event or a fall, the device opens up the audio channel so that a remotely located family member or a service provider can obtain real-time physiological data as well as hear a subject talking, yelling, groaning, etc. The subject can override this function following sensation of vibrotactile activation by pressing an override button or tapping a code on the unit (e.g., 3 taps).

Figure 24:
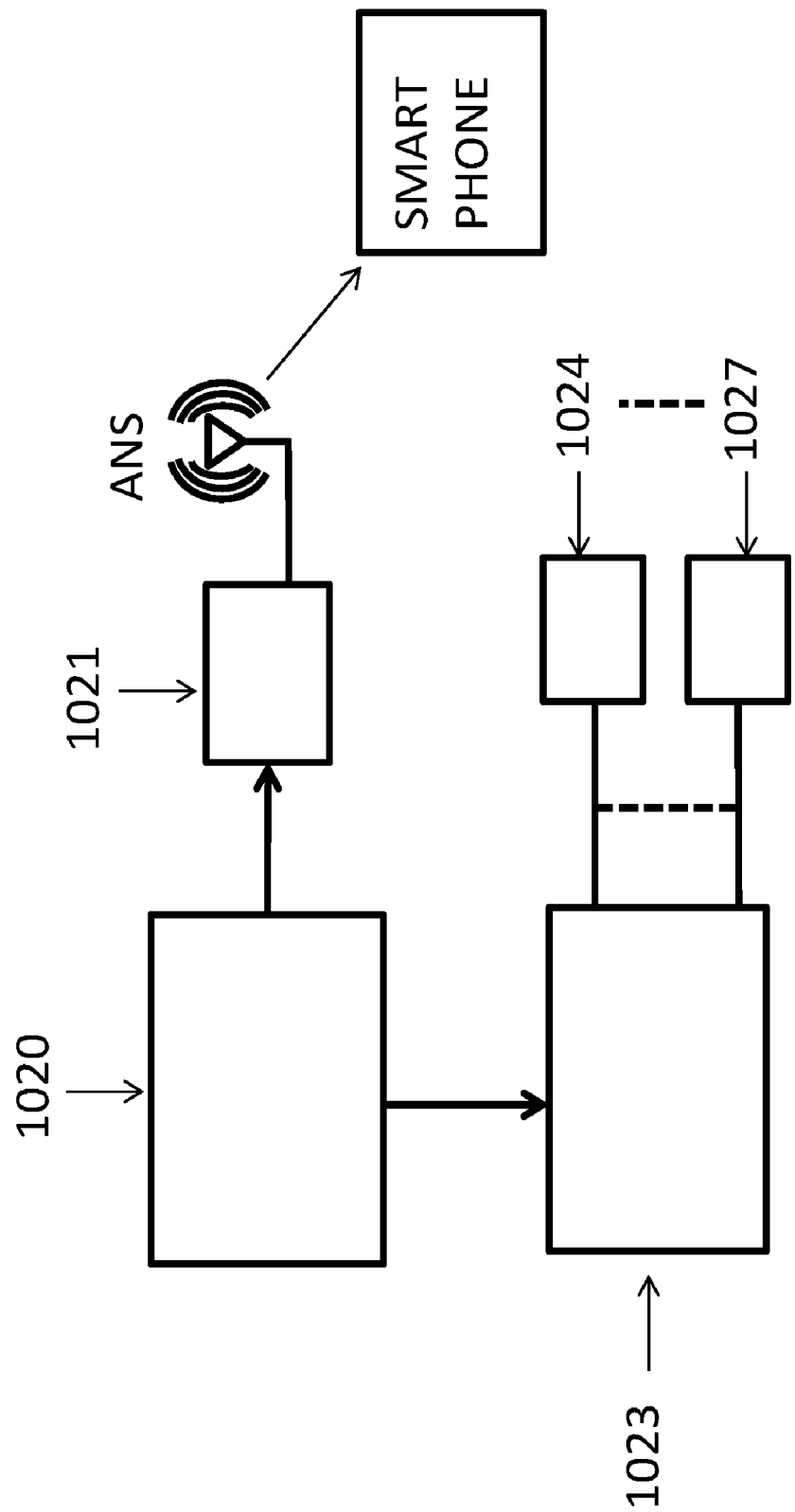
FIG. 24 depicts an embodiment of a nerve stimulator addition to a monitor that is programmable by a Smartphone or a smart watch.

FIG. 24 depicts an embodiment of the device with a nerve stimulator addition where a monitor 1021 is remotely programmable by a Smartphone, smart watch, etc. 1022. FIG. 24 also depicts an embodiment of the device further comprising a TENS unit. Further disclosed is a remotely programmable pulsed electric current generator 1023 to stimulate nerves via single channel electrodes 1024, 1025 (single channel) or with two channel electrodes 1026, 1027 for therapeutic purposes (general muscle pain, sports injuries, etc.). The TENS covers a broad range of transcutaneously applied currents in the form of pulses for nerve excitation. The TENS unit connects to the skin using two or more electrodes. The entire programming of the intensity, pulse frequency and shape, as well as treatment time, is all remotely programmable via the interact or locally via Smartphone, smart watch or tablet. In some embodiments, the device further comprises an EMG monitor enabled to track treatment progress towards relaxing a spastic or a painful muscle.

Figure 25B:
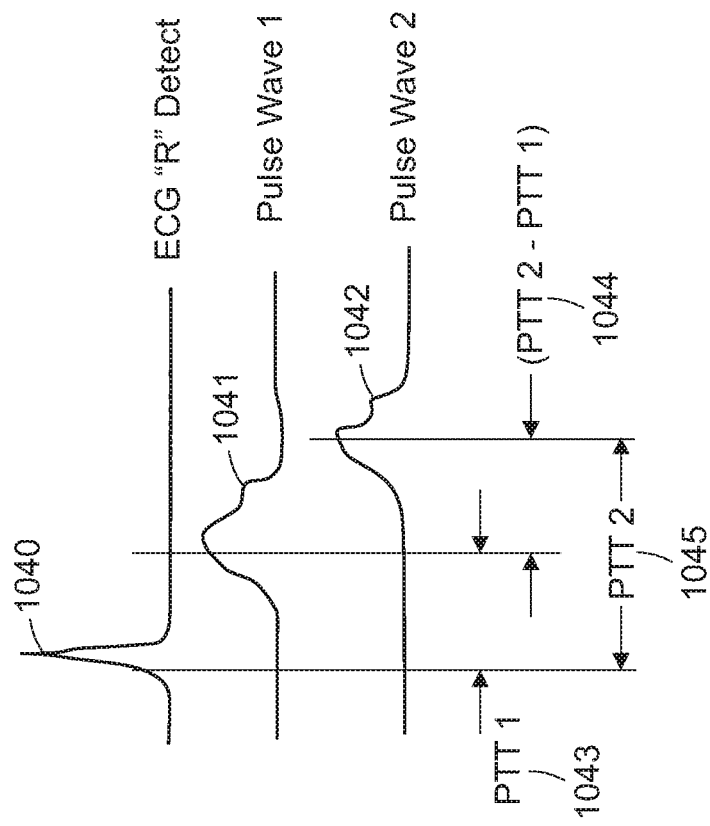
FIG. 25A and FIG. 25B depicts an embodiment of a circulatory monitoring scheme that uses two pulse sensors and ECG.
Figure 25A:
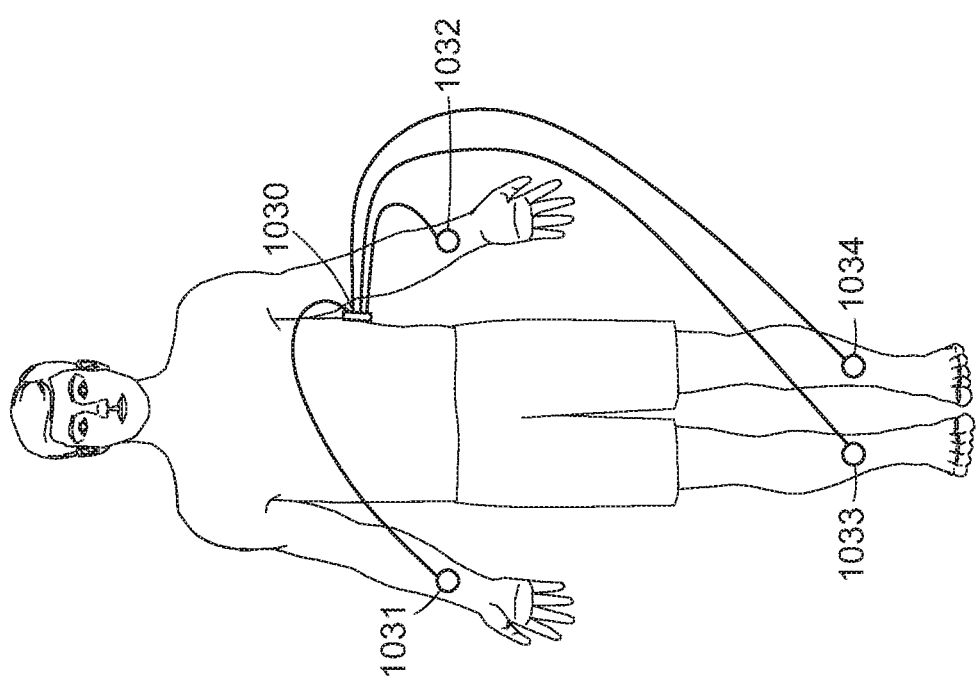

FIG. 25A and FIG. 25B depict an embodiment of a circulatory monitoring using dual pulse wave sensors. A main monitor comprises the ECG 1030 and its R wave detector 1040, and the monitor establishes a reference against two simultaneous pulse wave sensors 1031/1032 and/or 1033/1034, and is plugged in periodically to provide remote follow-up of circulatory problems. Particularly, as seen in FIG. 25B, it is the difference 1044 between the transit time of the PPT1 outputs 1043 and PTT2 1045 that raise a possible serious problem. The outputs are PTT's 1043, 1045 with respect to ECG R wave 1040 monitored on the torso 1030. Another signal 1044 is the pulse transit time PTT 2-PTT 1. The differential deltas have a diagnostic value in detecting circulatory problems. For example, blood pressure in one arm different in the other arm indicating a possible blockage of the brachial artery. The clinical significance is that small differences in blood pressure readings between a right and a left arm (10-15 mm) are normal. Large differences above 15 mm suggest the presence of an artery-clogging plaque in a vessel that supplies blood to the arm with higher blood pressure. Such plaque is a signal of peripheral artery disease (cholesterol-clogged arteries anywhere in the body other than the heart). When peripheral artery disease is present, there's a good likelihood that arteries in the heart and brain are also clogged, raising the danger of having a heart attack or stroke. Most cardiologists routinely measure blood pressure in both arms as part of an initial evaluation, while most primary care doctors do not. The device introduces a method to track a difference in limb blood pressure to provide additional remotely-taken information about a cardiovascular risk prediction. Finally, a delta in PTT can be taken not only from arm-to-arm or leg-to-leg, but also arm to leg of same or diagonal sides. As long as a personal baseline is established when the true blood pressure is taken, the trends are important as predictors of possible medical event—and enabling early remedial action.

FIG. 26 depicts a body sway as registered by x-y acceleration sensor (Lissajous pattern). The patient state is taken by monitoring against baseline in a standing position for same time period (e.g., 30 or 60 seconds) resulting in a simulated line. An algorithm measuring the line length enables detection of progressive postural instability as an increasing line length with respect to baseline.

Figure 26A:
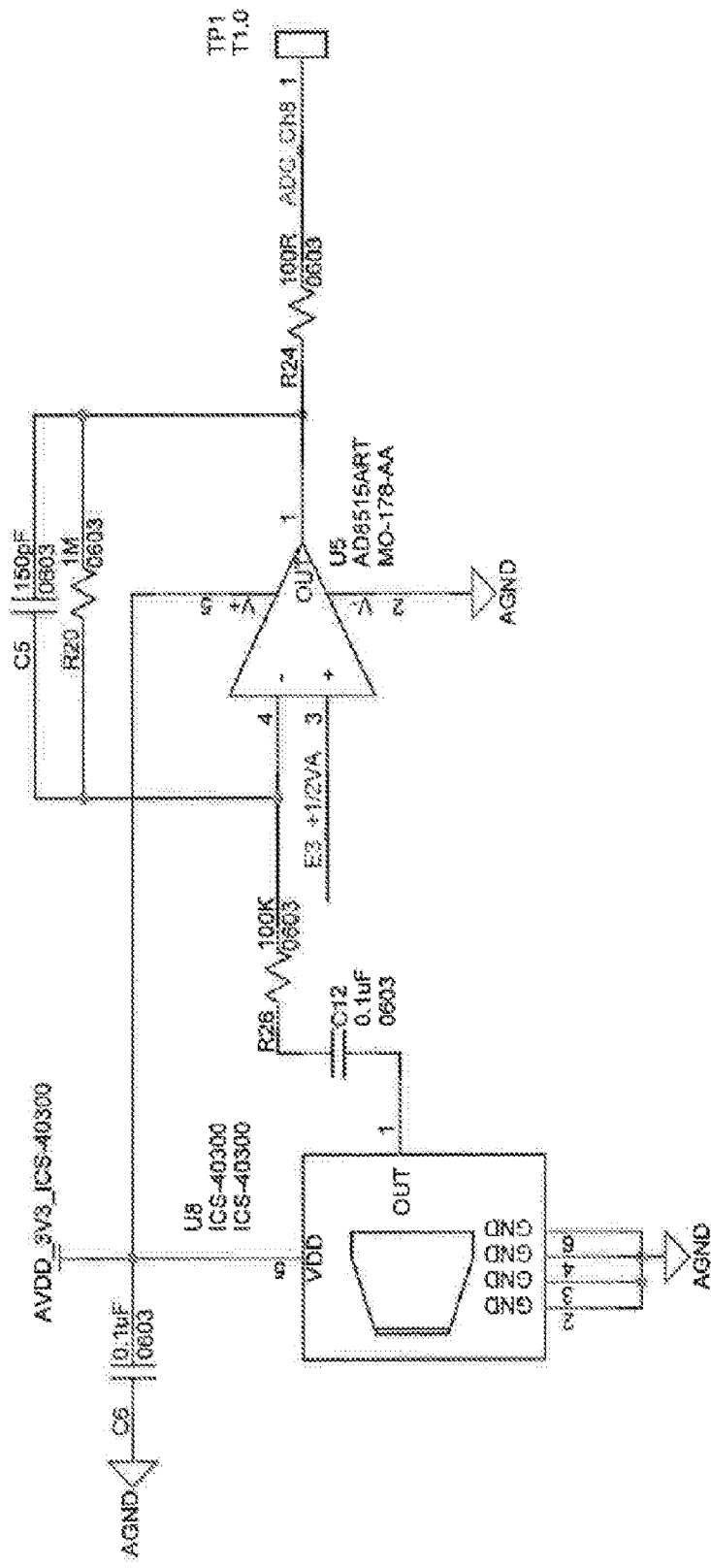
FIG. 26A depicts an embodiment of a MEMS microphone and amplifier serving as electronic stethoscope.

FIG. 26A depicts a MEMS microphone+amplifier, creating an electronic stethoscope by incorporation a diaphragm in front of the microphone.

Figure 27:
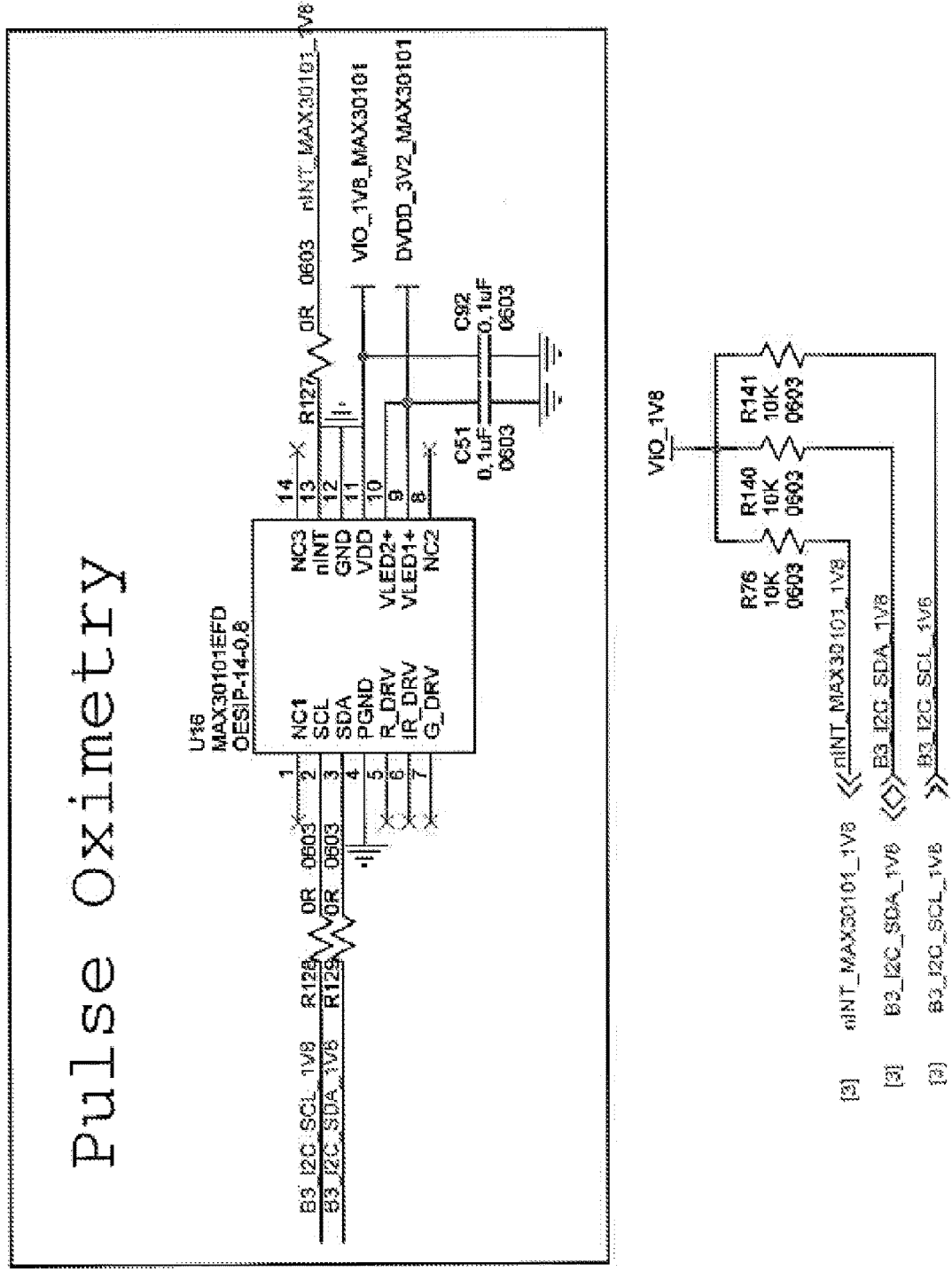
FIG. 27 illustrates an embodiment of a schematic diagram of a pulse oximeter.

FIG. 27 depicts a pulse oximeter. LEDs on the pulse oximeter are activated on demand in order to monitor oxygen saturation. The pulse wave is not used since it draws substantial current and has a piezoelectric substitute which does not draw power.

FIG. 28 is an embodiment of the device with four electrode pads, although one, two, three, four, five, six or more electrodes may be included in various embodiments.

Figure 29:
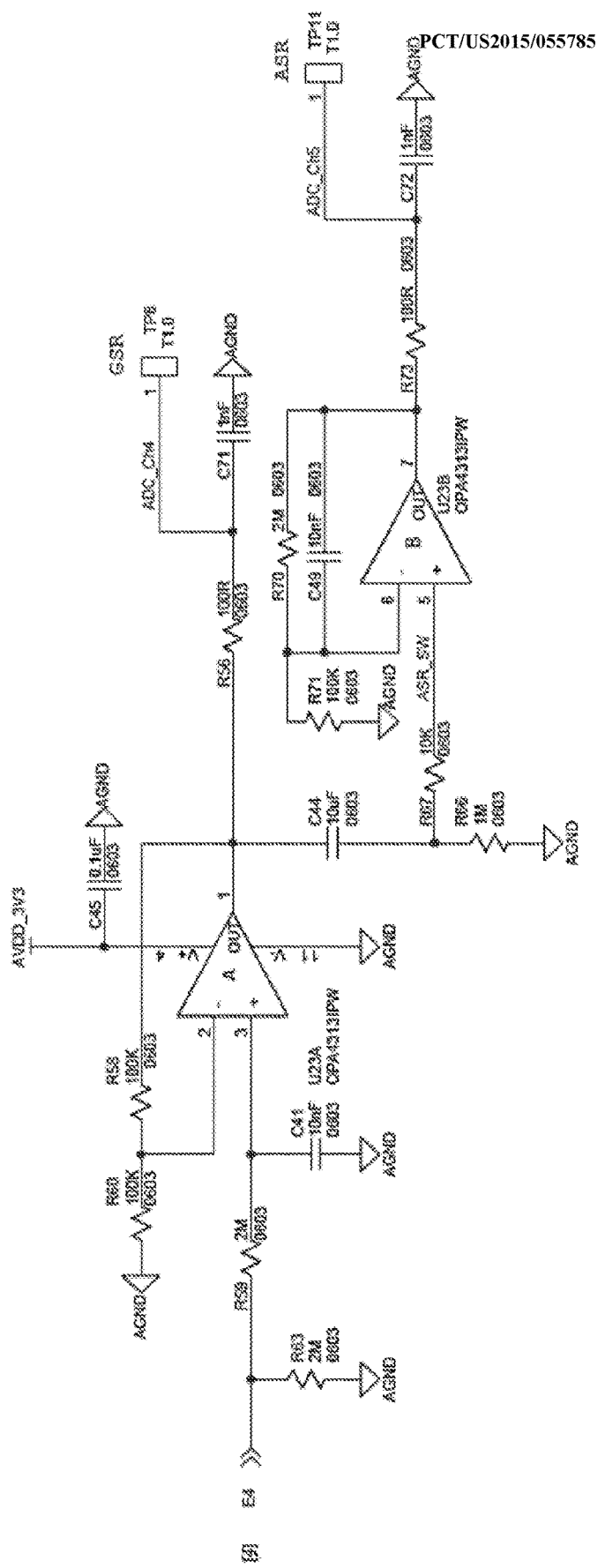
FIG. 29 depicts an embodiment of a skin resistance channel.

FIG. 29 depicts a skin conductance and a skin conductance response amplification.

Figure 30:
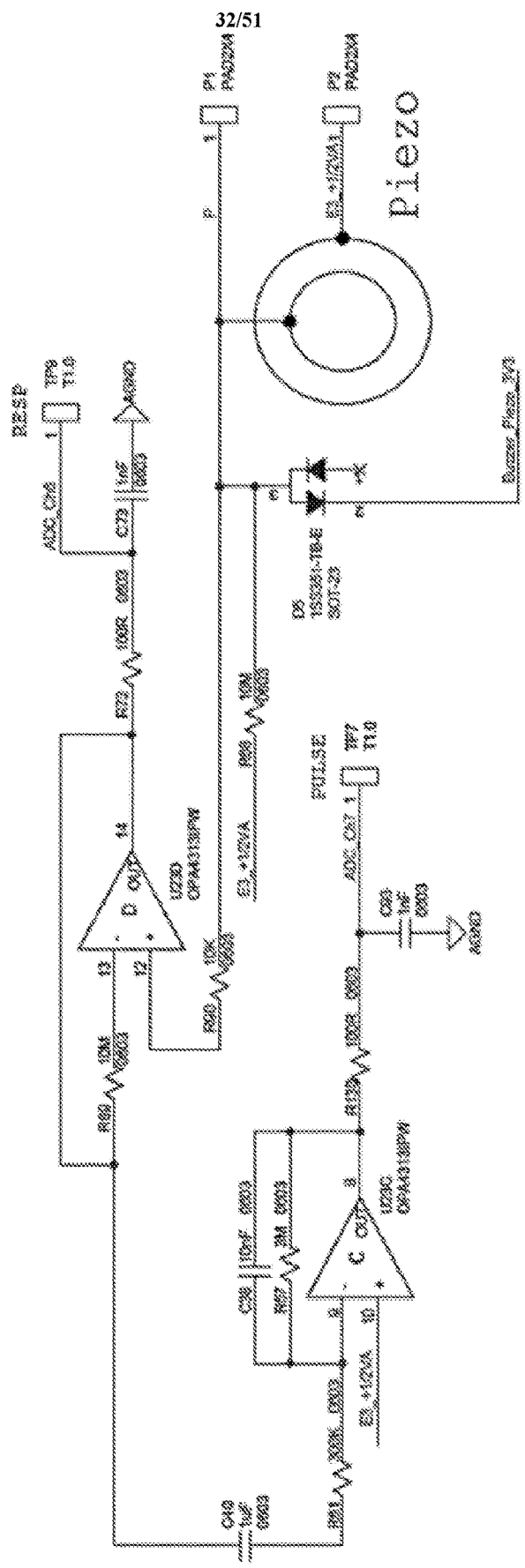
FIG. 30 illustrates an embodiment of a piezo pulse and respiration sensor with corresponding filter amplifiers, where the piezo doubles in function as an alerting buzzer or speaker.

FIG. 30 depicts a piezoelectric sensor, respiration and pulse wave amplifier filters, and a digital input from a microcontroller through a diode, enabling the piezoelectric sensor, or transducer, to function as a buzzer or a loudspeaker upon an alerting condition.

Figure 31:
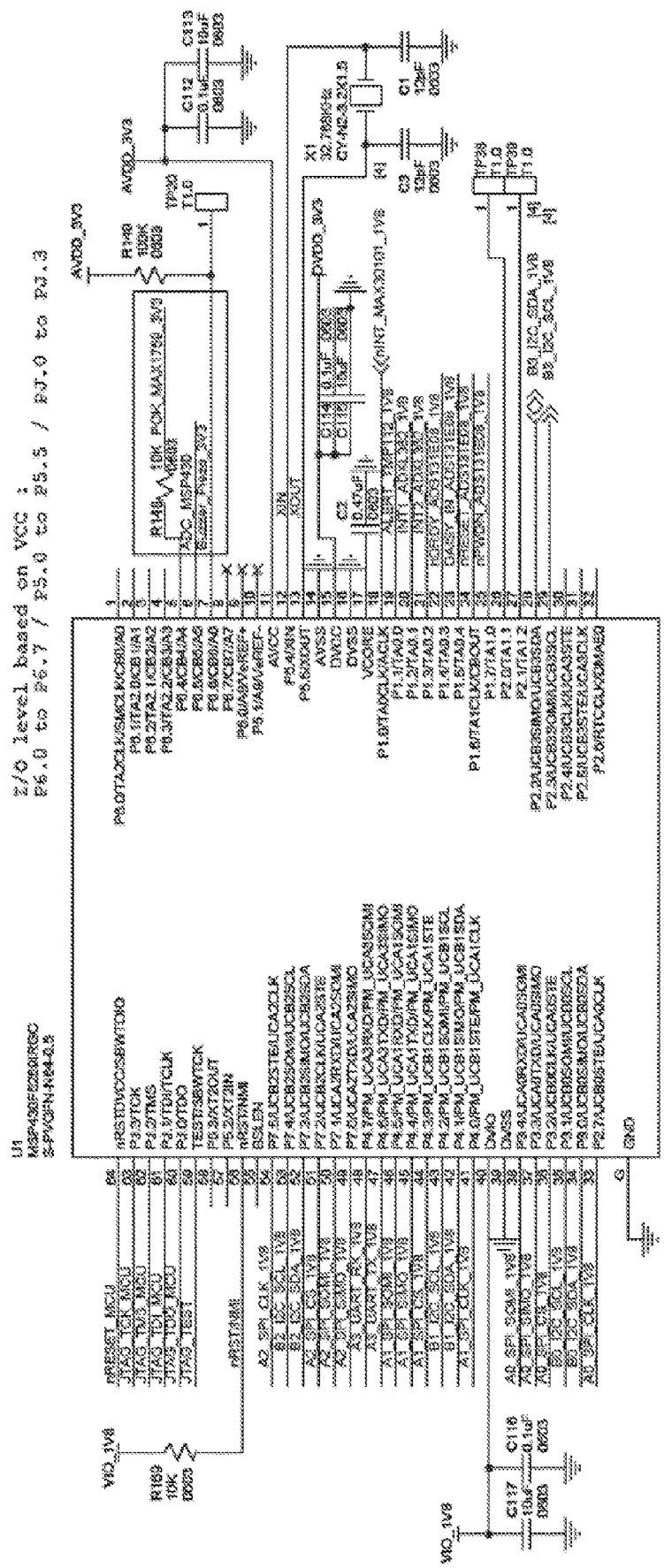
FIG. 31 illustrates an embodiment of a schematic diagram of a microcontroller (MCU)

FIG. 31 depicts an example embodiment using a microcontroller.

Figure 32A:
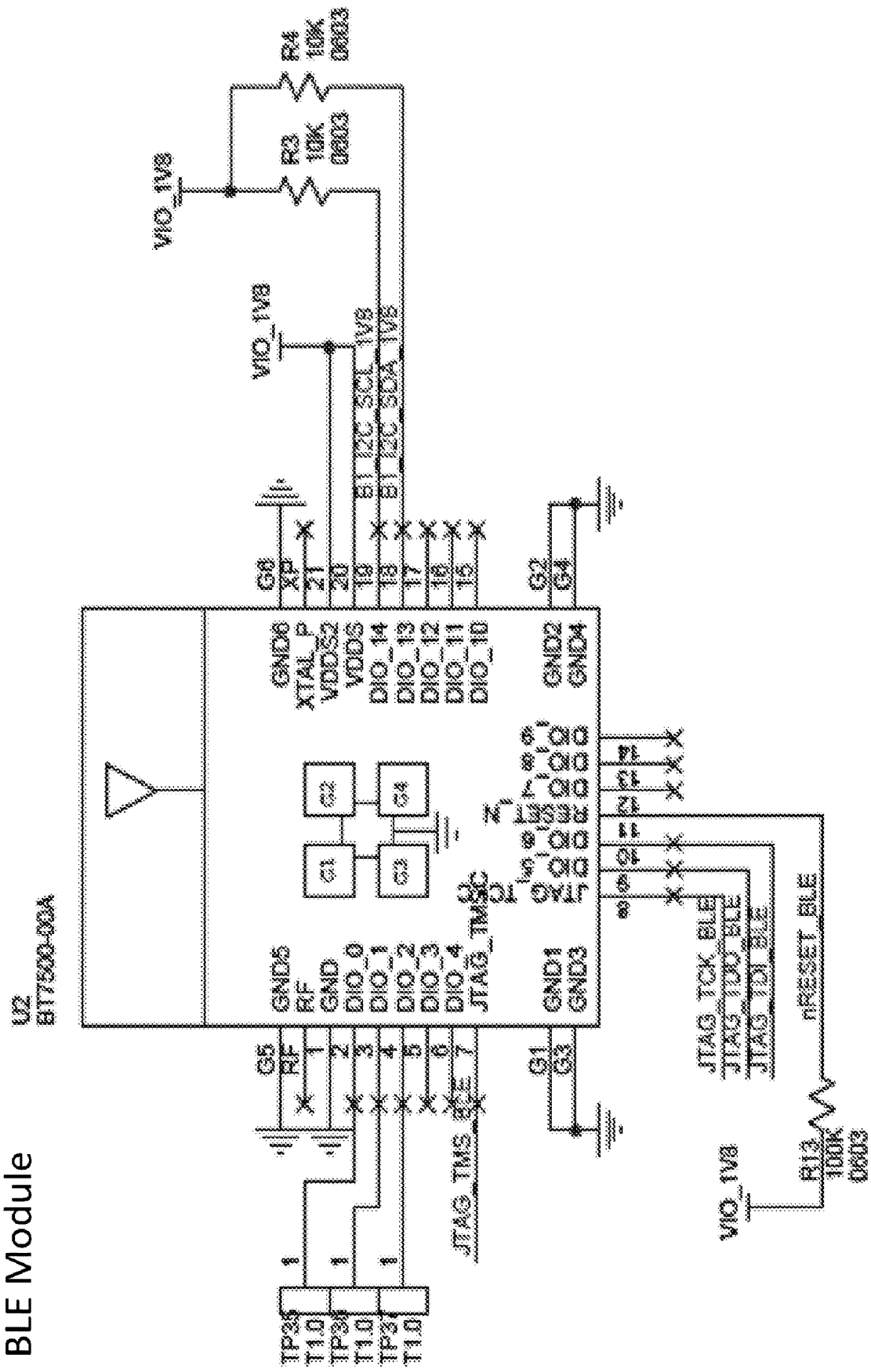
FIG. 32A illustrates an embodiment of a schematic diagram of a Bluetooth (BLE) module.

FIG. 32A depicts an example embodiment of Bluetooth low energy radio frequency module for wireless communication.

Figure 32B:
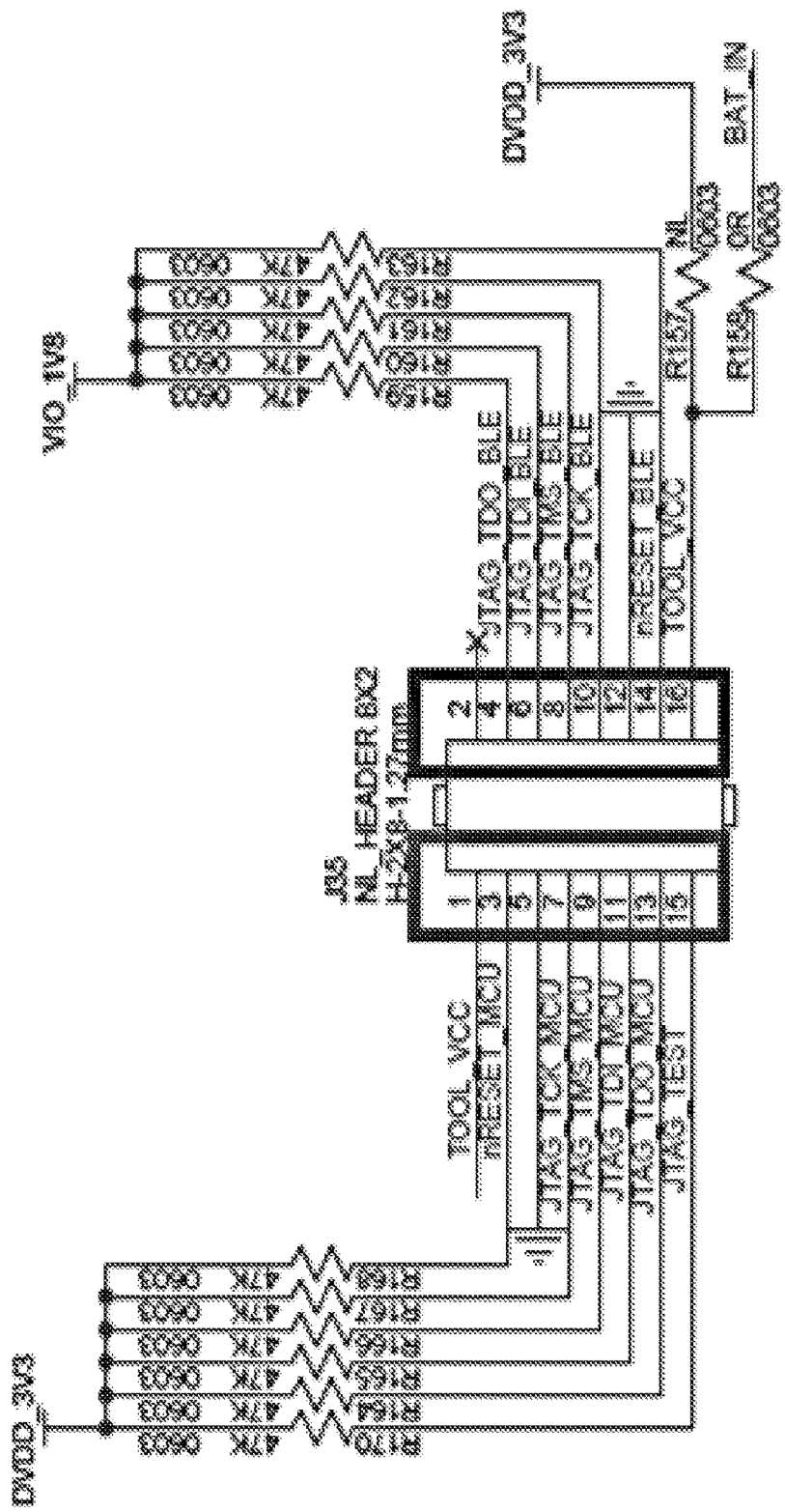
FIG. 32B illustrates an embodiment of a schematic diagram of a joint test action group (JTAG) of a MCU/BLE.

FIG. 32B depicts a test connector for programming the device.

Figure 33:
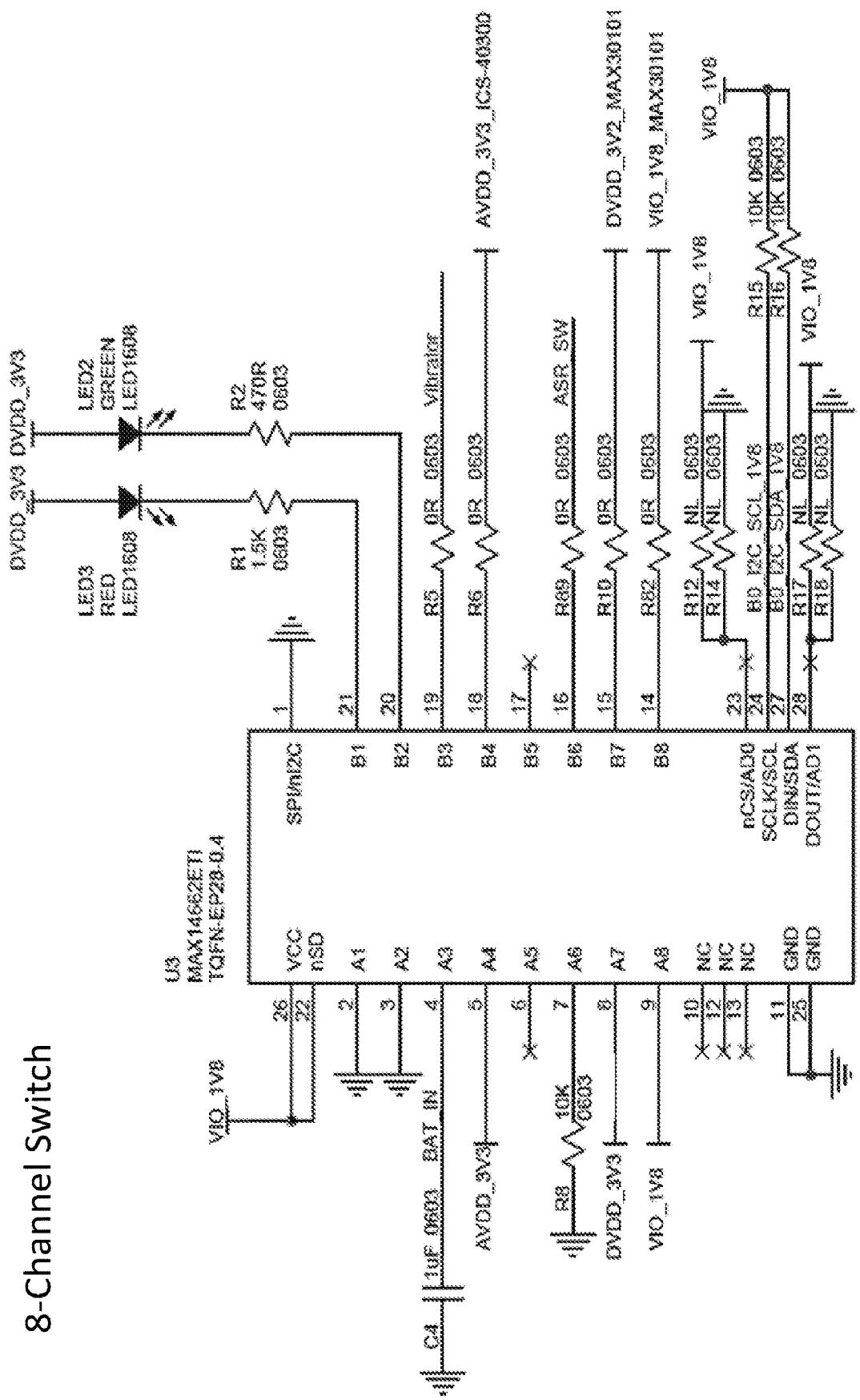
FIG. 33 is an embodiment of a schematic diagram of an 8-channel switch.

FIG. 33 depicts an 8 channel switch that, under program control, activates the LEDs, the skin vibrator and the power to the various sensing modules.

Figure 34:
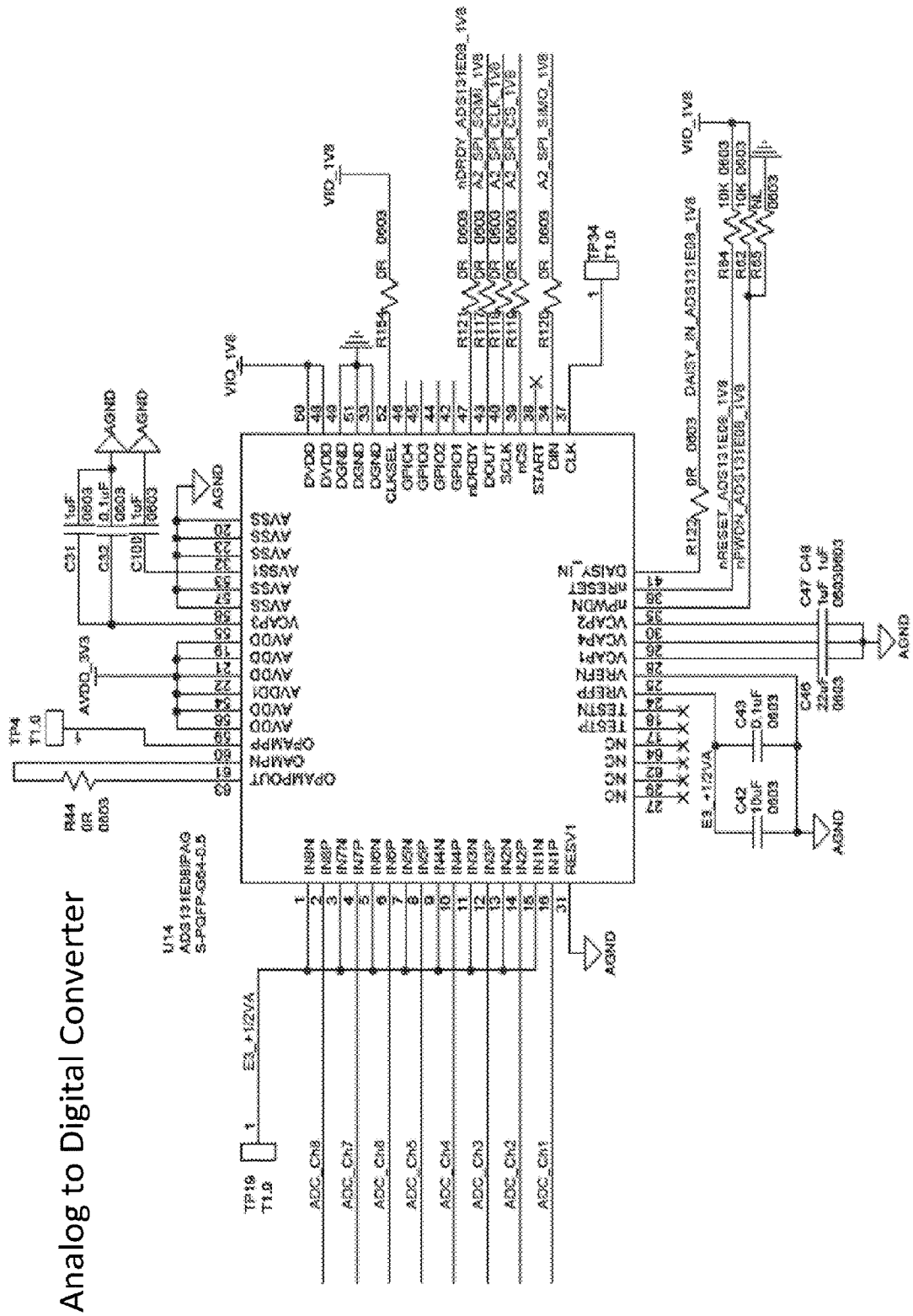
FIG. 34 is an embodiment of a schematic diagram of an analog to digital converter.

FIG. 34 depicts the analog to digital converter, 24 bits resolution in this example embodiment.

Figure 35A:
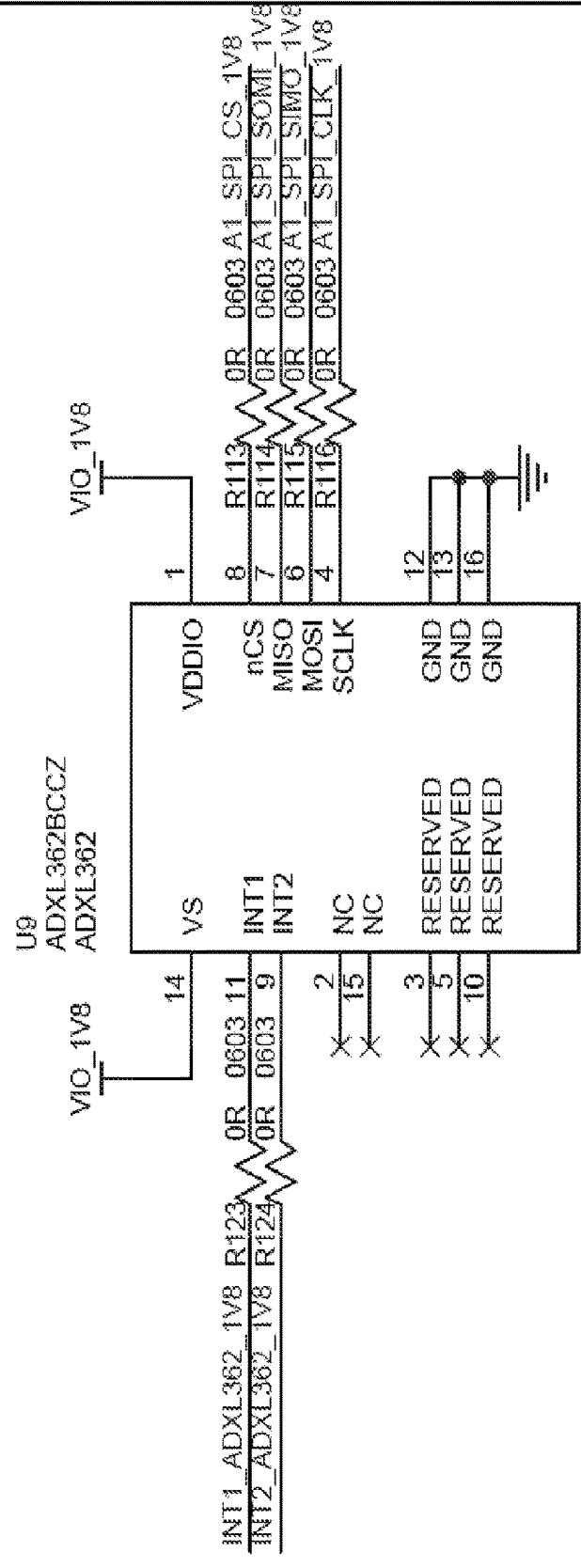
FIG. 35A is an embodiment of a schematic diagram of a MEMS accelerometer.

FIG. 35A depicts an embodiment of a MEMS accelerometer sensor.

Figure 35B:
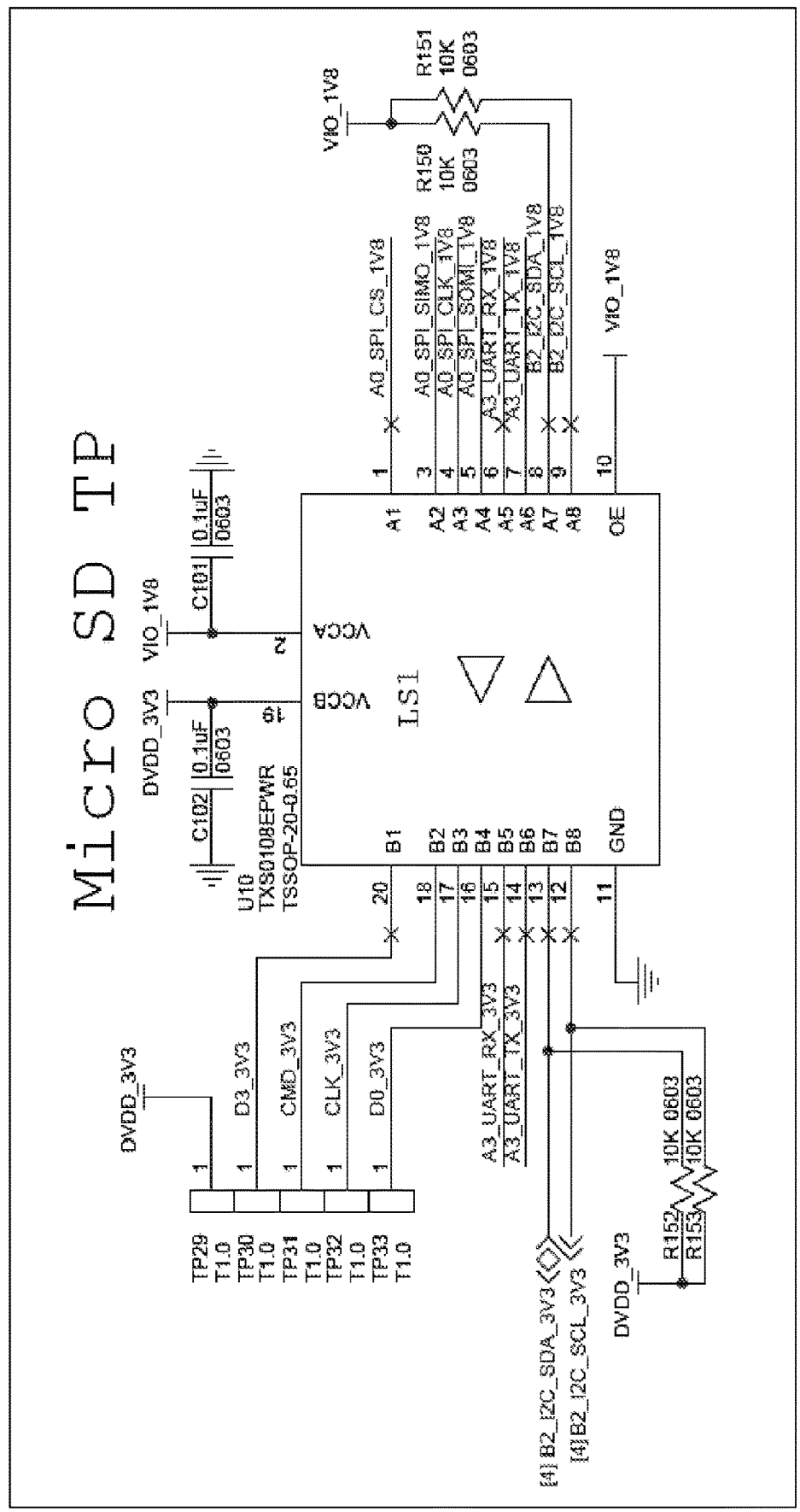
FIG. 35B is an embodiment of a schematic diagram of a micro SD memory.

FIG. 35B depicts an embodiment of a micro SD card.

Figure 35C:
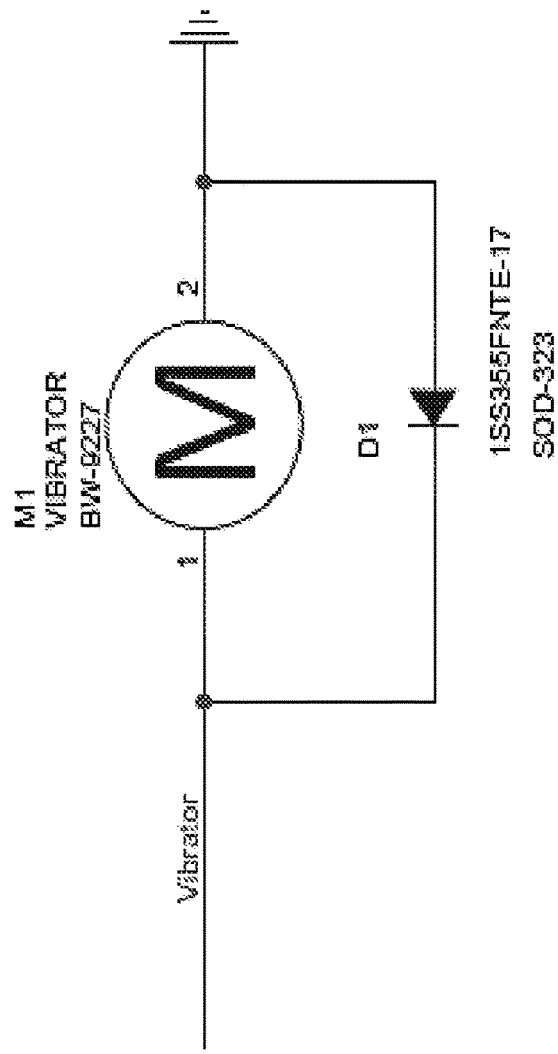
FIG. 35C is an embodiment of a schematic diagram of a feedback vibrator.

FIG. 35C depicts an embodiment of a feedback vibrator sensor.

Figure 35D:
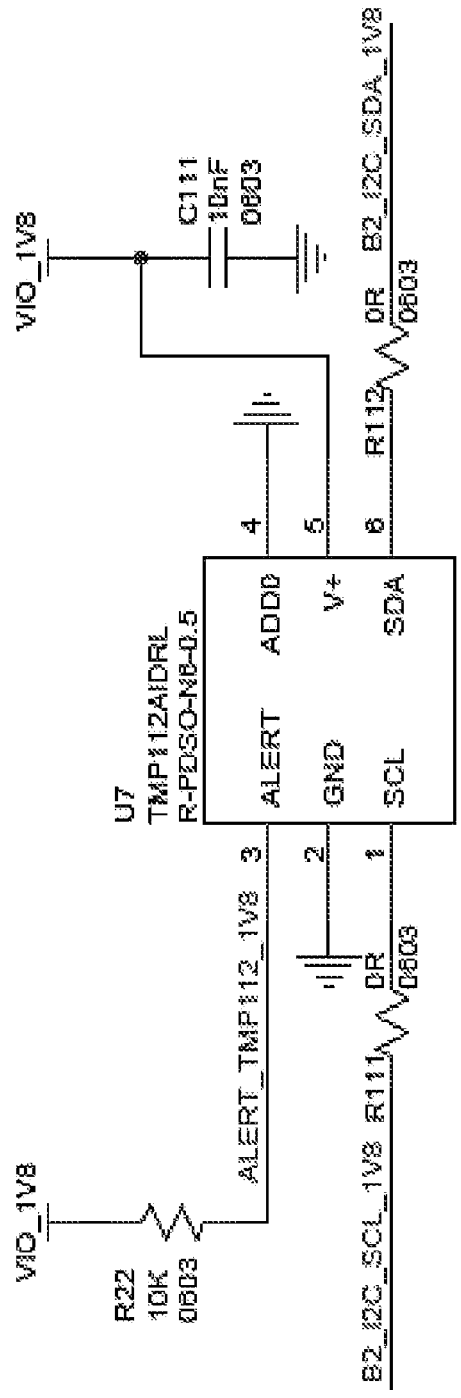
FIG. 35D is an embodiment of a schematic diagram of an ambient temperature sensor.

FIG. 35D depicts an embodiment of an ambient temperature sensor.

Figure 35E:
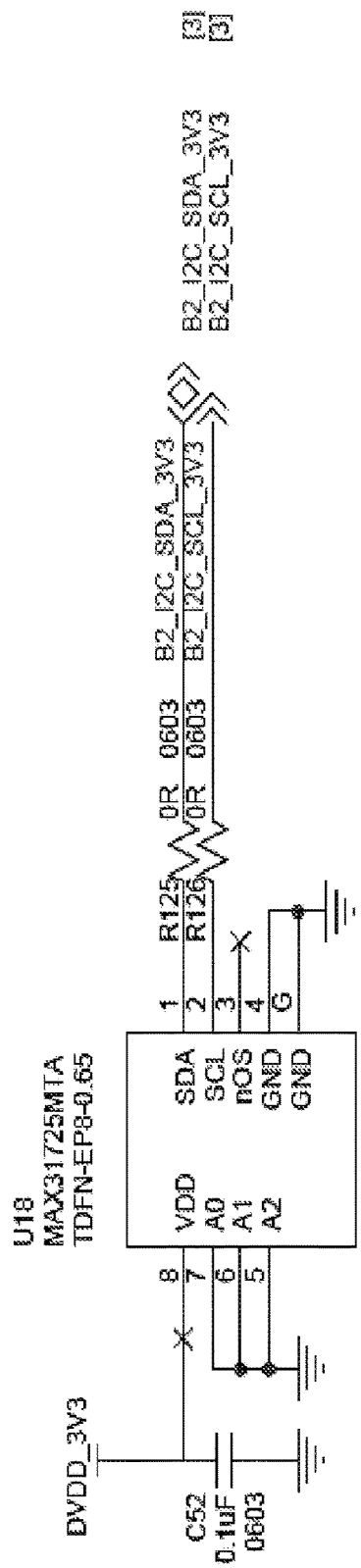
FIG. 35E is an embodiment of a schematic diagram of a skin thermometer.

FIG. 35E depicts an embodiment of a skin thermometer sensor.

Figure 36A:
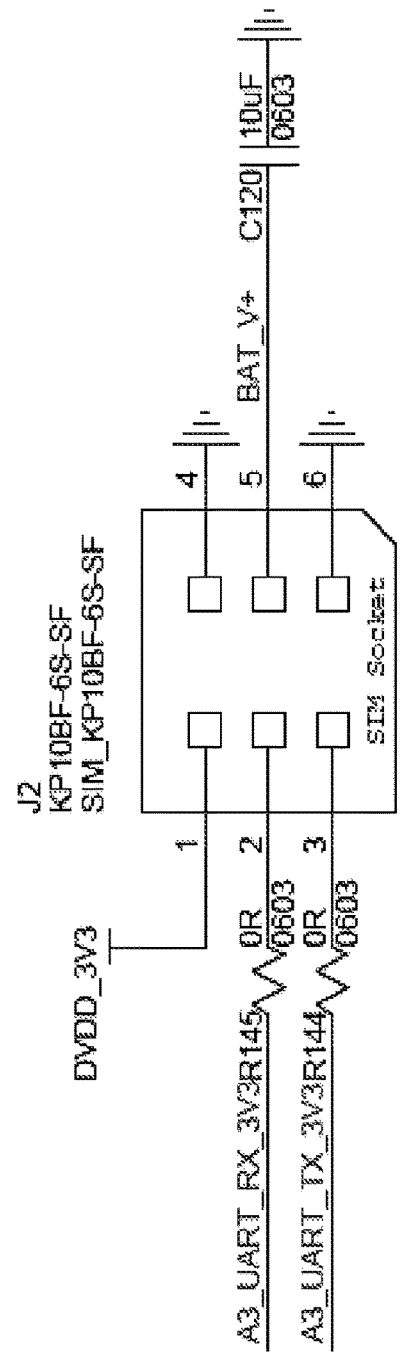
FIG. 36A is an embodiment of a schematic diagram of a SIM connector for charging and debugging.

FIG. 36A depicts the SIM connector for charging and debug.

Figure 36B:
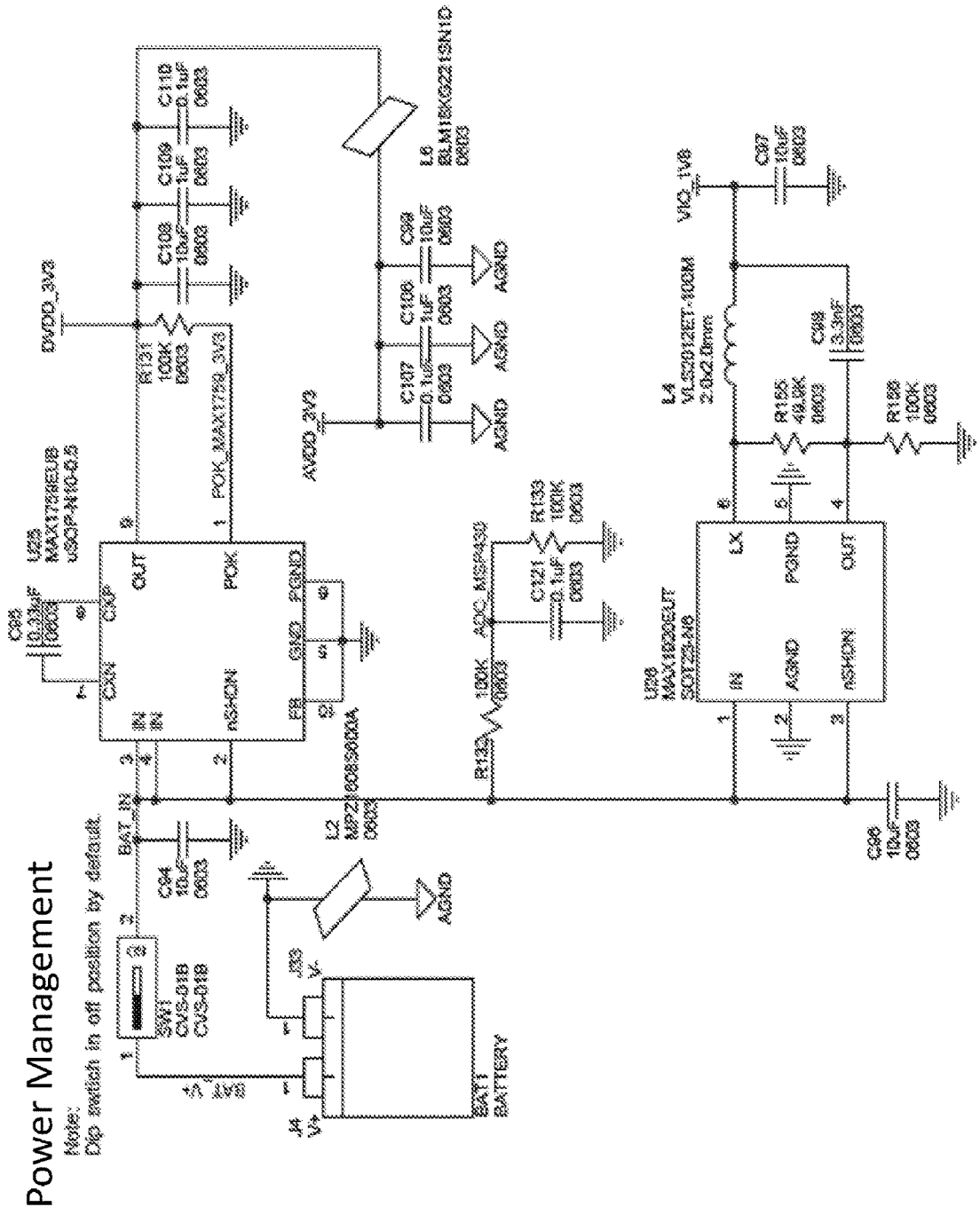
FIG. 36B is an embodiment of a schematic diagram of a power management system.

FIG. 36B depicts the battery management, converting the battery voltage into a regulated analog and digital module voltages.

Figure 37:
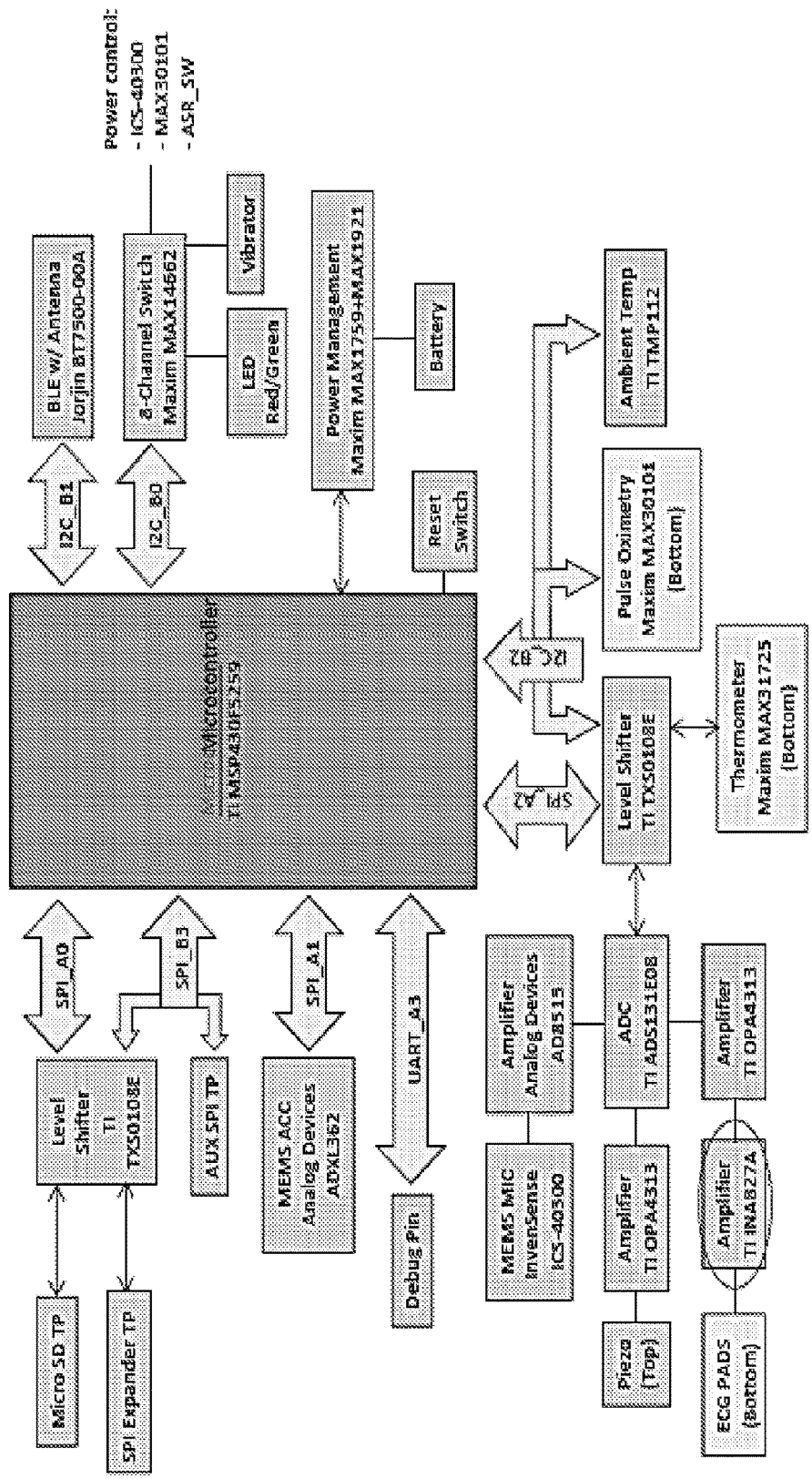
FIG. 37 is an embodiment of a block diagram of a mixed signal board.

FIG. 37 depicts the block diagram of the mixed signal board that contains the sensors, analog and digital signal conditioning and conversion, as well as wireless communications, as detailed in previous figures.

Figure 38B:
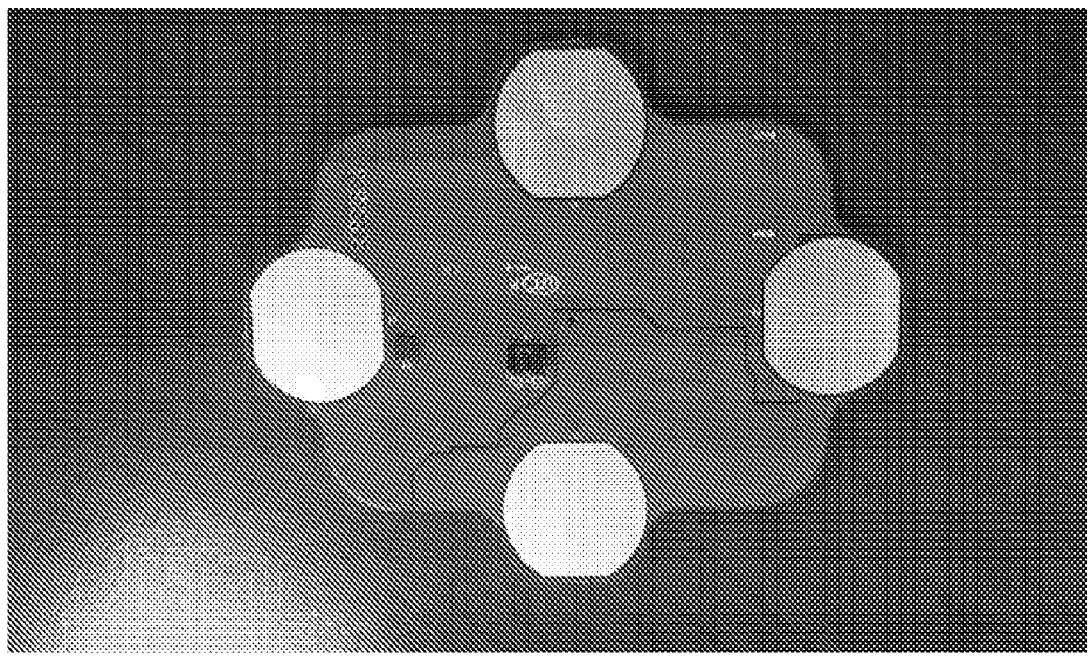
FIG. 38A and FIG. 38B are embodiments of printed circuit boards.
Figure 38A:
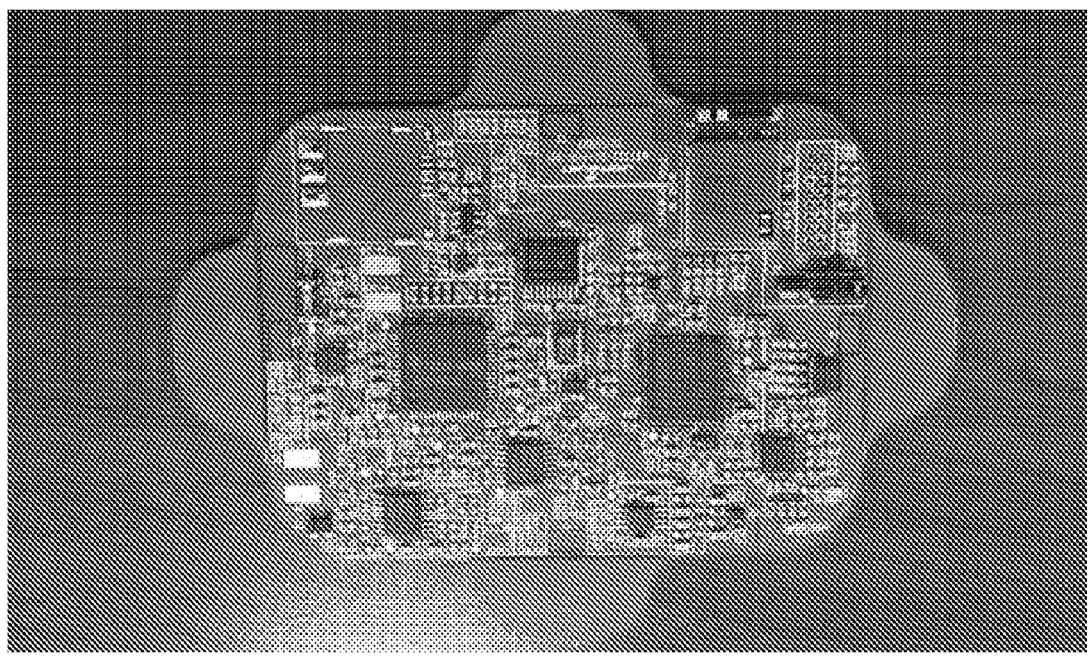

FIG. 38A and FIG. 38B depict exemplary printed circuit boards with four electrodes for measuring parameters.

Figure 39:
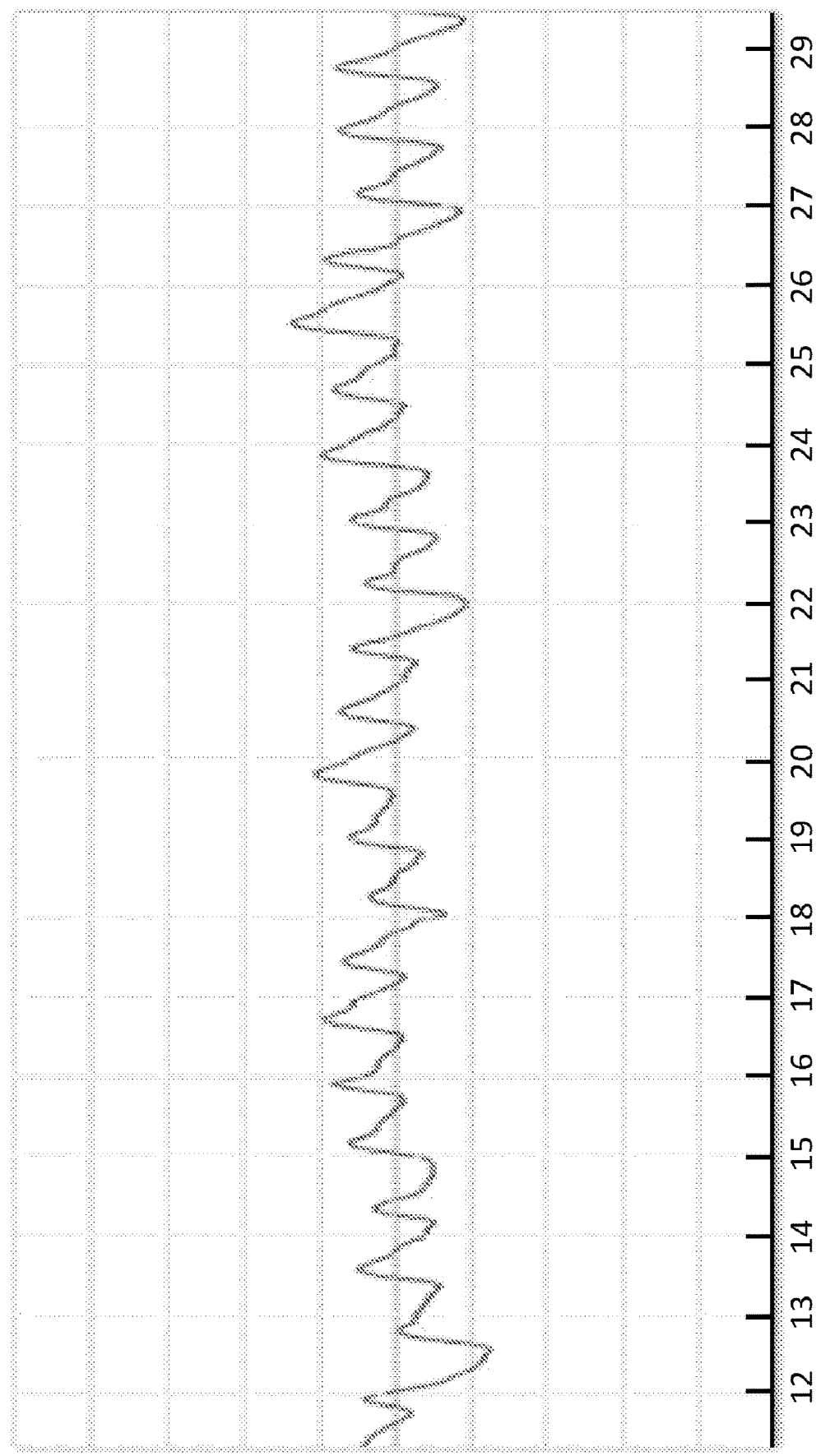
FIG. 39 depicts a piezoelectric sensor's composite signal with a second's grid.

FIG. 39 depicts a piezoelectric sensor's composite signal with a second's grid. A higher frequency (approx. 60 beats/minute or 1 beat/second) blood pressure pulse waveform is shown, with the device near the heart, together with lower frequency modulation by the respiratory effort (under 10 breaths/minute). Following simple filtering, the pulse and the respiration will appear as two distinctive waveforms.

During alert condition, the piezo sensor is converted to a loudspeaker or a buzzer for a local, audible alerting signal.

Figure 40:
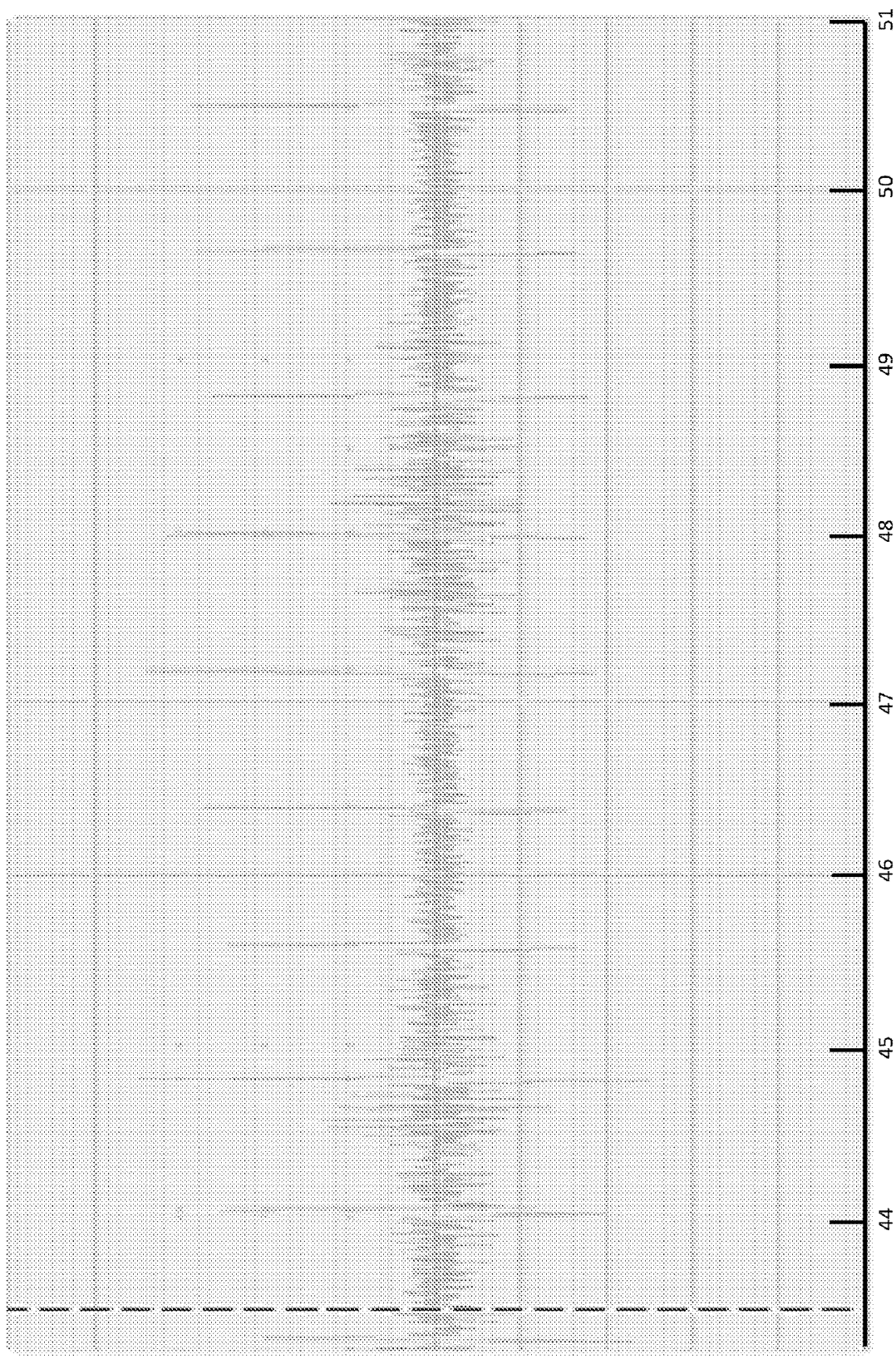
FIG. 40 depicts a composite output between 2 EMG chest electrodes.

FIG. 40 depicts the composite output between 2 EMG chest electrodes, showing the composite output between 2 EMG chest electrodes. The device's placement is on the left torso and particular signal filtering of the EMG (neuromuscular surface signals) shows the EMG respiration effort (thickening of the baseline) with superimposed ECG R waves. The same electrodes pick up the ECG, and the electronics filters the ECG as well as the "R" wave complex, shown elsewhere.

Figure 41:
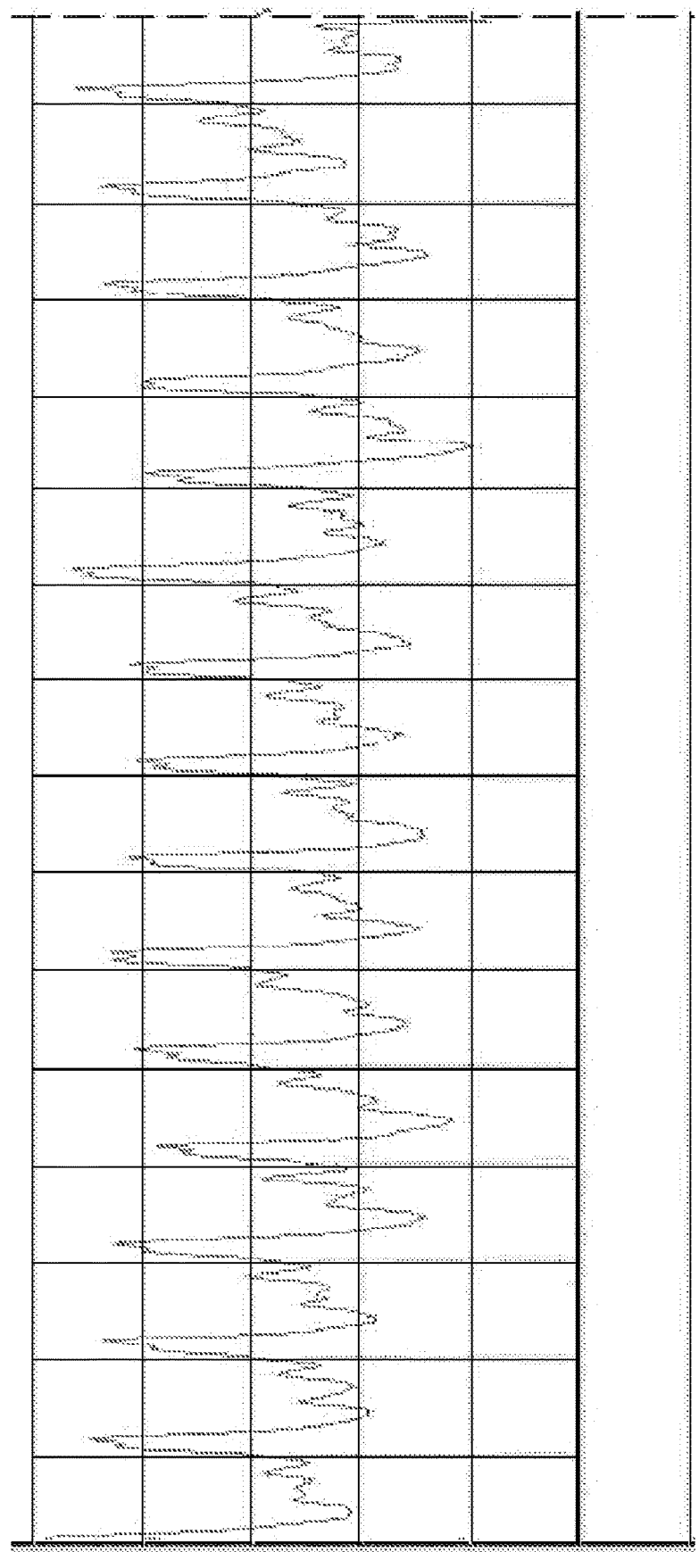
FIG. 41 depicts a device's piezoelectric sensor's pulse waveform signal (Red) and the ECG "R" waves (Green) with chest placement of the device.
Figure 42:
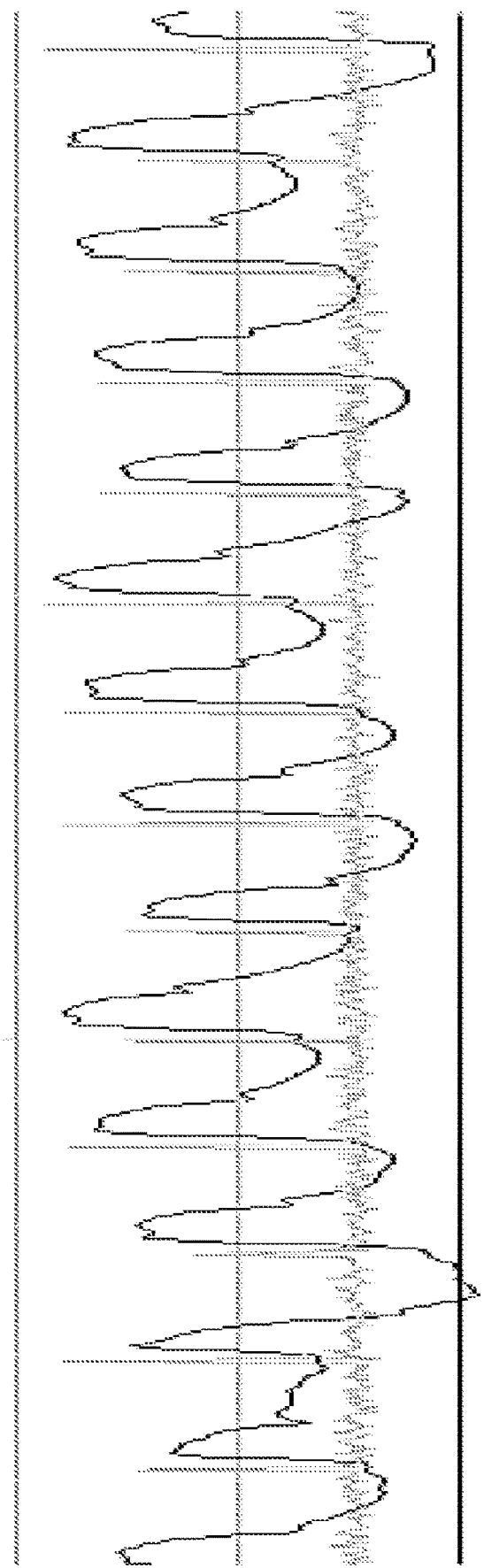
FIG. 42 depicts a device's piezoelectric sensor's pulse waveform signal (Red) and the ECG "R" waves (Green) with neck placement of the device.

FIG. 41 and FIG. 42 depicts the device's piezoelectric sensor's pulse waveform signal (Red) and the ECG "R" waves (Green). Chest placement is seen in FIG. 41 and neck placement in FIG. 42. As can be seen from FIG. 41, each ECG "R" wave peak is followed, after a delay time called PTT (Pulse Transit time) with the pulse wave. The time difference is inversely proportional to blood pressure, thus the device can continuously and non-obtrusively trend the blood pressure variations from a baseline, with no need for a cuff.

In some embodiments, both of the above signals are obtained from a stethoscope diaphragm. The ECG is obtained from conductive contacts on the body side of the diaphragm or from capacitive, non-contact electrodes printed on the inside of the diaphragm. The pulse (and the composite respiration and movement artifacts) is obtained from piezoelectric material such as ink, printed on the inside of the diaphragm. In some embodiments the device further comprises a multi-parameter stethoscope, the membrane being mechanically coupled to a piezoelectric sensor. In some embodiments the piezoelectric sensor doubles as a buzzer or loudspeaker, and is mounted on the top cover of the single board device.

Subtle or intermittent symptoms may be missed in periodic checkup with a standard stethoscope for various reasons (including the physician's hearing acuity and experience, insufficient stethoscope sensitivity, and being intermittent symptoms). Also, the bandwidth and high sensitivity of resulting simultaneous "cardiostethogram" and "respirostethogram" will enable new applications. In some embodiments an application of the device is the detection of obstructive sleep apnea (OSA) with no nasal cannula. The chest movement accompanied by greatly reduced or ceased respiratory sounds indicates the OSA.

Figure 43:
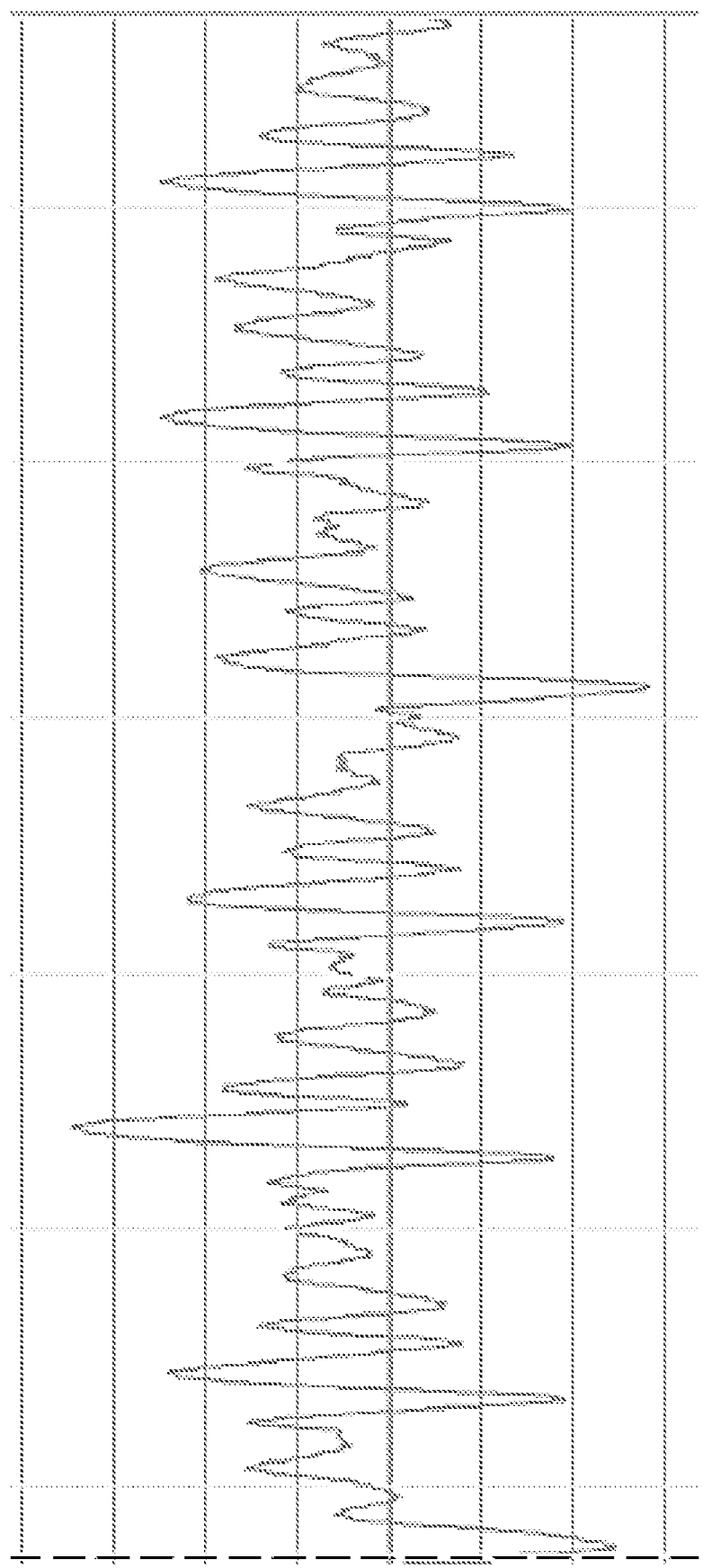
FIG. 43 depicts a non-contact pulse wave & respiration modulation (Piezo sensor embedded in pillow or under mattress).

FIG. 43 depicts a non-contact pulse wave & respiration modulation (Piezo sensor embedded in pillow or under mattress). As seen in FIG. 43, the device comprises the ability to function with no direct contact with a person. The device can then reliably detect cardiac and respiratory events such as tachycardia, bradycardia, central apnea, convulsions due to epileptic or hypo/hyperglycemia events, etc.

In some embodiments, an Intelligent Fall Detector Algorithm is included in the system. The monitor can detect a fall more accurately, thus avoiding false detection. It does so by monitoring physiological changes following an impact. It functions as follows: (1) Physiological baselines are periodically updated, (2) if an impact or a sudden change in body position is sensed, then (3) take a period of heart rate, respiration rate and blood pressure trend change with respect to pre-assume fall baseline, (4) if above parameters changed by more than programmable TBD % (e.g., 5%), then check skin conductance for a startle response (uses a novel circuitry with exceptional sensitivity to overcome the fact that sweat pores at the preferred left body location are not as responsive to stress as those in the palms, fingers, etc.), and (5) if all above prove to confirm a fall, then activate the skin vibrator. This will give the subject an opportunity to override the alert transmission to smartphone or other means, as the fall may have been overcome with no resulting physical problem. Override can be performed by a button press or by coded tap on the monitor. If no override was performed within a given period of time, e.g., 1 minute, then a wireless alert signal is activated.

In some embodiments, an Intelligent Physiological Deterioration Algorithm is included in the system. The occurrence of any apparent life-threatening event (ALTE) or the changes preceding it can be fairly generalized: (1) Physiological baselines are periodically updated within norms, (2) take a period of heart rate, respiration rate and blood pressure trend changes with respect to baseline, (3) if above parameters changed by more than remotely programmable TBD % (e.g., 5%), then (4) activate the skin vibrator, which will give the subject an opportunity to override the alert transmission to Smartphone or other means (override can be performed by a button press or by coded tap on the monitor), and (5) if no override was performed within a given period of time, e.g., 1 minute, then a wireless alert signal is activated. ALTE can include, but not be limited to internal hemorrhage; CHF; Asthmatic or epileptic attack; COPD.

In some embodiments, a Central and Obstructive Apnea (OSA) Algorithm is included in the system. The inclusion of the stethoscope to the EMG and piezo respiration adds a unique, reliable "expert" algorithm with no need for obtrusive nasal canola. The central apnea is detected by no chest effort, no respiration wave, and no breathing sounds. Obstructive apnea is detected by the apparent EMG and piezo respiration waves, as if the subject is breathing. Except that the stethoscope confirms ineffective chest movements by diminished breathing sounds, and the gasping sound and movements following the obstructive apnea period. Furthermore, the stethoscope is sensitive to the snoring sounds as well, so apnea screening is made possible with this monitor. Furthermore, sleep quality record is obtained by counting the sleep time OSA's and central apneas, as well as the duration of each.

In some embodiments, a talking heart rate monitor and pool lap counter/timer is included in the system. The pulse sensor is held by a strap from the goggles. It is completely water proof as it needs no direct contact with the skin. The earphone is embedded inside a snorkel, nothing in the ears.

In some embodiments, a system for real-time monitoring of a subject's physiological condition comprising a micro-monitor with a wireless sensing system-on-module (SOM), a plurality of sensors, a communications module capable of communicating with a wireless technology, and one or more algorithms for monitoring conditions and/or for predicting conditions. The monitor is remotely programmable to activate and deactivate one or more sensors and detect one or more conditions in a subject by monitoring one or more parameters associated with the conditions and comparing any monitored parameter to a baseline measurement of the monitored parameter from the subject. Each sensor corresponds to a monitored parameter and is connected to the micro-monitor to convey measurements of all monitored parameters, the sensors including at least one of a non-optical pulse wave sensor or an electrocardiogram (ECG) sensor. The module can send an alert signal to the subject or an attending physician or a remote service center or any other subject. The algorithms include at least one of a fall detection algorithm or a fall prediction algorithm.

In some embodiments, a system for real-time monitoring of a subject's physiological condition comprising a micro-monitor with a wireless sensing system-on-module (SOM), a plurality of sensors, a communications module capable of communicating with a wireless technology a fall detection algorithm incorporating a startle response monitoring function in addition to physiological changes, a fall prediction algorithm Incorporating a Lissajous pattern analysis of body sway to predict falls, a blood pressure trending algorithm which uses the non-optical pulse sensor with the ECG to measure pulse transit time (PTT), and an automatic distress activated microphone. The monitor is remotely programmable to detect one or more conditions in a subject by monitoring one or more parameters associated with the conditions and comparing any monitored parameter to a baseline measurement of the monitored parameter from the subject. Each sensor corresponds to a monitored parameter and connected to the micro-monitor to convey measurements of all monitored parameters, the sensors comprising at least a non-optical pulse wave sensor and an electrocardiogram (ECG) sensor. The module can send an alert signal to the subject or an attending physician or another person, the alert being transmitted to the subject or the physician or other person upon the monitor detecting a pre-defined and remotely programmed threshold physiological change in a measured parameter as compared to the subject's baseline measurement.

In some embodiments, a method for monitoring a subject's physiological condition comprising (a) placing a monitoring system on a subject, the system configured to detect one or more conditions in the subject, (b) measuring the parameters from the subject at a baseline time to establish a baseline condition for the subject for each parameter, (c) measuring new parameters at a time after the baseline measurement is taken to establish a new condition for the subject for each parameter, (d) comparing the new condition to the baseline condition, and (e) determining if there is a changed condition in the subject for each parameter. The system comprises a micro-monitor with a wireless sensing system-on-module (SOM), the monitor being remotely programmable to detect one or more conditions in a subject by monitoring one or more parameters associated with the conditions and comparing any monitored parameter to a baseline measurement of the monitored parameter from the subject, a plurality of sensors, each sensor corresponding to a monitored parameter and connected to the micro-monitor to convey measurements of all monitored parameters, the sensors comprising at least a non-optical pulse wave sensor and an electrocardiogram (ECG) sensor, a communications module capable of communicating with a wireless technology, wherein the module can send an alert signal to the subject or to an attending physician, and one or more algorithms for monitoring conditions and/or for predicting conditions, the algorithms including at least one of a fall detection algorithm, a fall prediction algorithm, or a blood pressure trending algorithm which uses the non-optical pulse sensor with the ECG to measure pulse transit time (PTT).

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method for monitoring a physiological condition of a subject comprising:
   placing a multi-sensor monitoring system on a subject, the system configured to be positioned on the subject in such a way to detect one or more conditions in the subject, the system comprising:
      a micro-monitor with a wireless sensing system-on-module (SOM), the monitor being remotely programmable to detect one or more conditions in a subject by monitoring one or more remotely programmed parameters associated with the conditions and comparing any remotely programmed monitored parameter to a baseline measurement of the monitored parameter from the subject;
      a plurality of sensors, each sensor corresponding to a monitored parameter and connected to the micro-monitor to convey measurements of all monitored parameters;
         the sensors comprising at least a non-optical pulse wave sensor and an electrocardiogram (ECG) sensor;
      a communications module configured to communicate with a wireless technology, wherein the module is configured to send an alert signal to the subject or to an attending physician, the alert being transmitted upon the monitor detecting the remotely programmed significant physiological change in the monitored parameter as compared to the baseline measurement; and
      one or more algorithms for monitoring conditions and/or for predicting conditions, the algorithms including at least one of a fall detection algorithm, a fall prediction algorithm, or a blood pressure trending algorithm which uses the non-optical pulse sensor with the ECG to measure pulse transit time (PTT); and
   measuring the parameters from the subject at a baseline time to establish a baseline condition for the subject for each parameter;
   measuring new parameters at a time after the baseline measurement is taken to establish a new condition for the subject for each parameter;
   comparing the new condition to the baseline condition; and
   determining if there is a changed condition in the subject for each parameter.

2. The method according to claim 1, wherein determining the changed condition of the subject further comprises differentiating between episodes of central and obstructive apnea.

3. The method according to claim 1, wherein the fall detection algorithm further comprises utilizing information from a sensor for a sensed impact and the algorithm assesses a series of physiological changes including at least a heart rate change and a startle response.

4. The method according to claim 1, wherein the fall prediction algorithm predicts a likelihood of the subject falling by first testing the subject with an X-Y-Z acceleration sensor while the subject is standing to generate a subject baseline state resulting in a simulated line, wherein line lengths comprise an X-Y-Z body sway, wherein a line length of the simulated line is compared to a line length of a second simulated line measured in a second testing of the subject at a later and equivalent period of time, and wherein an increasing line length with respect to the baseline state enables detection by the monitoring system of a progressive postural instability of the subject.

5. The method according to claim 1, further comprising measuring circulation with the ECG and comparing a measurement against a measurement made from the pulse wave sensor and an additional pulse wave sensor, with one on each side of the subject's body to yield a possible difference in two PTT's with respect to an ECG "R" wave.

6. The method according to claim 1, wherein the system is positioned on a left side of the subject's body and to the left of the subject's nipple.

7. The method according to claim 1, wherein each sensor further comprises a conditioning sub-module configured to be powered up or powered down remotely to conserve a battery energy.

* * * * *